United States Patent
Erickson et al.

(10) Patent No.: US 6,943,161 B2
(45) Date of Patent: Sep. 13, 2005

(54) PYRIMIDINE AND TRIAZINE KINASE INHIBITORS

(75) Inventors: Shawn David Erickson, Leonia, NJ (US); James Inglese, Lansdale, PA (US); Jeffrey John Letourneau, East Windsor, NJ (US); Christopher Mark Riviello, Morrisville, PA (US)

(73) Assignee: Pharmacopela Drug Discovery, Inc., Princeton, NJ (US)

( * ) Notice: Subject to any disclaimer, the term of this patent is extended or adjusted under 35 U.S.C. 154(b) by 0 days.

(21) Appl. No.: 10/186,161

(22) Filed: Jun. 28, 2002

(65) Prior Publication Data

US 2003/0149041 A1 Aug. 7, 2003

Related U.S. Application Data

(63) Continuation of application No. PCT/US00/35049, filed on Dec. 22, 2000.
(60) Provisional application No. 60/173,227, filed on Dec. 28, 1999.

(51) Int. Cl.$^7$ .................... C07D 251/54; A61K 31/53; A61P 35/04
(52) U.S. Cl. .................... 514/241; 544/197; 544/198; 544/205; 544/206; 544/207; 544/216; 544/219
(58) Field of Search ................... 544/197, 198, 544/205, 206, 207, 216, 219, 196, 215; 514/241

(56) References Cited

U.S. PATENT DOCUMENTS

| | | | | |
|---|---|---|---|---|
| 3,526,622 A | * | 9/1970 | Varsanyi et al. | 260/247.5 |
| 3,576,895 A | * | 4/1971 | Cantrall et al. | 260/249.6 |
| 4,514,398 A | * | 4/1985 | Regnier et al. | 514/198 |
| 4,514,399 A | * | 4/1985 | Regnier et al. | 544/196 |
| 5,348,956 A | * | 9/1994 | Van Keulen et al. | 514/232.2 |
| 5,641,885 A | * | 6/1997 | Flood et al. | 544/194 |
| 6,150,360 A | * | 11/2000 | Daeyaert et al. | 544/194 |
| 6,251,900 B1 | * | 6/2001 | Kawashima et al. | 544/106 |

FOREIGN PATENT DOCUMENTS

| | | |
|---|---|---|
| WO | WO-93 17009 A1 * | 2/1993 |
| WO | WO-99 05138 A1 * | 4/1999 |
| WO | WO 99/15164 | 4/1999 |
| WO | WO 99/31088 | 6/1999 |
| WO | WO 99/59959 | 11/1999 |
| WO | WO 99/59960 | 11/1999 |
| WO | WO 00/07980 | 2/2000 |
| WO | WO 00/07991 | 2/2000 |
| WO | WO 00/18738 | 4/2000 |
| WO | WO 00/20402 | 4/2000 |
| WO | WO 00/55120 | 9/2000 |
| WO | WO 00/56738 | 9/2000 |
| WO | WO 01/27089 | 4/2001 |

OTHER PUBLICATIONS

Traxler P.M., Exp. Opin. Ther. Patents, 7(6); 571–588, 1997.*

* cited by examiner

*Primary Examiner*—Venkataraman Balasubramanian
(74) *Attorney, Agent, or Firm*—Heslin Rothenberg Farley & Mesiti, P.C.

(57) ABSTRACT

Compounds that selectively inhibit inappropriate kinase activities and methods for their preparation are disclosed. In one embodiment, the compounds are represented by Formula I,

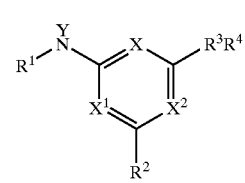

As selective inhibitors of inappropriate kinase activities, the compounds of the present invention are useful in the treatment of conditions associated with such activity, including, but not limited to, inflammatory and autoimmune responses, diabetes, asthma, psoriasis, inflammatory bowel disease, transplantation rejection, and tumor metastasis. Also disclosed are methods of inhibiting inappropriate kinase activities and methods of treating conditions associated with such activities.

30 Claims, No Drawings

PYRIMIDINE AND TRIAZINE KINASE INHIBITORS

FIELD OF THE INVENTION

The invention relates to chemical compounds having kinase inhibitory activity and their use in the treatment of diseases and conditions associated with inappropriate kinase activity.

BACKGROUND OF THE INVENTION

Protein kinases are key elements in signal transduction pathways responsible for transducing extracellular signals to the nuclei, triggering various biological events. [Schlessinger, J. and Ullrich, A., "Growth factor signaling by receptor tyrosine kinases," Neuron, 9:383–391 (1992)] The many roles of protein tyrosine kinases (PTKs) in normal cell physiology include cell growth, differentiation, apoptosis, cell mobility and mitogenesis. [Plowman et al., "Receptor tyrosine kinases as targets for drug intervention," DN&P, 7:334–339 (1994)].

Protein kinases include, for example, but are not limited to, extracellular signal-regulated kinases, p42/ERK2 and p44/ERK1; c-Jun $NH_2$-terminal kinase (JNK); cAMP-responsive element-binding protein kinases (CREB); cAMP-dependent kinase (CAPK); mitogen-activated protein kinase-activated protein kinase (MAPKAP); stress-activated protein kinase p38/SAPK2; mitogen- and stress-activated kinase (MSK); p185$^{neu}$/Her-2/erbB-2; platelet derived growth factor receptor kinase (PDGFR); colony stimulating factor-1 receptor kinase (CSF1-R); endothelial growth factor receptor kinase (EGF-R); vascular endothelial growth factor kinase (VEGF-R); fibroblast growth factor receptor kinase (FGF-R); protein kinases, PKA, PKC and PKC-α; serine/threonine protein kinase (STK); the Janus family of tyrosine protein kinases, JAK1, JAK2 and JAK 3; human insulin receptor tyrosine kinase; the Src-family of cytoplasmic PTKs, p60$^{c-src}$, c-Src, Hck, Fgr and Lyn; Abelson leukemia virus PTK (c-Abl); p56$^{fyn}$ (FYN); p56$^{lck}$ (LCK); cyclin-dependent kinases (CDK1, CDK2, CDK3 and CDK4); NGF receptor kinase (Trk); Alk receptor kinase; IKK-β kinase; Axl/Ufo kinase; Rse/Sky kinase; Syk kinase; ZAP-70 kinase; NIK kinase; Yrk kinase; Fyk kinase; Blk kinase; Csk kinase; Tie-1 and Tie-2 kinase; TrkA, TrkB and Trk C kinases; and human growth factor kinase (HGF).

The disruption of the normal functions of kinases has been implicated in many human diseases, including cancer, diabetes, restenosis, atherosclerosis, fibrosis of the liver and kidney and psoriasis. [Powis, G. and Workman, P., "Signaling targets for the development of cancer drugs," Anti-Cancer Drug Design, 9:263–277 (1994); Cantley et al., "Oncogenes and signal transduction," Cell, 64:281–302 (1991); Kolibaba, K. S. and Druker, B. J., "Protein tyrosine kinase and cancer," Biochim Biophys Acta, 1333:F217–F248 (1997); Merenmies et al., "Receptor tyrosine kinase signaling in vascular development," Cell Growth Differ, 8:3–10 (1997); Lavelle, F., "American Association for Cancer Research 1997: Progress and New Hope in the Fight Against Cancer," Exp Opin Invest Drugs, 6:771–775 (1997); and Shawver et al., "Receptor tyrosine kinases as targets for inhibition of angiogenesis," Drug Discovery Today, 2:50–63 (1997)] In fact, about 30% of human breast and ovarian cancer patients have exhibited increased expression of Her-2 (p185$^{neu}$). [Plowman et al., "Receptor tyrosine kinases as targets for drug intervention," DN&P, 7:334–339 (1994)] Platelet-derived growth factor receptor tyrosine kinases have been associated with human malignancies, arterial restenosis, and fibrosis of the liver, lung and kidney. Colony stimulating factor-1 receptor has been implicated in bone remodeling and hematopoiesis. Vascular endothelial growth factor (VEGF) is a homodimeric peptide growth factor which binds to two structurally related tyrosine kinase receptors denoted Flt1 and KDR. [Waltenberger et al. (Ludwig Institute for Cancer Research, Uppsala Branch, Sweden), "Different signal transduction properties of KDR and Flt1, two receptors for vascular endothelial growth factor," J. Biol. Chem., 269:26988–95 (1994)]. VEGF receptor tyrosine kinases have been implicated in tumor angiogenesis, psoriasis, rheumatoid arthritis, atherosclerosis, and ocular diseases. [Shawver et al., "Receptor tyrosine kinases as targets for inhibition of angiogenesis," Drug Discovery Today, 2:50–63 (1997)]

Further examples of the role of inappropriate kinase activities in various disease states and conditions include, but are not limited to, JAK2 kinase: myelo- and lymphoproliferative disorders [Science, 278:1309–1312 (1997); Blood, 93:2369–2379 (1999)]; Fyn kinase: T-cell leukemia and lymphoma [Curr. Opin. Immunol., 6:372–379 (1994)]; Fgr, Lyn and Hck kinases: rheumatoid arthritis and Crone's disease [J. Exper. Med., 185:1661–1670 (1997)]; Lck kinase: T-cell leukemia and lymphoma [Curr. Opin. Immunol., 6:372–379 (1994)]; Csk kinase: rheumatoid arthritis [J. Clin. Invest., 104:137–146 (1999)]; PKA and PKC kinases: diabetic complications such as blindness [Proc. N.Y. Acad. Sci., 89:11059 (1992)]; c-Abl kinase: chronic myelogenous leukemia [Blood, 93:3973–3982 (1999); J. Cancer Res. Clin. Oncol, 124:643–660 (1998)]; FGFR kinase: Crouzon syndrome, achondroplasia, thanatophoric dysplasia, leukemia, lymphoma and other autoimmune disorders [Nature Genetics, 8:98 (1994); Cell, 78:335 (1994); Nature Genetics, 13:233 (1996)]; ERK1 and ERK2 kinases: head and neck carcinoma [Br. J. Cancer, 80:1412–1419 (1999)]; Tie-1 and Tie-2 kinases: breast cancer [Cancer Research, 59:3185–3191 (1999); Br. J. Cancer, 77:51–56 (1998)]; TrkA, TrkB and TrkC kinases: neuroblastoma [Clin. Cancer Res., 5:1491–1496 (1999)]; IKK-β kinase: inflammation and rheumatoid arthritis [Cell, 90:373–383 (1997); Nature, 388:548–554 (1997); Published PCT application WO 99/34000]; MAPKAP kinase: inflammation and rheumatoid arthritis [Nat. Cell Biol., 1:94–97 (1999)]; p38/SAPK2 kinase: inflammation and rheumatoid arthritis [J. Bio. Chem., 274:19559–19564 (1999); Nature, 372:739–746 (1994); Ann. N.Y. Acad. Sci., 696:149–170 (1993)]; VEGFR kinase: melanoma, cancer, tumor angiogenesis, psoriasis, rheumatoid arthritis, atherosclerosis, ocular diseases and vascular disorders [Blood, 94:984–993 (1999); McMahon et al., "Protein kinase inhibitors: structural determinants for target specificity," Drug Discovery & Development, 1:131–146 (1998)]; HGF kinase: carcinoma and cancer [Int. J. Cancer, 82:449–458 (1999); Jikken Igaku, 16:2016–2025 (1998)]; p185$^{neu}$/Her-2 kinase: breast cancer [Nature, 385:540–544 (1997)]; NIK kinase: inflammation [Nature (London), 398:252–256 (1999)]; Axl/Ufo kinase: myeloid leukemia and prostate cancer [Nature, 368:753–756 (1993); Cancer Detect. Prev., 23:325–332 (1999)]; Rse/Sky kinase: tumors and cell proliferation and breast cancer [J. Biol. Chem., 270:6872–6880 (1995)]; c-Src kinase: colon and breast cancer [Biochem. Biophys. Res. Commun., 250:27–31 (1998); Bone (Osaka), 10:135–144 (1996)]; NGF receptor kinase-Trk: colon cancer [Proc. Nat. Acad. Sci., 91:83–87 (1994); Proc. Nat. Acad. Sci., 84:2251–2253 (1987)]; PDGF kinase: chronic myelomonocytic leukemia, arteriosclerosis and fibrosis of the liver, lung and kidney [*Oncogene,* 7:237–242 (1992); *New Engl. J. Med.,* 314:488–500 (1986)]; Alk receptor kinase: lymphoma [*Cell,* 77:307–316 (1994); *Blood,* 93:3088–3095 (1999); *Oncogene,* 14:4035–4039 (1997)]; Syk kinase: anaplastic large cell lymphoma [*Science,* 263:1281–1284 (1994); *FEBS Lett.,* 427:139–143 (1998); *J. Biol. Chem.,* 273:4035–4039 (1998)]; HIRTK kinase: diabetes [*Science,* 284:974–977 (1999); *Diabetes,* 38:1508 (1989)]; ZAP-70 kinase: immune disorders [*Curr. Biol.,* 9:203–206 (1999); EGFR kinase: carcinoma, psoriasis [*Cancer Research,* 57:4838–4848 (1997); *Cell,* 61:203–212 (1990); *J. Oncology,* 4:277–296 (1994); U.S. Pat. No. 5,654,307 (Aug. 5, 1997)]; JAK3 kinase: immune suppression, leukemia and organ transplant rejection [*Adv. Immunology,* 60:1–35 (1995); *Leuk. Lymphoma,* 32:289–297 (1999)]; *Science,* 270:797–800 (1995)]; and CDK2 kinase: bladder cancer (Published PCT application WO97/16452).

Inappropriate protein kinase activities thus represent attractive targets for therapeutic intervention and in fact, several small molecule kinase inhibitor compounds have been disclosed. Natural products such as staurosporine, lavendustin A, erbstatin, genistein and flavopiridol for example, have been shown to be effective kinase inhibitors. In addition, a number of synthetic tyrosine kinase inhibitors have also been introduced. [McMahon et al., "Protein kinase inhibitors: structural determinants for target specificity," *Drug Discovery & Development,* 1:131–146 (1998)]. The present invention relates to novel compounds effective as inhibitors of inappropriate kinase activities.

SUMMARY OF THE INVENTION

The compounds of the present invention are effective as inhibitors of inappropriate kinase activities and therefore, are useful for the inhibition, prevention and suppression of various pathologies associated with such activities, such as, for example, inflammation, asthma, arthritis, diabetes, atherosclerosis, ocular diseases, restenosis, autoimmune responses, multiple sclerosis, psoriasis, human cancers, fibrosis of the liver, lung and kidney, transplantation rejection, and tumor metastasis.

Accordingly, in one embodiment, the present invention provides a compound, or a salt thereof, represented by Formula I:

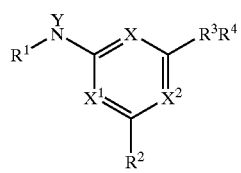

I wherein:

$R^1$ is chosen from —H, $C_1$ to $C_{20}$ hydrocarbon, aminocarbonylalkyl, alkoxyalkyl, substituted arylalkyl, heteroaryl, heteroarylalkyl, heterocyclylalkyl, and substituted heterocyclylalkyl;

$R^2$ is chosen from halogen, $C_1$ to $C_{20}$ hydrocarbon, hydroxy, heteroaryl, substituted heteroaryl, heterocyclyl, substituted heterocyclyl,

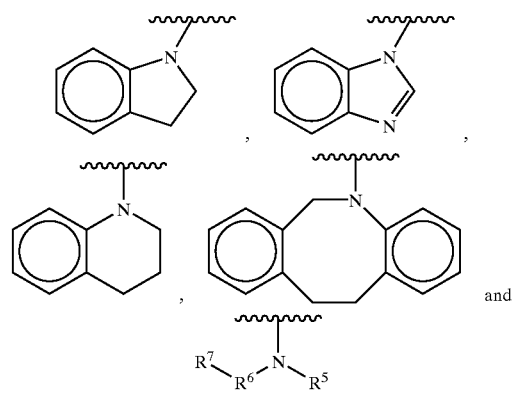

wherein $R^5$ is chosen from —H, alkyl and substituted alkyl;

$R^6$ is chosen from a direct bond, alkyl, aryl, substituted aryl and heteroaryl; and $R^7$ is chosen from —H, acyl, alkyl, substituted alkyl, alkoxycarbonyl, amidine, aryl, arylalkyl, heterocyclyl, heteroaryl, substituted heteroaryl, substituted aryloxy, heteroarylsulfonamido, dialkylsulfonamido,

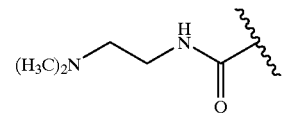

—C(O)NR$^8$R$^9$, —C(NH)NR$^8$R$^9$ and —NR$^8$R$^9$ wherein $R^8$ is chosen from —H and alkyl; and $R^9$ is chosen from —H, alkyl, substituted alkyl, aryl, heteroaryl, alkylcarbonyl and arylcarbonyl;

$R^3$ is chosen from a direct bond,

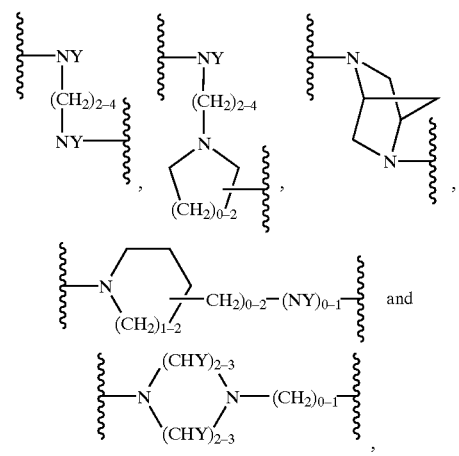

wherein the left hand bond is the point of attachment to the ring and the right band bond is the point of attachment to $R^4$;

$R^4$ is chosen from —H, halogen, alkyl, heterocyclyl, alkylamino, aminocarbonyl,

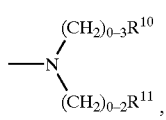

—C(S)NHR$^{12}$, —CHR$^{13}$R$^{14}$, —C(O)NHR$^{15}$, —C(O)(CH$_2$)$_{0\text{-}2}$R$^{16}$—S(O$_2$)R$^{17}$, —OR$^{18}$,

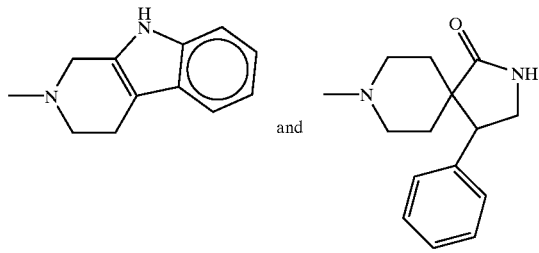

wherein
R$^{10}$ is chosen from —H, —OH, alkyl, cycloalkyl and substituted cycloalkyl;
R$^{11}$ is chosen from —H, —OH, —COOH, aryl, substituted aryl, heteroaryl, substituted heteroaryl, aryl substituted alkyl, cycloalkyl, substituted cycloalkyl, alkoxy, aminocarbonyl, aminocarbonylalkyl,

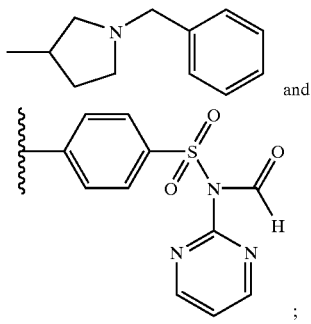

R$^{12}$ is chosen from alkyl and aryl;
R$^{13}$ is chosen from —H and aryl;
R$^{14}$ is chosen from aryl, substituted aryl, heteroaryl, substituted alkyl, aryl substituted alkyl and alkoxy substituted alkyl,
R$^{15}$ is chosen from alkyl, aryl, substituted aryl and substituted alkyl;
R$^{16}$ is chosen from aryl, substituted aryl, heteroaryl, carboxyl, alkoxy, substituted alkyl, cycloalkyl, substituted cycloalkyl, aminocarbonyl, substituted aminocarbonyl, heterocyclyl and

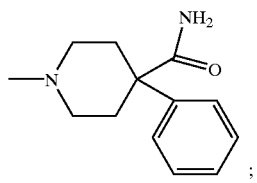

R$^{17}$ is chosen from alkyl and dialkylamino; and
R$^{18}$ is chosen from C$_1$ to C$_{20}$ hydrocarbon, substituted C$_1$ to C$_{20}$ hydrocarbon and heteroaryl;
Y is chosen from —H and lower alkyl, or Y and R$^1$ taken together with the attached N, may be chosen from heterocyclyl, substituted heterocyclyl, heteroaryl and substituted heteroaryl; and
wherein at least two of X, X$^1$ and X$^2$ are —N═, and the other is chosen from —C(H)═ and —N═.

Compounds of Formula I thus include those wherein each of X, X$^1$ and X$^2$ is —N═ and those wherein two of X, X$^1$ and X$^2$ are —N═ and the other is —C(H)═.

Preferred compounds of Formula I, wherein each of X, X$^1$ and X$^2$ is —N═ include:

A) Compounds wherein:
R$^1$ is chosen from C$_1$ to C$_{20}$ hydrocarbon and substituted arylalkyl;
R$^2$ is

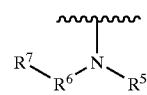

wherein
R$^5$ and R$^7$ are each —H and
R$^6$ is chosen from substituted aryl and heteroaryl;
R$^3$ is chosen from

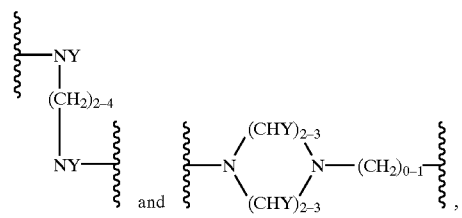

and preferably, from

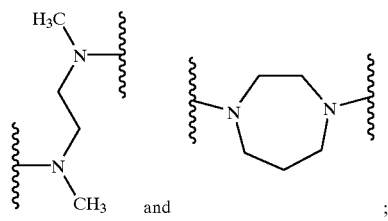

and
R$^4$ is —C(O)NHR$^{15}$ wherein
R$^{15}$ is substituted aryl.

B) Compounds wherein:
R$^1$ is chosen from C$_1$ to C$_{20}$ hydrocarbon, aminocarbonylalkyl, heteroarylalkyl and substituted arylalkyl;
R$^2$ is chosen from

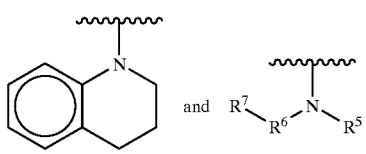

wherein
R$^5$ is chosen from —H and substituted alkyl; and
R$^7$ is chosen from —H, —C(O)NR$^8$R$^9$, —C(NH)NR$^8$R$^9$ and —NR$^8$R$^9$ wherein
R$^8$ is —H; and $R^9$ is chosen from —H, alkyl, aryl and arylcarbonyl;
$R^3$ is chosen from

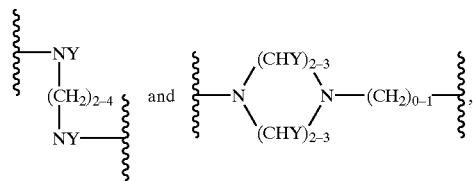

and preferably, from

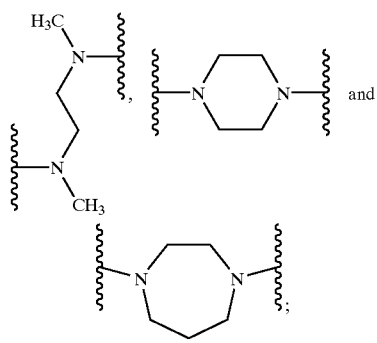

and
$R^4$ is —H.
C) Compounds wherein:
$R^2$ is

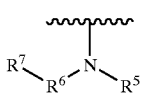

wherein
$R^5$ is chosen from —H and alkyl; and
$R^7$ is chosen from heterocyclyl, substituted heteroaryl, —H, aryl, heteroaryl, substituted alkyl and —NR$^8$R$^9$
wherein
$R^8$ is akyl; and
$R^9$ is substituted alkyl;
$R^3$ is chosen from

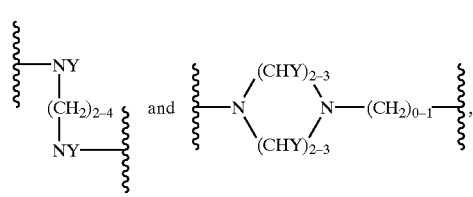

and preferably, from

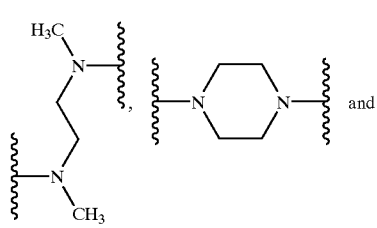

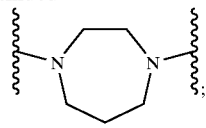

and
$R^4$ is chosen from —C(S)NHR$^{12}$, —C(O)NHR$^{15}$ and —C(O)(CH$_2$)$_{0-2}$R$^{16}$ wherein
$R^{12}$ is aryl;
$R^{15}$ is substituted aryl; and
$R^{16}$ is chosen from substituted aryl and heteroaryl.
D) Compounds wherein:
$R^1$ is chosen from $C_1$ to $C_{20}$ hydrocarbon, aminocarbonylalkyl, substituted arylalkyl, heteroarylalkyl, heterocyclylalkyl, and substituted heterocyclylalkyl;
$R^2$ is chosen from

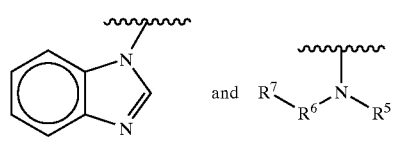

wherein
$R^5$ is —H; and
$R^7$ is chosen from —H, heteroaryl, substituted heteroaryl, and —NR$^8$R$^9$ wherein
$R^9$ is chosen from alkyl carbonyl and substituted alkyl;
$R^3$ is chosen from

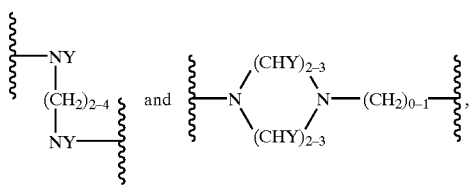

and preferably, from

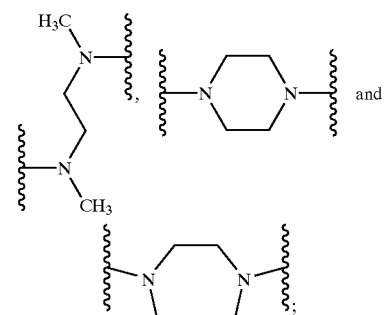

and
$R^4$ is chosen from —H and —C(O)(CH$_2$)$_{0-2}$R$^{16}$
E) Compounds wherein:
$R^1$ is chosen from $C_1$ to $C_{20}$ hydrocarbon, alkoxyalkyl, substituted arylalkyl, heteroarylalkyl, and substituted heterocyclylalkyl;

$R^2$ is chosen from

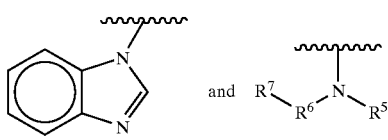

wherein
$R^5$ is chosen from H and alkyl; and
$R^7$ is chosen from —H, heterocyclyl, substituted alkyl, heteroarylsulfonamido, dialkylsulfonamido,

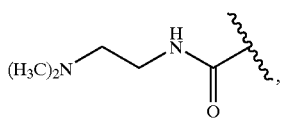

and —NR$^8$R$^9$ wherein
$R^9$ is chosen from alkylcarbonyl, alkyl, substituted alkyl, aryl and arylcarbonyl;
$R^3$ is chosen from a direct bond,

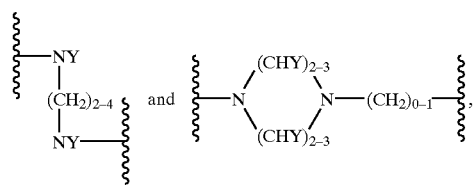

and preferably, from

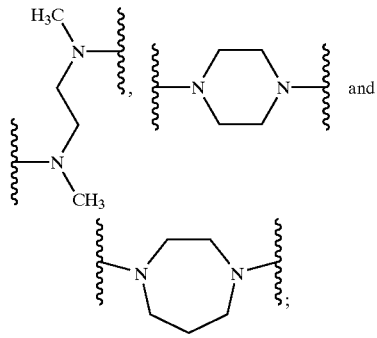

and
$R^4$ is chosen from —H,

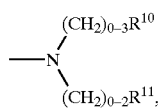

—C(S)NHR$^{12}$, —CHR$^{13}$R$^{14}$, —C(O)NHR$^{15}$ and —C(O)(CH$_2$)$_{0-2}$R$^{16}$ wherein
$R^{10}$ is —H;
$R^{11}$ is —H;
$R^{12}$ is alkyl;
$R^{13}$ is —H;
$R^{14}$ is chosen from heteroaryl, substituted aryl and alkoxy substituted alkyl;
$R^{15}$ is chosen from aryl and substituted aryl; and
$R^{16}$ is substituted aryl.

F) Compounds wherein:
$R^{14}$ is chosen from aryl, substituted aryl, heteroaryl, substituted alkyl and aryl substituted alkyl.

G) Compounds wherein:
$R^1$ is heteroaryl;
$R^2$ is chosen from halogen and

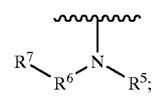

$R^3$ is chosen from a direct bond,

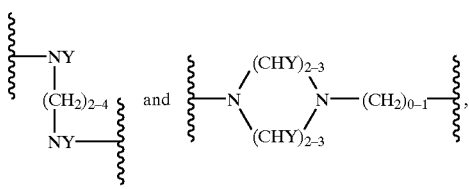

and preferably, from

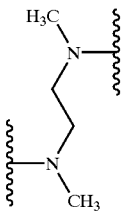

and

and
$R^4$ is chosen from —C(O)(CH$_2$)$_{0-2}$R$^{16}$ and

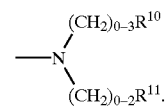

The principles of the present invention also provide methods of inhibiting inappropriate kinase activity in a mammal, wherein the methods comprise administering to the mammal an effective amount of a compound represented by Formula I, or a prodrug or salt thereof. As used herein, inhibiting kinase activity is intended to include inhibiting, suppressing and preventing conditions associated with inappropriate kinase activity, including but not limited to, inflammation, asthma, arthritis, diabetes, atherosclerosis, ocular diseases, restenosis, autoimmune responses, multiple sclerosis, psoriasis, human cancers, fibrosis of the liver, lung and kidney, transplantation rejection, and tumor metastasis.

The principles of the present invention therefore also provide methods of treating a disease or condition associated with inappropriate kinase activity. The methods comprise administering to a mammal in need of such treatment, an effective amount of a compound represented by Formula I, or a prodrug or salt thereof, to inhibit kinase activity, such that the activity is regulated to treat, ameliorate or prevent the disease state or condition associated with that kinase activity. Such conditions include for example, but are not limited to, inflammatory and autoimmune responses, diabetes, asthma, arthritis, atherosclerosis, ocular diseases, restenosis, psoriasis, multiple sclerosis, human cancers, fibrosis of the liver, lung and kidney, inflammatory bowel disease, transplantation rejection, and tumor metastasis. As used herein, "treatment" of a mammal is intended to include prophylaxis and amelioration as well.

Accordingly, the compounds of the invention, as well as prodrugs or salts thereof, may be used in the manufacture of a pharmaceutical composition or medicament for the prophylactic or therapeutic treatment of disease states in mammals. The compounds of the present invention may be administered as pharmaceutical compositions as a monotherapy, or in combination with other therapeutic agents, such as, for example, other antiinflammatory and/or immunosuppressive agents. Such other agents may include, for example, antirheumatic, steroid, corticosteroid, NSAID, antipsoriatic, bronchodilator, antiasthmatic and antidiabetic agents. Combination therapies can involve the administration of the pharmaceuticals as a single dosage form or as multiple dosage forms administered at the same time or at different times.

Any suitable route of administration may be employed for providing a patient with an effective amount of a compound of the present invention. Suitable routes of administration may include, for example, oral, rectal, nasal, buccal, parenteral (such as, intravenous, intrathecal, subcutaneous, intramuscular, intrasternal, intrahepatic, intralesional, intracranial, intra-articular, and intra-synovial), transdermal (such as, for example, patches), and the like. Due to their ease of administration, oral dosage forms, such as, for example, tablets, troches, dispersions, suspensions, solutions, capsules, soft gelatin capsules, and the like, may be preferred. Administration may also be by controlled or sustained release means and delivery devices. Methods for the preparation of such dosage forms are well known in the art.

Pharmaceutical compositions incorporating compounds of the present invention may include pharmaceutically acceptable carriers or excipients, in addition to other therapeutic ingredients. Excipients such as starches, sugars, microcrystalline cellulose, diluents, lubricants, binders, coloring agents, flavoring agents, granulating agents, disintegrating agents, and the like may be appropriate depending upon the route of administration. Because of their ease of administration, tablets and capsules represent the most advantageous oral dosage unit forms. If desired, tablets may be coated by standard aqueous or nonaqueous techniques.

The compounds of the present invention may be used in the form of pharmaceutically acceptable salts derived from inorganic or organic bases, and hydrates thereof. Included among such base salts are ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

DETAILED DESCRIPTION OF THE INVENTION

Abbreviations & Definitions

The following terms and abbreviations retain the indicated meaning throughout this disclosure.

| | | |
|---|---|---|
| ATP | = | adenosine triphosphate |
| DCE | = | dichloroethylene |
| DCM | = | dichloromethane = methylene chloride = $CH_2Cl_2$ |
| DIC | = | diisopropylcarbodiimide |
| DIEA | = | N,N-diisopropylethylamine |
| DMF | = | N,N-dimethylformamide |
| DMSO | = | dimethyl sulfoxide |
| DTT | = | dithiothreitol |
| EDTA | = | ethylenediaminetetraacetic acid |
| Fmoc | = | 9-fluorenylmethoxycarbonyl |
| GST | = | glutathione S-transferase |
| HOBt | = | 1-hydroxybenzotriazole |
| MES | = | 2-(N-morpholino)ethanesulfonic acid |
| i-$Pr_2$NEt | = | diisopropylethylamine |
| $Pr_2$NEt | = | dipropylethylamine |
| TBS | = | t-butyldimethylsilyl |
| TFA | = | trifluoroacetic acid |
| THF | = | tetrahydrofuran |

"Alkyl" is intended to include linear or branched hydrocarbon structures and combinations thereof of 1 to 20 carbons. "Lower alkyl" means alkyl groups of from 1 to about 10, preferably from 1 to about 8, and more preferably, from 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

"Aryl" means an aromatic hydrocarbon radical of 4 to about 16 carbon atoms, preferably of 6 to about 12 carbon atoms, and more preferably of 6 to about 10 carbon atoms. The rings may optionally be substituted with 1–3 substituents selected from alkyl, halogen, hydroxy, alkoxy, aryloxy, haloalkyl, phenyl and heteroaryl. Examples of aryl groups are phenyl, biphenyl, 3,4-dichlorophenyl and naphthyl.

"Arylalkyl" denotes a structure comprising an alkyl attached to an aryl ring. Examples include benzyl, phenethyl, 4-chlorobenzyl, and the like.

"Cycloalkyl" refers to saturated hydrocarbon ring structures of from 3 to 12 carbon atoms, and preferably from 3 to 6 carbon atoms. Examples include cyclopropyl, cyclobutyl, cyclopentyl, cyclohexyl, 2-methylcyclopropyl, cyclopropylmethyl, cyclopentylmethyl, norbornyl, adamantyl, pinanyl, myrtanyl and the like. "Lower cycloalkyl" refers to cycloalkyl of 3 to 6 carbons.

$C_1$ to $C_{20}$ hydrocarbon radicals include alkyl, cycloalkyl, alkenyl, alkynyl, aryl and combinations thereof. Examples include phenethyl, cyclohexylmethyl and naphthylethyl.

"Heterocyclyl" refers to a cyclic hydrocarbon structure of from 1 to 6, preferably 5 to 6, carbon atoms, and containing from 1 to 4 heteroatoms chosen from O, N and S; or a bicyclic 9- to 10-membered heterocyclic system containing from 1 to 4 heteroatoms chosen from O, N and S. "Heteroaryl" refers to an unsaturated cyclic hydrocarbon structure of from 1 to 6, preferably 5 to 6, carbon atoms, and containing from 1 to 4 heteroatoms chosen from O, N and S; or a bicyclic 9- or 10-membered heteroaromatic ring system containing 1–4 heteroatoms selected from O, N and S. The methine H atoms of a heterocyclyl or heteroaryl structure may be optionally substituted with alkyl, alkoxy or halogen. Examples include: imidazole, pyridine, indole, thiophene, benzopyranone, thiazole, furan, benzimidazole, quinoline, isoquinoline, quinoxaline, pyrimidine, pyrazine, tetrazole, pyrazole, pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, imidazolinyl, imidazolidinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dithianyl, thiomorpholinyl, pyrazinyl, piperazinyl, 1,3,5-triazinyl, 1,2,5-trithianyl, benzo(b)thiophenyl, benzimidazolyl, quinolinyl, and the like.

"Alkoxy" means a straight, branched or cyclic hydrocarbon configuration and combinations thereof, including from 1 to 20 carbon atoms, preferably from 1 to 8 carbon atoms, more preferably from 1 to about 4 carbon atoms, and an oxygen atom at the point of attachment. Suitable alkoxy groups include methoxy, ethoxy, n-propoxy, isopropoxy, n-butoxy, iso-butoxy, sec-butoxy, tert-butoxy, cyclopropyloxy, cyclohexyloxy, and the like. "Lower alkoxy" refers to alkoxy groups having from 1 to 4 carbon atoms.

"Alkenyl" refers to an unsaturated acyclic hydrocarbon radical in so much as it contains at least one double bond. "Lower alkenyl" refers to such radicals containing from about 2 to about 10 carbon atoms, preferably from about 2 to about 8 carbon atoms and more preferably 2 to about 6 carbon atoms. Examples of suitable alkenyl radicals include propenyl, buten-1-yl, isobutenyl, penten-1-yl, 2-methylbuten-1-yl, 3-methylbuten-1-yl, hexen-1-yl, hepten-1-yl, and octen-1-yl, and the like.

"Alkynyl" refers to an unsaturated acyclic hydrocarbon radical containing at least one triple bond. Examples include ethynyl, propynyl, and the like.

"Substituted alkyl" means an alkyl wherein at least one hydrogen attached to an aliphatic carbon is replaced with a substituent such as alkyl, amino, alkoxy, aryl, cyano, carboxyl, alkoxycarbonyl, halogen, alkylamino, alkyloxy, alkylcyano, acetyl, hydroxyl, alkylthio, alkylsulphonyl, carboxyalkyl, alkoxyalkyl, alkoxycarbonylalkyl, haloalkyl, acylamino, dialkylamino, and nitro. Examples of such substituent groups include cyano, methyl, isopropyl, methoxy, ethoxy, propoxy, amino, methylamino, phenyl, naphthyl, chlorine, fluorine, and the like.

"Substituted cycloalkyl" means a cycloalkyl wherein at least one hydrogen attached to a ring carbon is replaced with a substituent such as alkyl, amino, alkoxy, aryl, cyano, carboxyl, alkoxycarbonyl, halogen, alkylamino, alkyloxy, alkylcyano, acetyl, hydroxyl, alkylthio, alkylsulphonyl, carboxyalkyl, alkoxyalkyl, alkoxycarbonylalkyl, haloalkyl, acylamino, dialkylamino, and nitro. Examples of such substituent groups include cyano, methyl, isopropyl, methoxy, ethoxy, propoxy, amino, methylamino, phenyl, naphthyl, chlorine, fluorine, and the like.

"Substituted aryl" means an aryl wherein at least one methine hydrogen attached to an aromatic carbon is replaced with a substituent such as alkyl, amino, alkoxy, aryl, acetamido, acetyl, cyano, carboxyl, alkoxycarbonyl, halogen, alkylamino, alkyloxy, alkylcyano, alkylthio, alkylsulphonyl, aminosulphonyl, carboxyalkyl, alkoxyalkyl, alkoxycarbonylalkyl, haloalkyl, acylamino, aminocarbonyl, dialkylamino, and nitro. Examples of such substituent groups include cyano, methyl, isopropyl, methoxy, ethoxy, propoxy, amino, methylamino, phenyl, naphthyl, chlorine, fluorine, and the like. Examples include aryl amides, aryl carboxylic acids, aryl carboxylic acid esters, aryl amidines, and the like, such as benzamide, benzoic acid, benzoic acid ester, benzamidine derivatives and the like.

"Substituted heteroaryl" or "substituted heterocyclyl" means a heteroaryl or heterocyclyl optionally substituted with such substituents as alkyl, amino, alkoxy, aryl, acetyl, cyano, oxo, carboxyl, alkoxycarbonyl, halogen, alkylamino, alkyloxy, alkylcyano, alkylthio, alkylsulphonyl, carboxyalkyl, alkoxyalkyl, alkoxycarbonylalkyl, haloalkyl, acylamino, dialkylamino, and nitro. Examples of such substituent groups include cyano, methyl, isopropyl, methoxy, ethoxy, propoxy, amino, methylamino, phenyl, naphthyl, chlorine, fluorine, and the like.

"Substituted arylalkyl" means an arylalkyl optionally substituted with such substituents as alkyl, amino, alkoxy, aryl, acetyl, cyano, carboxyl, alkoxycarbonyl, halogen, alkylamino, alkyloxy, alkylcyano, alkylthio, alkylsulphonyl, aminosulphonyl, carboxyalkyl, alkoxyalkyl, alkoxycarbonylalkyl, haloalkyl, acylamino, dialkylamino, and nitro. Examples of such substituent groups include cyano, methyl, amino, isopropyl, methoxy, ethoxy, propoxy, methylamino, phenyl, naphthyl, chlorine, fluorine, and the like.

"Halogen" is intended to include for example, F, Cl, Br and I.

The term "prodrug" refers to a chemical compound that is converted to an active agent by metabolic processes in vivo. [See, e.g., N. Boder and J. J. Kaminski, *Ann. Rep. Med. Chem.* 22:303 (1987) and H. Bundgarrd, *Adv. Drug Delivery Rev.*, 3:39 (1989)]. With regard to the present invention, a prodrug of a compound of Formula I is intended to mean any compound that is converted to a compound of Formula I by metabolic processes in vivo. The use of prodrugs of compounds of Formula I in any of the methods described herein is contemplated and is intended to be within the scope of the invention.

Terminology related to "protected," "protecting" and/or "deprotecting" functionalities is used throughout this application. Such terminology is well understood by persons of skill in the art and is used in the context of processes which involve sequential treatment with a series of reagents. In this context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups" for the functionalities involved.

In the case of the present invention, the typical functionalities that must be protected are amines. Suitable groups for that purpose are discussed in standard textbooks in the field of chemistry, such as *Protective Groups in Organic Synthesis* by T. W. Greene [John Wiley & Sons, New York, 1991], which is incorporated herein by reference. Particular attention is drawn to the chapter entitled "Protection for the Amino Group" (pages 309–405). Preferred protecting groups include BOC and Fmoc. Exemplary methods for protecting and deprotecting with these groups are found in Greene and Wuts on pages 318 and 327.

The materials upon which the syntheses described herein are performed are referred to as solid supports, beads, and resins. These terms are intended to include: (a) beads, pellets, disks, fibers, gels, or particles such as cellulose beads, pore-glass beads, silica gels, polystyrene beads optionally cross-linked with divinylbenzene and optionally grafted with polyethylene glycol, poly-acrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and (b) soluble supports such as polyethylene glycol or low molecular weight, non-cross-linked polystyrene. The solid supports may, and usually do, have functional groups such as amino, hydroxy, carboxyl, or halo groups; where amino groups are the most common.

Tentagel™ NH$_2$ (Rapp Polymere, Tubingen, Germany) is a preferred amine functionalized polyethylene glycol-grafted polystyrene resin. Tentagel™-S-PHB resin has a para-hydroxy benzyl linker which can be cleaved by the use of 90% trifluoroacetic acid in dichloromethane. Techniques for functionalizing the surface of solid phases are well known in the art. Attachment of lysine to the amino groups on a bead (to increase the number of available sites) and subsequent attachment of linkers as well as further steps in a typical combinatorial synthesis are described, for example, in PCT application WO95/30642, the disclosure of which is incorporated herein by reference. In the synthesis described in WO95/30642, the linker is a photolytically cleavable linker, but the general principles of the use of a linker are well illustrated.

Optical Isomers—Diastereomers—Geometric Isomers

Some of the compounds described herein contain one or more asymmetric centers and may thus give rise to enantiomers, diastereomers, and other stereoisometric forms which may be defined in terms of absolute stereochemistry as (R)- or (S)-, or as (D)- or (L)- for amino acids. The present invention is meant to include all such possible diastereomers as well as their racemic and optically pure forms. Optically active (R)- and (S)-, or (D)- and (L)-isomers may be prepared using chiral synthons or chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

The configuration of any carbon-carbon double bond appearing herein is selected for convenience only and is not intended to designate a particular configuration; thus a carbon-carbon double bond depicted arbitrarily herein as trans may be cis, trans, or a mixture of the two in any proportion.

In view of the above definitions, other chemical terms used throughout this application can be easily understood by those of skill in the art. Terms may be used alone or in any combination thereof. The preferred and more preferred chain lengths of the radicals apply to all such combinations.

Utility

The compounds of the present invention have demonstrated utility as inhibitors of inappropriate kinase activity. The compounds shown in Table 1 have been synthesized according to the methods described herein and have been tested in accordance with the protocols described below. All of the compounds shown exhibited kinase inhibition with an IC$_{50}$ below 10 μM. Preferred compounds are those with an IC$_{50}$ below 5 μM. More preferred compounds are those with an IC$_{50}$, below 1 μM and most preferred are those with an IC$_{50}$ below 500 nM. These compounds are provided by way of illustration only, and the invention is not intended to be limited thereto.

Biological Assays

Compound Preparation and Assay Format

Compounds were dissolved in dimethylsulfoxide as 10 mM stock solutions. For IC$_{50}$ determinations, serial dilutions were made at 20× the final concentration used in the assay. Assays were carried out in 96-well U-bottom polypropylene microtiter plates.

Jak2 Assay—Casein Substrate/Filtermat Harvest

The final assay volume was 60 μl, prepared by first adding 3 μl of the test compound to 27 μl of a solution containing 5 μM ATP, 10 nM [γ-$^{33}$P]ATP and 12 μM casein in assay buffer (20 mM Tris HCl, pH 8.0, 5 mM MgCl$_2$, 1 mM EDTA and 1 mM DTT), followed by 30 μl of 20 nM GST-Jak2 in assay buffer. The plate was mixed by shaking and then incubated at ambient temperature for 45 min. and terminated by adding 5 μl of 0.5 M EDTA to each sample. The [γ-$^{33}$P]-incorporated casein is harvested onto a GF/C filter-mat (see below) Final concentrations of assay components are: [ATP], 2.5 μM; [casein], 6 μM (10 μg/well); [Jak], 10 nM (~34 ng/well). Staurosporine (1 μM) was used to determine background counts. This assay would also be appropriate for Jak-3 inhibitory activity.

p38(SAPK2) or Erk1 Assay-Myelin Basic Protein/Filtermat Harvest

The assays are performed in V-bottomed 96-well plates. For both assays, the final assay volume is 60 μl prepared from three 20 μl additions of enzyme, substrates [myelin basic protein (MBP) and ATP] and test compounds in assay buffer (50 mM Tris pH 7.5, 10 mM MgCl$_2$, 50 mM NaCl and 1 mM DTT). Bacterially expressed, activated p38 or Erk1 is pre-incubated with test compounds for 10 min. prior to initiation of reaction with substrates. The reaction is incubated at 25° C. for 45 min. and terminated by adding 5 μl of 0.5 M EDTA to each sample. The [γ-$^{33}$P]-incorporated MBP is harvested onto a GF/C filtermat (see below). The final concentration of reagents in the assays are ATP, 1 μM; [γ-$^{33}$P]ATP, 3 nM; MBP (bovine brain, Sigma catalog #M1891), 2 μg/well; activated p38, 10 nM; activated Erk1 (Upstate Biotechnology catalog #14-188), 2.5 μg/mL, 10 nM; DMSO, 0.3%.

IKK-β Assay-GST-IkappaBalpha(1–54)/Filtermat Harvest

The final assay volume is 60 μl prepared from three 20 μl additions of 3× GST-IkappaBalpha(1–54) in assay buffer (20 mM HEPES pH 7.6, 5 mM MgCl$_2$, 50 mM NaCl, 1 mM EDTA and 1 mM DTT) plus test compound, followed by the addition of 3× baculovirus expressed IKK-β (S177E; S181E) in assay buffer which is incubated for 10 min prior to initiation of reaction with a 3×ATP solution (6 μM ATP and 9 nM [γ-$^{33}$P]ATP). The reaction is incubated at 37° C. for 30 min and terminated by harvesting onto a GF/C filtermat (see below). The final concentration of reagents in the assay are ATP, 2 μM; [γ-$^{33}$P]ATP, 3 nM; GST-IkappaBalpha (1–54), 2 μg/well; IKK-β], 5 nM; DMSO, 0.3%.

CDK4 assay-GST-RbSE Substrate/Filter Harvest

The final assay volume is 50 μl prepared from two 25 μl additions of 2× GST-RbSE(768–928) in assay buffer (50 mM HEPES pH 7.5, 10 mM MgCl$_2$, 2.5 mM EDTA, 10 mM β-mercaptoethanol, 2 mM DTT), 20 μM ATP, 0.125 μCi [γ-$^{33}$P]ATP plus test compound, followed by the addition of 2× baculovirus expressed His$_6$-Cdk4/Cyclin D1 complex in assay buffer. The reaction is incubated at ambient temperature for 45 min. and terminated by addition of 50 μl of 250 mM EDTA followed by harvesting onto a GF/C filtermat (see below). The final concentration of reagents in the assay are ATP, 10 $\mu$M; [$\gamma$-$^{33}$P]ATP, 10 nM (0.125 uCi); GST-RbSE (768–928), 2.5 $\mu$M; His$_6$-Cdk4/Cyclin D1 complex (10 $\mu$g per well); DMSO$_{max}$, 2%.

CDK3 Assay-Histone H1 Substrate/Filter Harvest

The final assay volume is 50 $\mu$l prepared from two 25 $\mu$l additions of 2× Histone H1 in assay buffer (50 mM HEPES pH 7.5, 10 mM MgCl$_2$, 2.5 mM EDTA, 10 mM $\beta$-mercaptoethanol, 2 mM DTT), 20 $\mu$M ATP, 0.125 $\mu$Ci [$\gamma$-$^{33}$P]ATP plus test compound, followed by the addition of 2× baculovirus expressed Cdk2/His$_6$-Cyclin E complex in assay buffer. The reaction is incubated at ambient temperature for 45 min. and terminated by addition of 50 $\mu$l of 250 mM EDTA followed by harvesting onto a GF/C filtermat (see below). The final concentration of reagents in the assay are ATP, 10 $\mu$M; [$\gamma$-$^{33}$P]ATP, 10 nM (0.125 $\mu$Ci); Histone H1, 0.5 $\mu$M (1.0 $\mu$g/well); Cdk2/His$_6$-Cyclin E complex, 10 nM; DMSO$_{max}$, 2%.

Protein Kinase A Assay-Histone H1 Substrate/Filter Harvest

The final assay volume is 50 $\mu$l prepared from two 25 $\mu$l additions of 2× Histone (type III-SS) in assay buffer (40 mM Tris-HCl, pH 7.8, Mg(OAc)$_2$), 20 $\mu$M ATP, 0.02 $\mu$Ci [$\gamma$-$^{32}$P] ATP plus test compound, followed by the addition of 2× baculovirus expressed Cdk2/His$_6$-Cyclin E complex in assay buffer. The reaction is incubated at ambient temperature for 45 min. and terminated quenching with 50 $\mu$l of 200 mM EDTA, 75 mM phosphoric acid followed by harvesting onto a GF/C filtermat (see below). The final concentration of reagents in the assay are ATP, 50 $\mu$M; [[$\gamma$-$^{32}$P]ATP, x nM (0.02 $\mu$Ci), Histone, 2.4 $\mu$g/well; PKA, 10U (0.21 $\mu$g); DMSO$_{max}$, 2%.

Src Assay-Zeta Chain Substrate/Plate Binding

The Src kinase assay is based on the phosphorylation of a recombinant His$_6$-zeta chain substrate peptide adsorbed to a Costar 96-well microtiter plate (EIA-RIA High Binding). (Alternatively, the His$_6$-zeta chain can be adsorbed to a Xenopore Nickel plate. If background is a problem, TBS supplemented with 0.02% Tween 20 can replace TBS.)

This assay is carried out in a 50 $\mu$l volume. Plates are first coated with 8–12 $\mu$g/well zeta chain in 100 $\mu$l per well TBS and allowed to stand at 4° C. overnight, followed by a 3× wash with TBS. The plates are blocked using TBS, 1% BSA, 200 $\mu$l per well at ambient temperature for 1 hr, followed by a 3× TBS wash. 25 $\mu$g of Src (100 ng/well) in assay buffer (50 mM HEPES, pH 7.5 and 10 mM MgCl$_2$), followed by addition 25 $\mu$l of test compound and 20 $\mu$M ATP in assay buffer. The reaction is allowed to proceed for 45 min. at ambient temperature with shaking. The reaction is terminated by washing the plate 3× with TBS. Incorporated phosphate is determined by adding 5 ng/well anti-phosphotyrosine-Eu in 100 $\mu$l of TBS, 1% BSA, 50 $\mu$M DPTA and incubating at ambient temperature with shaking for 1 hr. The plate is washed 6× with TBS followed by the addition of 150 $\mu$l of enhancement buffer, shaken for 5 min. and measured on a Victor time-resolved plate reader. The final concentration of reagents in the plate are Src, 0.1U (100 ng); ATP, 10 $\mu$M; DMSO, 0.5%.

c-Abl Assay-Biotin Peptide Substrate/NeutrAvidin Plate Capture

The c-Abl kinase assay is based on the phosphorylation of a biotinylated substrate peptide bound to a NeutrAvidin (Pierce, Rockville, Ill.) coated flat bottom polystyrene 96-well microtiter plate. The phosphorylated peptide product is subsequently detected using an europium-labeled anti-phosphotyrosine antibody (Wallac Oy, Turku, Finland). Assay plates are made 24 hours in advance of the assay by coating a Costar EIA/RIA plate with 50 $\mu$l of 2 $\mu$g/mL NeutrAvadin in TBS using the a Tomtec liquid dispenser. The plate is allowed to stand for 2 hours at ambient temperature or overnight at 4° C. The plate is washed 3× with TBS, 0.1% Tween-20 (TBST). Using the Tomtec liquid dispenser, the plate is next coated with 40 $\mu$l of 100 nM Abl biotinylated substrate peptide (Glu-Ala-Ile-Tyr-Ala-Ala-Pro-Phe-Ala-Lys($\epsilon$-biotin)-NH$_2$) in TBS, 1.0% BSA. The plate is allowed to stand for 2 hours at ambient temperature or up to 1 week at 4° C., and then washed 3× with TBST.

The assay is carried out by the addition of 20 $\mu$l of test compound in assay buffer to the assay plate followed by addition of 40 $\mu$l of a mixture of c-Abl, ATP and anti-pY-Eu in assay buffer. The final concentrations of reagents per well in solution are c-abl, 3U; ATP, 2 $\mu$M; anti-pY-Eu, 0.1 $\mu$g/mL. The plate is vortexed lightly for 5 min. and the reaction is allowed to proceed for 1 hr. at ambient temperature. The reaction is quenched by washing 3× with TBST. Europium counts are measured following the addition of 100 $\mu$l Enhancement solution (Wallac) per well on a Victor time-resolved plate reader (Wallac).

VEGF Kinase Assay

This assay may be used to detect VEGF binding. VEGF is a peptide growth factor that binds to two structurally related tyrosine kinase receptors, Flt1 and KDR. Cultured human umbilical vein endothelial (HUVE) cells express two distinct populations of binding sites with affinities similar to those for Flt1 and KDR, respectively. The KDR expressing cells show striking changes in cell morphology, actin reorganization and membrane ruffling, chemotaxis and mitogenicity upon VEGF stimulation, whereas Flt1 expressing cells lack such responses. KDR undergoes ligand-induced autophosphorylation in intact cells, and both Flt1 and KDR are phosphorylated in vitro in response to VEGF, however, KDR much more efficiently than Flt1. [Waltenberger J. et al. (Ludwig Institute for Cancer Research, Uppsala Branch, Sweden), "Different signal transduction properties of KDR and Flt1, two receptors for vascular endothelial growth factor," *J. Biol. Chem.*, 269:26988–95 (1994)]

Zap-70 Kinase Assay

The assay is performed in black 384-well plates at a final volume of 20 $\mu$l. The bacterial expressed cytoplasmic domain of human erythrocyte band 3 (cdb3) is used as a protein substrate for Zap-70 kinase. The assay plates are coated with cdb3 (10 $\mu$g/mL) at 4° C. overnight, and washed with TBS once. 10 $\mu$l of test compounds in kinase buffer (25 mM MES, pH6.7, 10 mM MnCl$_2$, 0.1% BSA and 2 $\mu$M ATP) is added to each well, followed by the addition of 10 $\mu$l diluted activated Zap-70 to initiate the reaction. The final concentration of reagents in the assays are ATP, 1 $\mu$M; MES$_{pH\,6.7}$, 25 mM; MnCl$_2$, 10 mM; BSA, 0.1%; DMSO, 1%. After incubation at 25° C. for 45 min., reaction solution is removed, and the plates are washed 3× with TBS. 20 $\mu$l of europium-labeled anti-phosphotyrosine antibody (Wallac catalog # CR03-100) at 0.25 $\mu$g/mL is added to each well. The plates are incubated at 25° C. for 1 hr with continuous shaking. The plates are washed 5 times with TBS before 25 $\mu$l of enhancement solution is added to each well. The time-resolved fluorescence is measured using a Victor reader (Wallac).

Reaction Termination by Filtration Harvesting and Data Analysis

After the designated time, the reaction mixture was aspirated onto a pre-wet filtermat using a Skatron Micro96 Cell Harvester (Skatron, Inc.), then washed with PBS. The filtermat is then dried in a microwave oven for 1 min., treated with MeltilLex A scintillation wax (Wallac Oy, Turku, Finland), and counted on a Microbeta scintillation counter Model 1450 (Wallac). Inhibition data were analyzed by nonlinear least-squares regression using Prizm (GraphPad Software).

Methods of Synthesis

General methods of synthesis for compounds of the present invention are illustrated by the following examples. The specific embodiments are presented by way of illustration only, and the invention is not to be limited thereto. Modifications and variations in any given material or process step will be readily apparent to one of skill in the art and are intended to be included within the scope of the invention.

Solution Phase Synthesis of Phenyl Amino Triazines

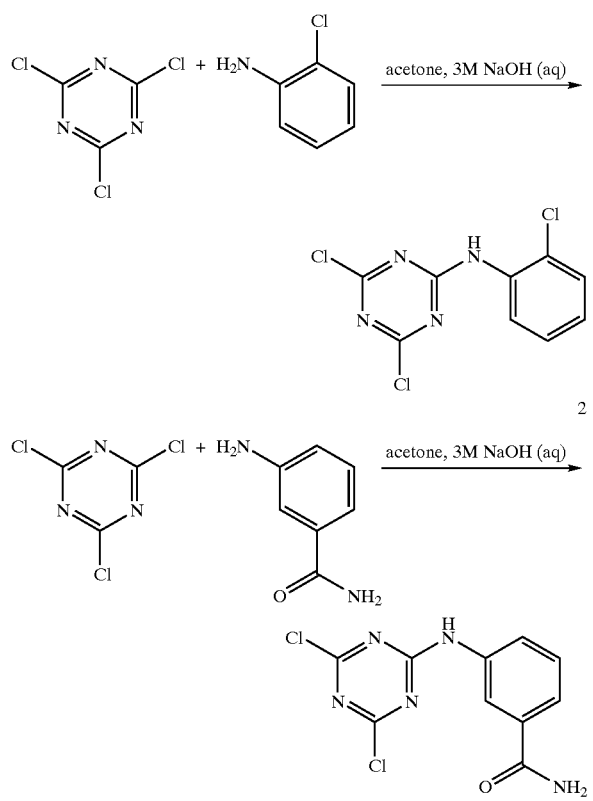

To a solution of cyanuric chloride (1.84 g; 10 mmol) in acetone (15 mL) at 0° C. was added 2-chloroaniline (1.28 g; 10 mmol) and 3.3 mL of 3 M NaOH (aq) (10 mmol). The mixture was stirred at 0° C. for 2 hr. The resultant thick slurry was poured into ice-cold water (approx. 40 mL) and filtered to collect the product as an off white solid. The solid product was then washed with cold $H_2O$ (2×) and cold ethanol (2×) and dried to afford 2.06 g of crude triazine 1 (75% yield) which was suitable for use without further purification. Data for 1: $^1$H NMR ($d_6$-DMSO, 300 MHz) 11.00 (s, 1H), 7.70–7.20 (m, 4H).

To a solution of cyanuric chloride (1.84 g; 10 mmol) in acetone (15 mL) at 0° C. was added 3-aminobenzamide (1.36 g; 10 mmol) and 3.3 mL of 3 M NaOH (aq) (10 mmol). The mixture was stirred at 0° C. for 2 hr. The resultant thick slurry was poured into ice-cold water (approx. 40 mL) and filtered to collect the product as an off-white solid. The solid product was then washed with cold $H_2O$ (2×) and cold ethanol (2×) and dried to afford 2.75 g of crude triazine 2 (80% yield) which was suitable for use without further purification. Data for 2: $^1$H NMR ($d_6$-DMSO, 300 MHz) 11.21 (s, 1H), 8.02 (s, 1H), 7.78 (d, 1H), 7.69(d, 1H), 7.45 (t, 1H).

Derivatization of Resin with bis-Fmoc-lysine

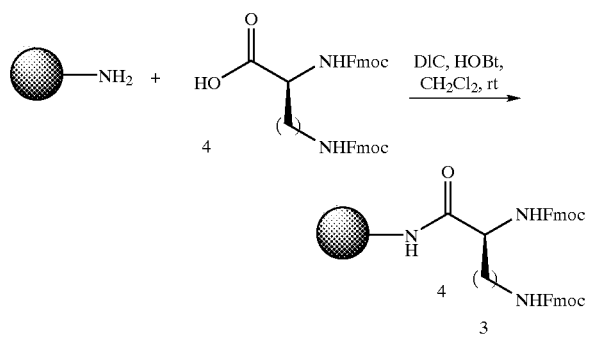

The resin loading was effectively doubled by initial derivatization with bis-Fmoc-lysine using the following procedure. To a suspension of 10.12 g of ArgoGel (0.42 mmol/g, 4.25 mmol, 1.00 eq) in $CH_2Cl_2$ (100 mL) in a large shaking vessel (200 mL capacity) was added bis-Fmoc-lysine (10.04 g, 17.00 mmol, 4 eq), DIC (2.66 mL, 17.00 mmol, 4 eq), and HOBt (2.30 g, 17.00 mmol, 4 eq). The resulting resin suspension was then shaken for 2 hr at 25° C. The resin was washed with DMF (5×) and $CH_2Cl_2$ (5×) and dried in vacuo. The resulting bis-Fmoc-lysine derivatized resin 3 gave a negative result with both the ninhydrin and bromophenol blue tests (tests for primary amine and basic amine functionality).

Fmoc Deprotection of bis-Fmoc-lysine Derivatized Resin

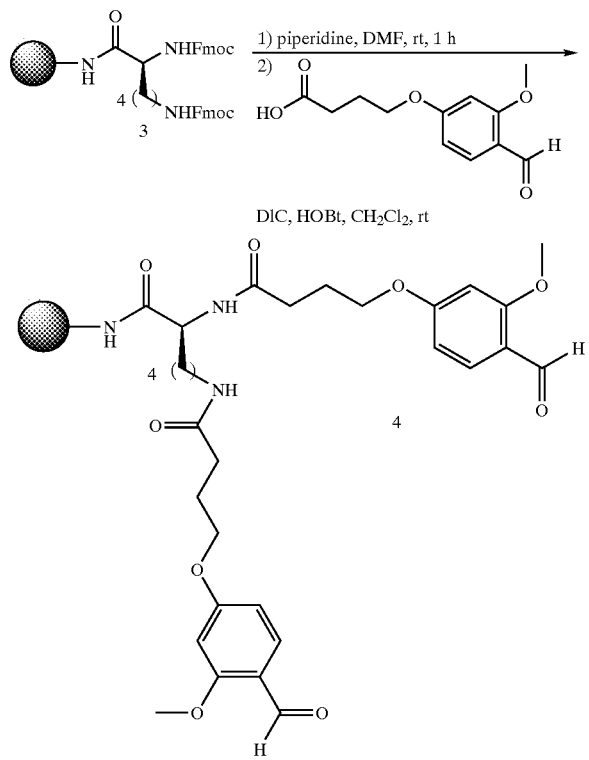

To 12.55 g (0.68 mmol/g, 8.53 mmol, 1.00 eq) of bis-Fmoc-lysine derivatized resin 3 in a large shaking vessel was added 100 mL of a 30% v/v solution of piperidine in DMF. The resulting suspension was shaken for 1 hr at 25° C. The resin was washed with DMF (5×) and CH$_2$Cl$_2$ (5×). The resin-bound deprotected lysine gave a positive result with both the ninhydrin and bromophenol blue tests.

Acylation with the Acid Cleavable Linker

To 11.08 g (0.77 mmol/g, 8.53 mmol, 1.00 eq) of the resin-bound deprotected lysine in CH$_2$Cl$_2$ (100 mL) was added the acid cleavable linker (8.13 g, 34.12 mmol, 4 eq), DIC (5.34 mL, 34.12 mmol, 4 eq), and HOBt (4.61 g, 34.12 mmol, 4 eq). The resulting suspension was shaken overnight at 25° C. The resin was washed with DMF (5×) and CH$_2$Cl$_2$ (5×) and dried in vacuo. The resulting resin-bound product 4 gave a negative test with both the ninhydrin and bromophenol blue tests.

Preparation of Triazine 8:

First Combinatorial Step—Reductive Amination with a Primary Amine

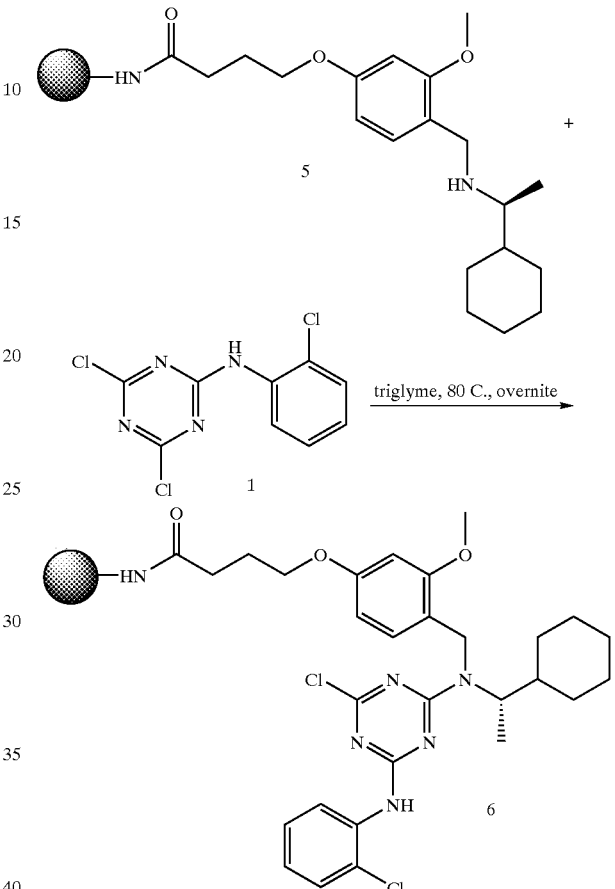

To 300 mg (0.59 mmol/g, 0.177 mmol, 1.00 eq) of the resin-bound o-methoxybenzaldehyde 4 in DCE (10 mL) was added (S)-(+)-cyclohexylethylamine (0.184 mL, 1.24 mmol, 7 eq) and NaHB(OAc)$_3$ (188 mg, 0.885 mmol, 5 eq). The resulting suspension was shaken for 14 hr at 25° C. The resin was washed with DMF (5×) and CH$_2$Cl$_2$ (5×) and then dried in vacuo. The resulting resin-bound secondary amine 5 gave a positive result with the bromophenol blue test.

Second Combinatorial Step—Alkylation with Phenylaminotriazine 1

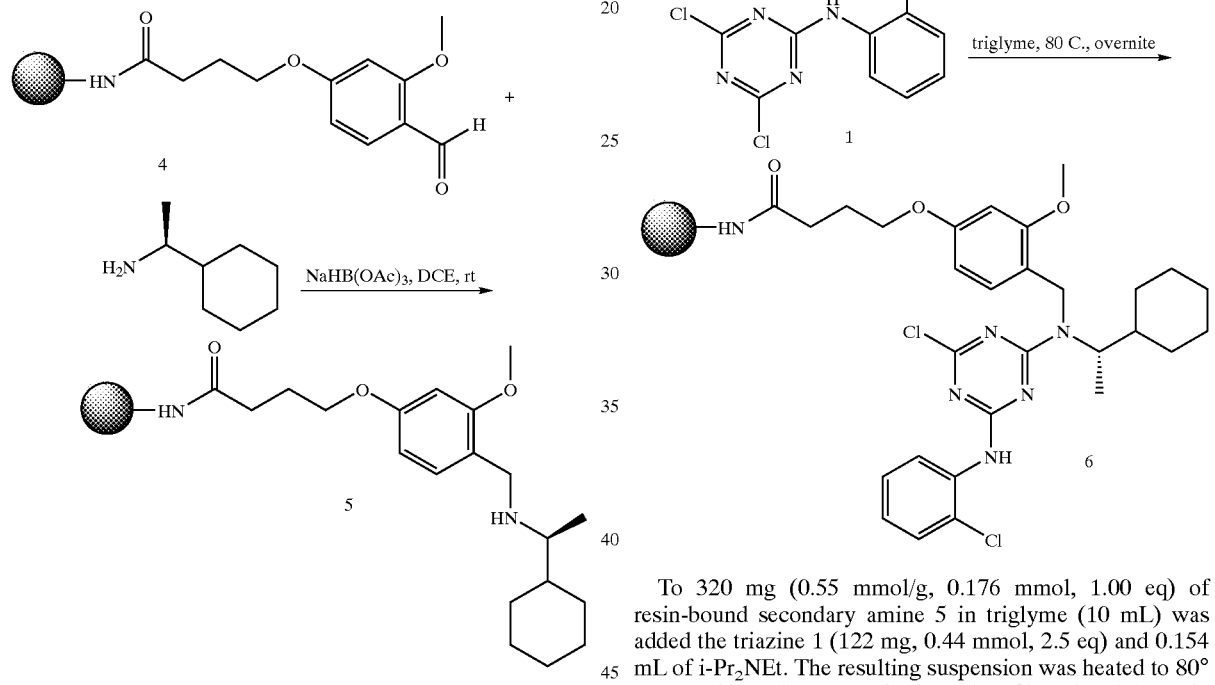

To 320 mg (0.55 mmol/g, 0.176 mmol, 1.00 eq) of resin-bound secondary amine 5 in triglyme (10 mL) was added the triazine 1 (122 mg, 0.44 mmol, 2.5 eq) and 0.154 mL of i-Pr$_2$NEt. The resulting suspension was heated to 80° C. overnight. The suspension was then filtered and the resin washed with DMF (5×) and CH$_2$Cl$_2$ (5×). This was used without drying.

Third Step—Addition of Secondary Amine (Thiomorpholine)

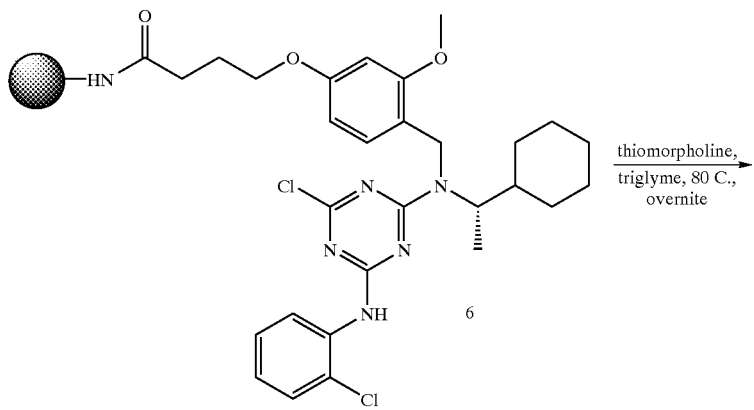

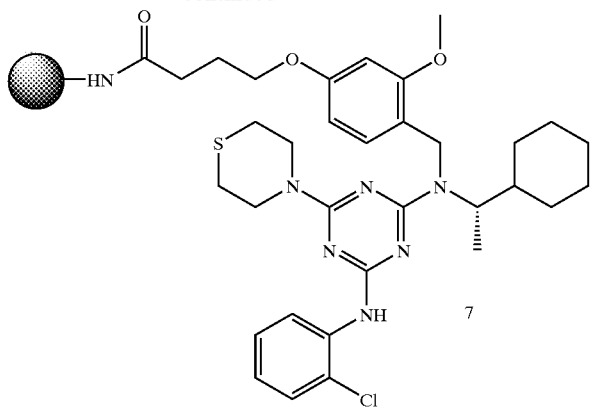

To 362 mg (0.49 mmol/g, 0.177 mmol, 1.00 eq) of resin-bound chlorotriazine 6 in triglyme (4 mL) was added thiomorpholine (1 mL). The resulting suspension was heated to 80° C. overnight. The suspension was filtered and the resin washed with DMF (5×) and CH$_2$Cl$_2$ (5×) and then dried in vacuo.

Acid Cleavage of Resin-bound Trisubstituted Triazine 7

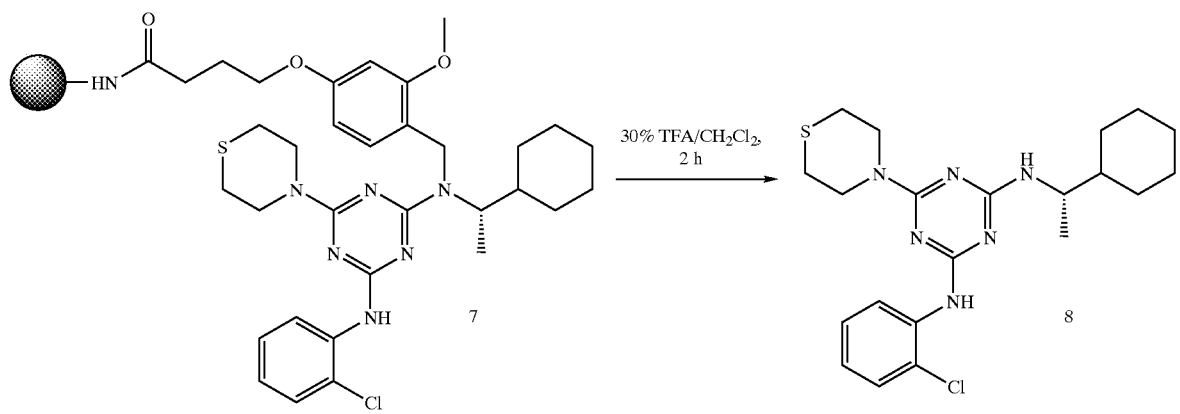

To 319 mg (0.47 mmol/g, 0.150 mmol) of resin-bound triazine 7 was added 10 mL of a 1:1 solution of TFA/CH$_2$Cl$_2$. The resulting mixture was stirred for 2 hr at 25° C. and then filtered. The filtrate was concentrated in vacuo and the residue was purified by flash column chromatography (SiO$_2$, elution with 3:1 hexanes:EtOAc) giving 45 mg of pure trisubstituted triazine 8.

Data for 8: MS: m/z (Relative Intensity) 433.3 (M$^+$, 100), 435.3 (M$^+$+2, 32).

Preparation of Triazine 10: First Combinatorial Step—Reductive Amination with a Primary Amine

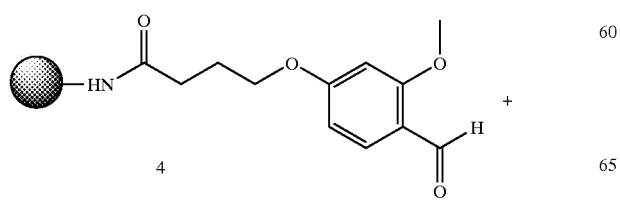

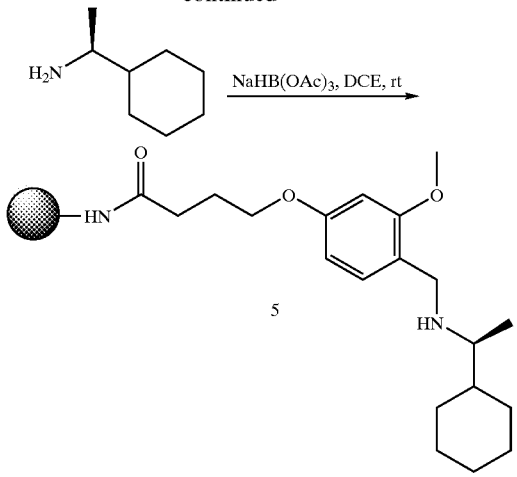

To 300 mg (0.59 mmol/g, 0.177 mmol, 1.00 eq) of the resin-bound o-methoxybenzaldehyde 4 in DCE (10 mL) was added (S)-(+)-cyclohexylethylamine (0.184 mL, 1.24 mmol, 7 eq) and NaHB(OAc)$_3$ (188 mg, 0.885 mmol, 5 eq). The resulting suspension was shaken overnite at 25° C. The resin was washed with DMF (5×) and CH$_2$Cl$_2$ (5×) and then dried in vacuo. The resulting resin-bound secondary amine 5 gave a positive result with the bromophenol blue test.

Second Combinatorial Step—Alkylation with Phenylaminotriazine 2

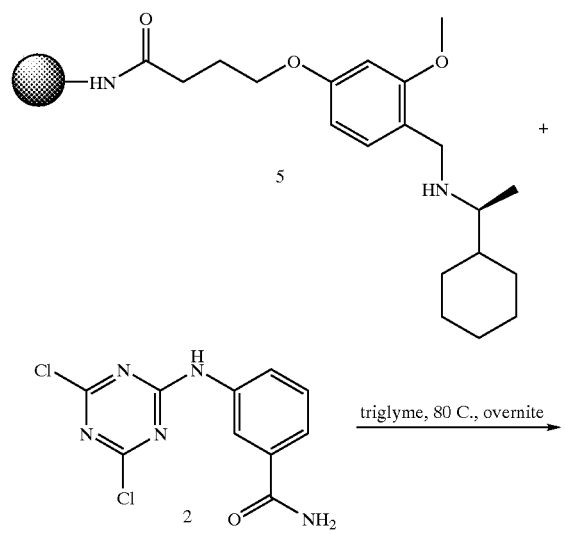

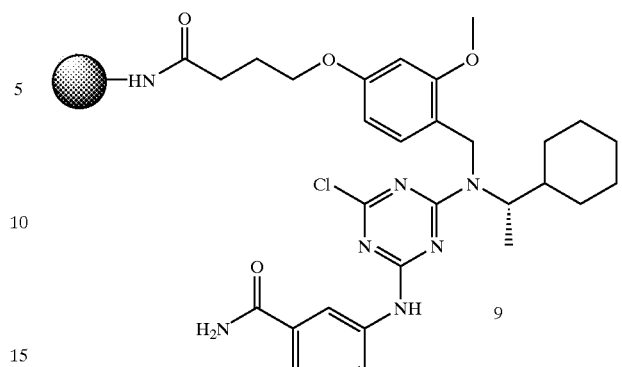

To 320 mg (0.55 mmol/g, 0.176 mmol, 1.00 eq) of resin-bound secondary amine 5 in triglyme (10 mL) was added the triazine 2 (120 mg, 0.44 mmol, 2.5 eq) and 0.154 mL of i-Pr$_2$NEt. The resulting suspension was heated to 80° C. in an oven overnight. The suspension was then filtered and the resin washed with DMF (5×) and CH$_2$Cl$_2$ (5×). This was used without drying.

Third Step—Addition of primary amine (1-(3-aminopropyl)imidazole)

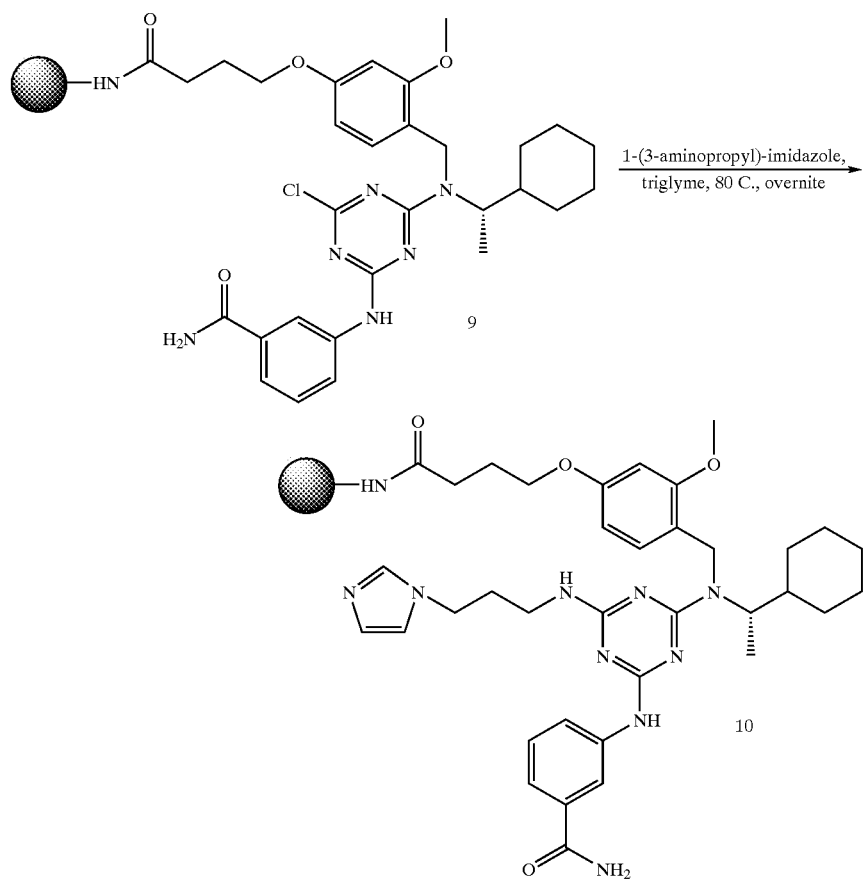

To 364 mg (0.49 mmol/g, 0.178 mmol, 1.00 eq) of resin-bound chlorotriazine 9 in triglyme (4 mL) was added 1-(3-aminopropyl)imidazole (1 mL). The suspension was heated to 80° C. in an oven overnight. The suspension was filtered and the resin washed with DMF (5×) and CH₂Cl₂ (5×). This was then dried in vacuo.

Acid Cleavage of Resin-bound Trisubstituted Triazine 10

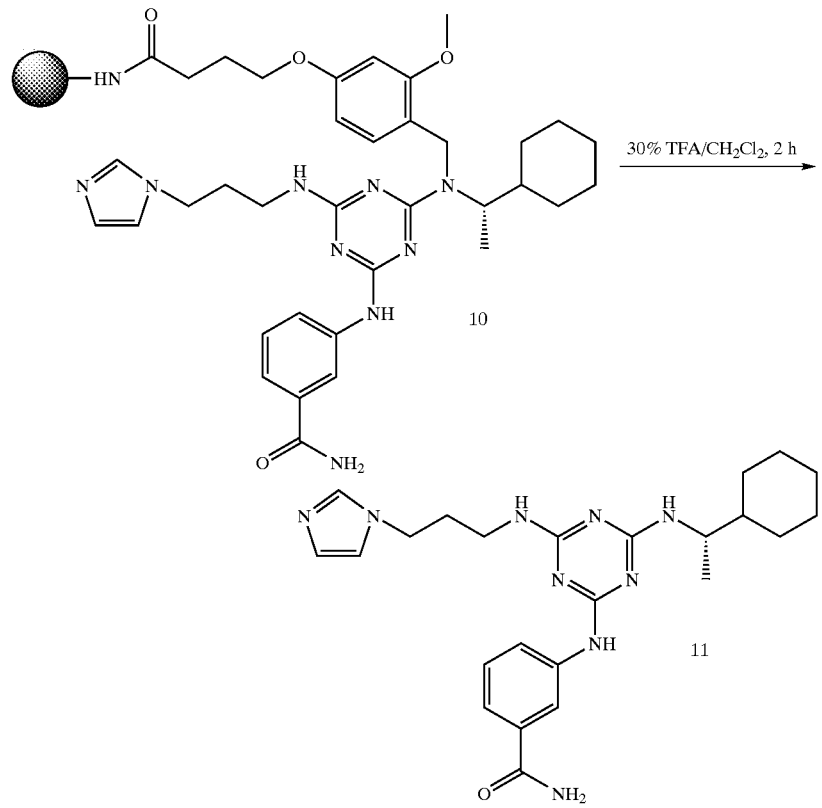

To 131 mg (0.47 mmol/g, 0.062 mmol) of resin-bound triazine 10 was added 10 mL of a 1:1 solution of TFA/CH₂Cl₂. The resulting mixture was stirred for 2 hr at 25° C. and then filtered. The filtrate was concentrated in vacuo and the residue was purified by flash column chromatography (SiO₂, elution with 10% methanol in methylene chloride) giving 8 mg of pure trisubstituted triazine 11. Data for 11: MS: m/z (relative intensity) 464.3 (M⁺+1, 100).

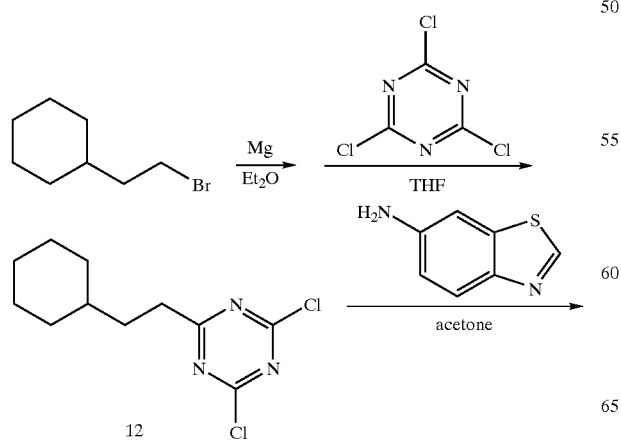

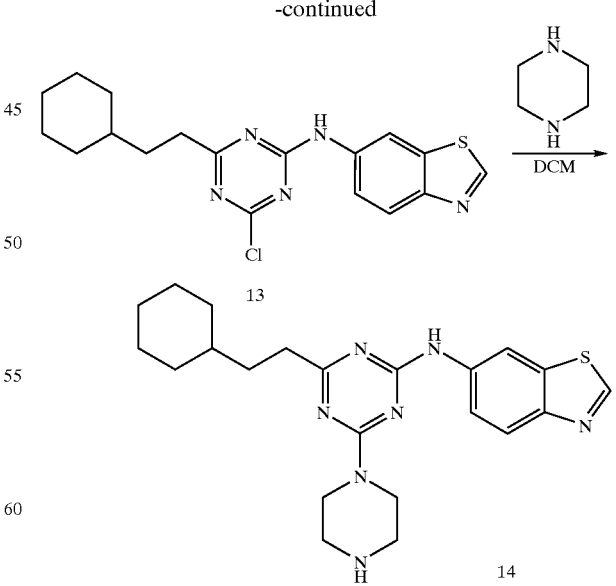

To 1.0 g of magnesium turnings in 15 mL dry ethyl ether was added an iodine crystal and cyclohexylethyl bromide (0.95 g, 5.0 mmol). After 30 minutes the cloudy mixture was transferred to a solution of cyanuric chloride (0.92 g, 5.0 mmol) in 10 mL dry THF. After 2 hr the mixture was concentrated, taken up in DCM and washed with saturated NaHCO$_3$ and brine. The organic layer was dried over MgSO$_4$. Filtration and removal of volatiles under reduced pressure gave 12 as an oil. (0.88 g, 3.4 mmol, 68%, M+H$^+$=261)

To 12 (0.42 g, 1.6 mmol) in 20 mL acetone was added 6-aminobenzothiazole (0.29 g, 1.9 mmol) and stirred at room temperature for 1 hr. The mixture was concentrated, taken up in DCM and washed with saturated NaHCO$_3$ and brine. The organic layer was dried over MgSO$_4$. Filtration and removal of volatiles under reduced pressure gave 13 as a solid. (0.022 g, 0.06 mmol, 4%, M+H$^+$=374)

To 13 (0.022 g, 0.06 mmol) in 3 mL DCM was added 100 mg of piperazine and stirred at room temperature for 3 hr. The mixture was concentrated, dissolved in DCM and washed with saturated NaHCO$_3$ and brine. The organic layer was dried over MgSO$_4$. Filtration and removal of volatiles under reduced pressure gave 14 as a solid. (0.013 g, 0.03 mmol, 50%, M+H$^+$=424)

stirred at room temperature overnight. The mixture was then concentrated, dissolved in DCM and washed with saturated NaHCO$_3$. The organic layer was extracted into 1N HCl and washed twice with DCM. The aqueous layer was adjusted to pH 12 with 3N NaOH and extracted with DCM. The combined organic layers were dried over MgSO$_4$. Filtration followed by removal of volatiles under reduced pressure gave 15 as an oil (0.43 g, 2.6 mol, 26%, M+H$^+$=166)

0.26 g (1.6 mmol) of 15 was taken up in 15 mL EtOH and placed in a Parr hydrogenation apparatus with 50 mg of 10% Pd/C and shaken at 50 psi for 6 hr. The solution was filtered through Celite and concentrated. The resulting oil was taken up in DCM and washed with saturated NaHCO$_3$ and brine. The organic layer was dried over MgSO$_4$. Filtration and removal of volatiles under reduced pressure gave 16 as an oil. (0.13 g, 0.75 mmol, 46%, M+H$^+$=168)

Compound 16 (0.05 g, 0.3 mmol) was combined with 17 (0.09 g, 0.2 mmol) and DIEA (53 μL, 0.3 mmol) in 5 mL DMF and heated to 60° C. overnight. The mixture was then concentrated, taken up in DCM and washed with saturated KHSO$_4$, saturated NaHCO$_3$, and brine. The organic layer was concentrated to yield 18 as a foam. (0.055 g, 0.09 mmol, 32%, M+H$^+$=579).

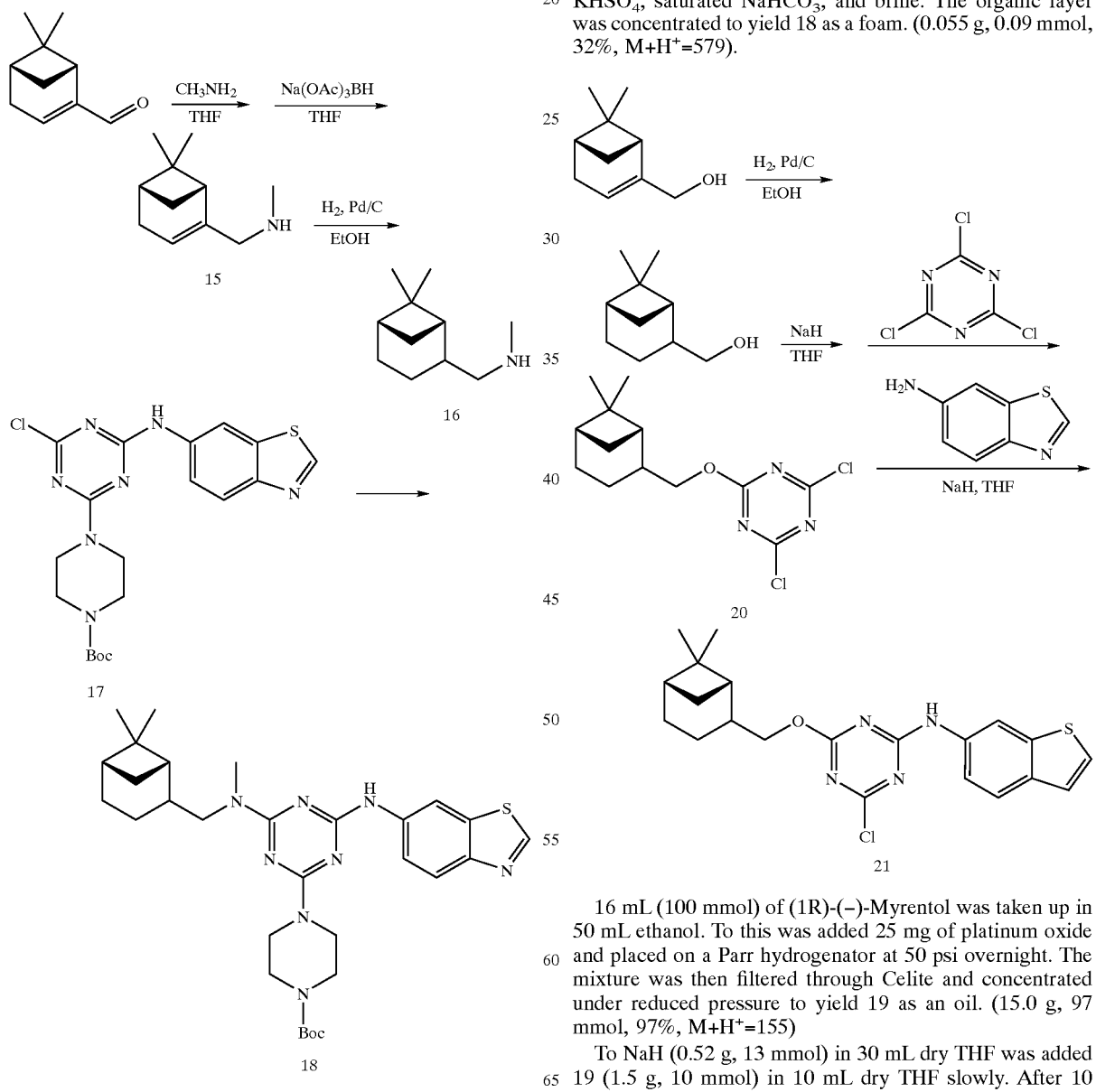

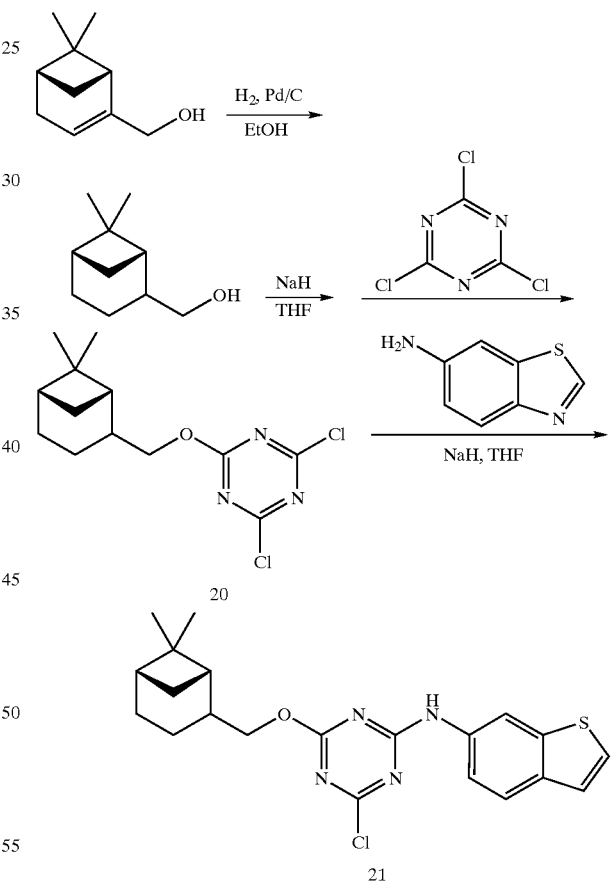

To (1R)-(−)-Myrentol in 10 mL THF was added methylamine (2.0M in THF, 7.5 mL), then NaHB(OAc)$_3$ and 16 mL (100 mmol) of (1R)-(−)-Myrentol was taken up in 50 mL ethanol. To this was added 25 mg of platinum oxide and placed on a Parr hydrogenator at 50 psi overnight. The mixture was then filtered through Celite and concentrated under reduced pressure to yield 19 as an oil. (15.0 g, 97 mmol, 97%, M+H$^+$=155)

To NaH (0.52 g, 13 mmol) in 30 mL dry THF was added 19 (1.5 g, 10 mmol) in 10 mL dry THF slowly. After 10 minutes, cyanuric chloride (1.8 g, 10 mmol) in 10 mL dry THF was added slowly. The reaction mixture was stirred at room temperature overnight. Water (5 mL) was slowly added to the mixture. The mixture was then concentrated, dissolved in DCM and washed with saturated NaHCO₃ and brine. The organic layer was dried over MgSO₄. Filtration and removal of volatiles under reduced pressure gave 20 as an oil. (0.64 g, 2.1 mmol, 21%, M+H⁺=303)

To NaH (0.07 g, 1.72 mmol) in 10 mL dry THF was added dropwise a solution of 6-aminobenzo thiazole(0.20 g, 1.33 mmol) in 5 mL dry THF. After 10 minutes, 20 (0.44 g, 1.46 mmol) in 5 mL dry THF was added dropwise. The reaction mixture was stirred at room temperature for 2 h, after which 5 mL of water was added slowly. The mixture was then concentrated, dissolved in DCM and washed with saturated NaHCO₃ and brine. The organic layer was dried over MgSO₄. Filtration and removal of volatiles under reduced pressure gave 21 as a solid. (0.45 g, 1.1 mmol, 83%, M+H⁺=416)

Compounds of Formula I wherein two of X, X¹ and X² are —N= and the other is —C(H)= may be synthesized as follows:

of i-Pr₂NEt and 500 mg 6-imidazolyl-2,4-dichloropyrimidine (2.0 mmol) in DMF at 50° C. for 16 hr, then diluted with ethyl acetate and washed with saturated NH₄Cl, H₂O, brine, dried over MgSO₄ and concentrated and purification by flash chromatography (eluted with 8:10:1 EtOAc:Hexanes:MeOH) to give 23 and 24.

92 mg of 23 (0.21 mmol) in 3 mL of n-butanol is treated with 0.9 mL of 3-chlorobenzylamine and 1 mL of i-Pr₂NEt at 100° C. for 16 hr, then cooled to room temperature, diluted with ethyl acetate and washed with saturated NH₄Cl, H₂O, brine, dried over MgSO₄ and concentrated. The crude product is purified by flash chromatography (eluted with 4:5:1 EtOAc:Hexanes:MeOH) to give 25.

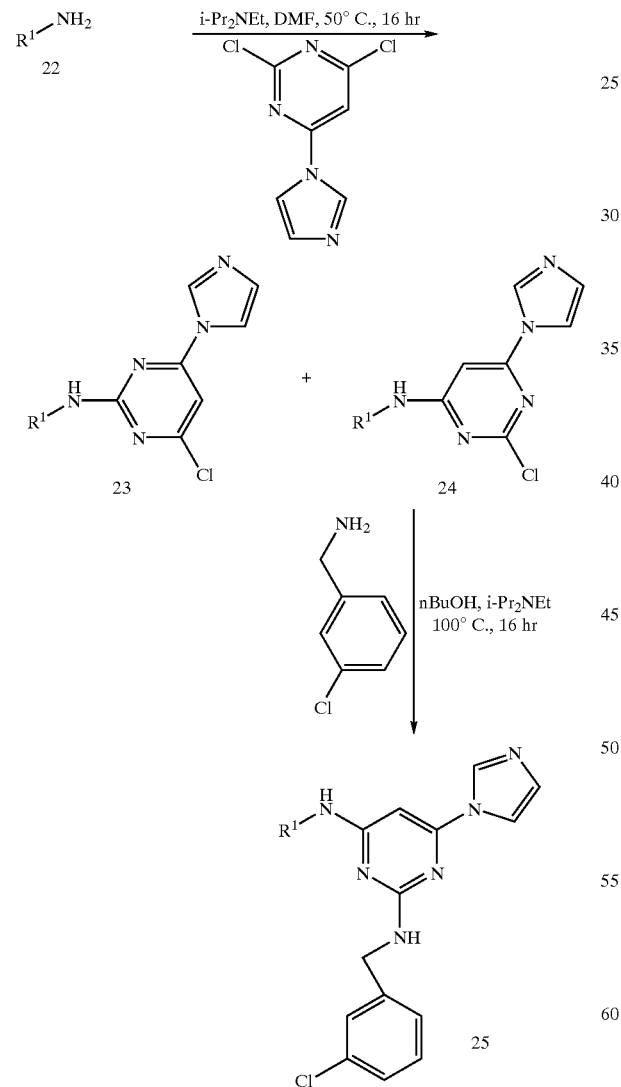

SCHEME 1

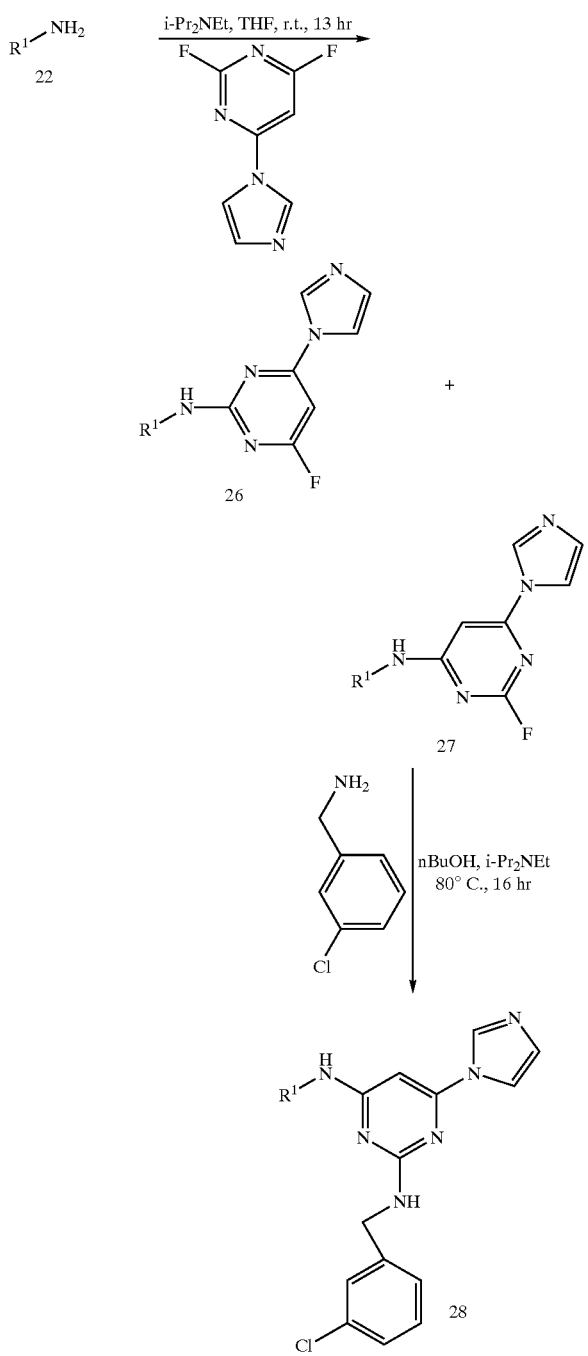

SCHEME 2

Scheme 1 illustrates a solution phase synthesis via chloropyrimidines and Scheme 2 illustrates a solution phase synthesis via fluoropyrimidines. As shown in Scheme 1,390 mg of the free amine 22 (1.1 mmol) is treated with 0.6 mL Alternatively, as illustrated in Scheme 2, 280 mg of the free amine 22 (1.1 mmol) is treated with 0.25 mL of i-Pr₂NEt and 200 mg of 6-imidazolyl-2,4-difluoropyrimidine (1.1 mmol) in THF at room temperature for 13 hr, then diluted with ethyl acetate and washed with saturated NH₄Cl, H₂O, brine, dried over MgSO₄ and concentrated. The crude product is purified by flash chromatography (eluted with 8:10:1 EtOAc:hexanes:MeOH) to give 26 (less polar product) and 27 (more polar product). Four hundred fifty milligrams of 27 (1.08 mmol) in 50 mL of THF or n-butanol is then treated with 1.7 g of 3-chlorobenzyl amine and 5 mL of i-Pr₂NEt at 80° C. for 16 hr then diluted with ethyl acetate and washed with saturated NH₄Cl, H₂O, brine, dried over MgSO₄ and concentrated. The crude product is purified by flash chromatography (eluted with 6:12:1 EtOAc:hexanes:MeOH) to give 28.

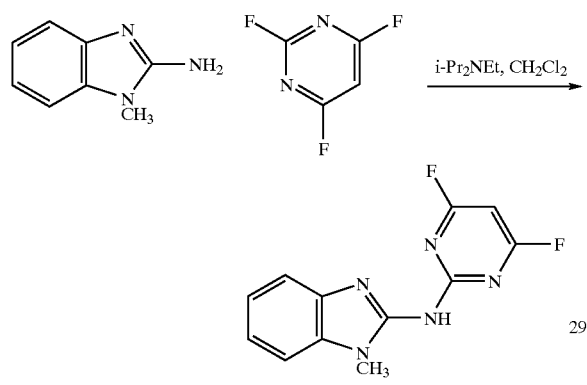

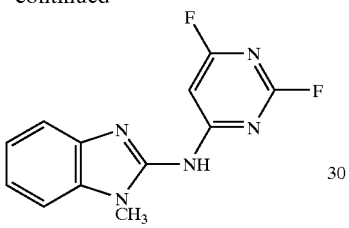

2-amino-1-methylbenzimidazole (5.15 g, 35 mmol) was added to a solution of trifluoro pyrimidine (4.40 g, 32.8 mmol) and iPr₂NEt (5.9 mL, 34 mmol) in CH₂Cl₂. After 16 hr, the reaction mixture was concentrated to approximately 30 mL. The two regioisomers, 2-(2-amino-1-methylbenzimidazole)-4,6-difluoropyrimidine 29 and 4-(2-amino-1-methyl benzimidazole)-2,6-difluoropyrimidine 30 were separated by silica gel chromatography (50–100% ethyl acetate in toluene). 2.04 g (23%) of the 4-substituted regioisomer and 2.17 g (25%) of the 2-substituted regioisomer were isolated.

2-(2-amino-1-methylbenzimidazole)-4,6-difluoropyrimidine (29)

¹H NMR (CDCl₃, 300 MHz) δ8.38, d, 1H; 8.23 bs 7.22, dd 1H; 7.06, dd, 1H; 6.88, d, 1H; 6.38, s, 1H; 3.42, s, 3H.

¹⁹F NMR (CDCl₃, 75 MHz) 39574 Hz.

4-(2-amino-1-methylbenzimidazole)-2,6-difluoropyrimidine (30)

¹H NMR (CDCl₃, 300 MHz) δ 8.65, bs, 1H; 8.40, bs, 1H; 7.04–7.22, m, 3H; 6.87, d, 1H; 3.31, s, 3H.

¹⁹F NMR (CDCl³, 75 MHz) 42596 Hz, 38829 Hz.

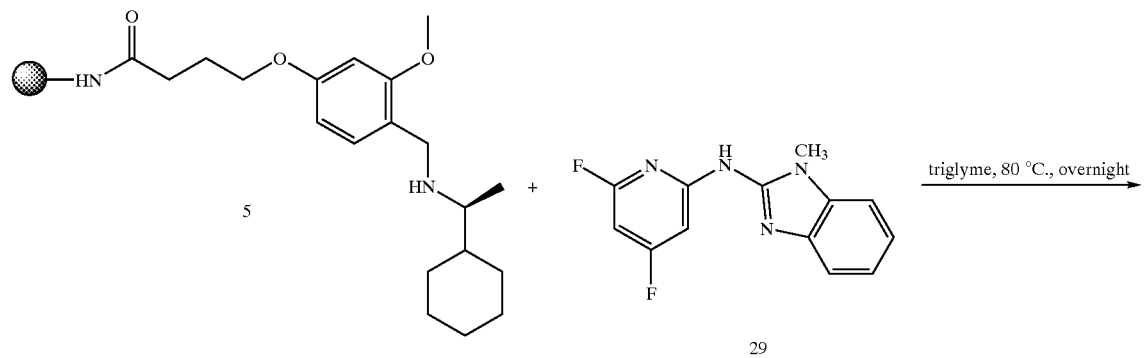

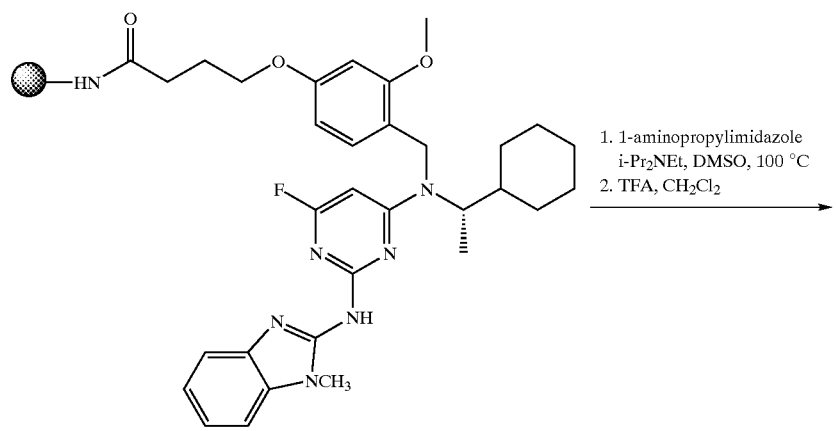

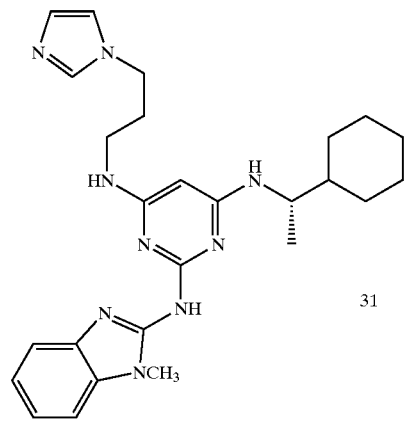

31

To 500 mg (0.55 mmol/g, 0.275 mmol) of resin-bound secondary amine 5 in triglyme (10 mL) was added 29 (143 mg, 0.55 mmol) and 0.154 mL of i-Pr$_2$NEt (175 μL, 1 mmol). The resulting suspension was heated to 80° C. for 16 hr. The suspension was then filtered and the resin washed with DMF (5×) and CH$_2$Cl$_2$ (5×). Bromophenol blue test was negative indicating complete reaction of the resin-bound secondary amine.

To 450 mg (0.248 mmol) of resin-bound fluoropyrimidine in DMSO (4 mL) was added 1-(3-aminopropyl)imidazole (1 mL). The suspension was heated to 100° C. for 16 hr. The suspension was filtered and the resin washed with DMF (5×) and CH$_2$Cl$_2$ (5×). This was then dried in vacuo.

To 400 mg (0.21 mmol) of resin-bound trisubstituted pyrimidine was added 5 mL of a 1:1 solution of TFA/CH$_2$Cl$_2$. The resulting mixture was stirred for 2 hr at 25° C. and then filtered. The filtrate was concentrated in vacuo and the residue was purified by flash column chromatography (SiO$_2$, elution with ethyl acetate) to give the pure trisubstituted pyrimidine 31. Data for 31: MS: m/z (relative intensity) 473.4 (M$^+$+1, 100).

It should be understood that while this invention has been described herein in terms of specific embodiments set forth in detail, such embodiments are presented by way of illustration of general principles, and the invention is not necessarily limited thereto. Modifications and variations in any given material or process step will be readily apparent to those skilled in the art without departing from the true spirit and scope of the following claims, and all such modifications are included within the scope of the present invention.

TABLE 1

| | | MW |
|---|---|---|
| 1. | (structure) | 534.63 |

TABLE 1-continued
| | MW |
|---|---|
| 2. 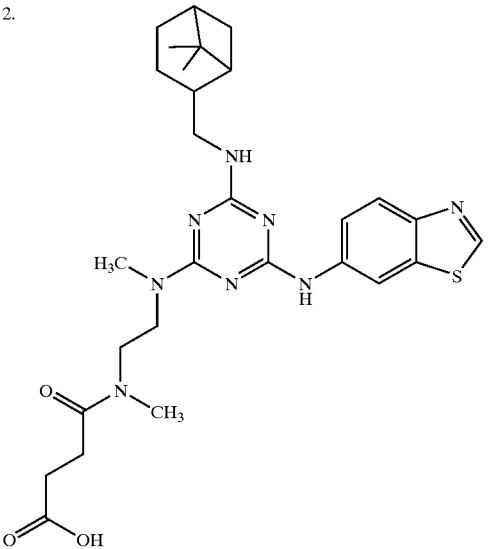 | 578.73 |
| 3. 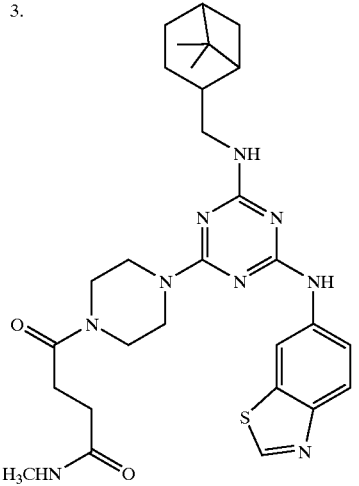 | 577.75 |
| 4. 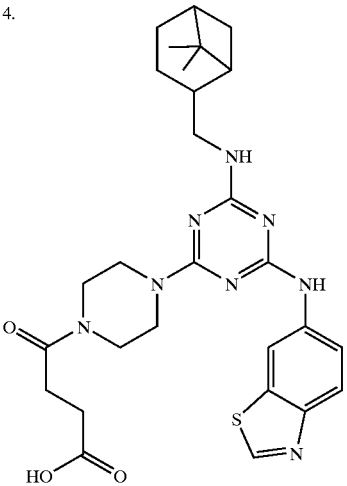 | 564.70 |

TABLE 1-continued
| | MW |
|---|---|
| 5. 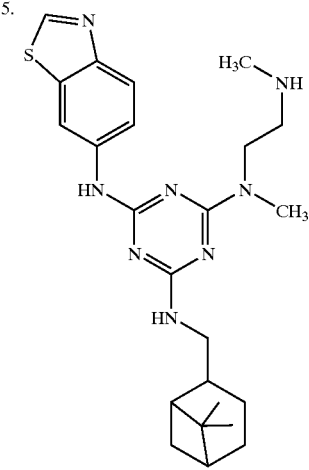 | 466.65 |
| 6. 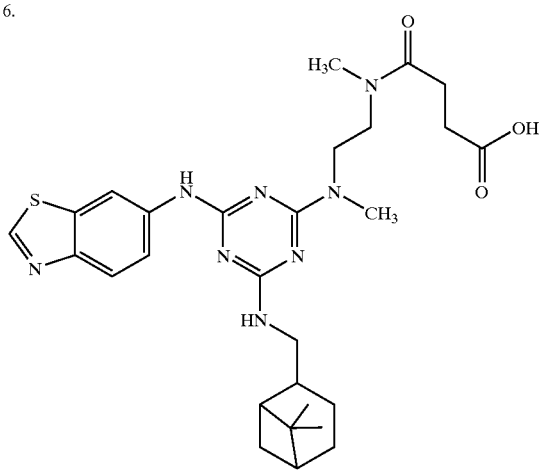 | 566.72 |
| 7. 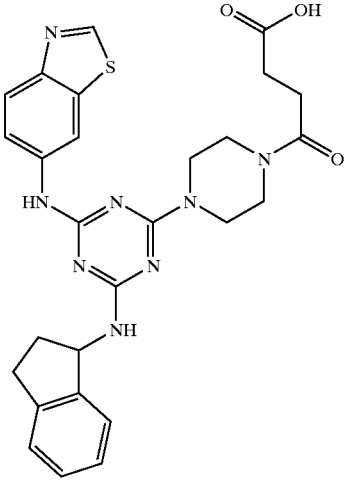 | 544.63 |

TABLE 1-continued

| | MW |
|---|---|
| 8. | 420.49 |
| 9. | 432.50 |
| 10. | 448.59 |
| 11. | 448.59 |

TABLE 1-continued
| | MW |
|---|---|
| 12. 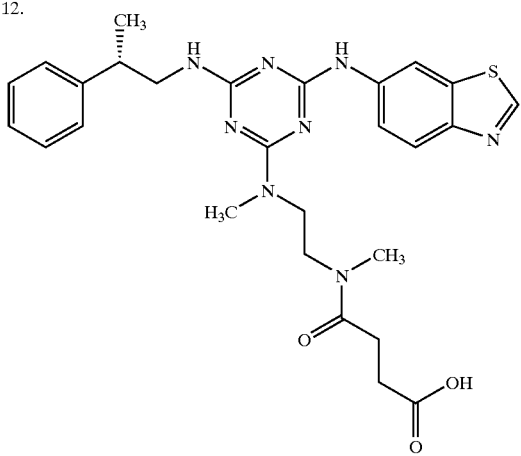 | 548.66 |
| 13. 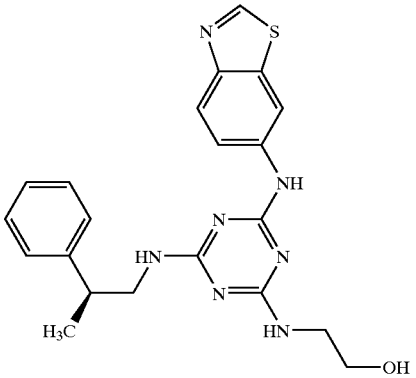 | 421.52 |
| 14. 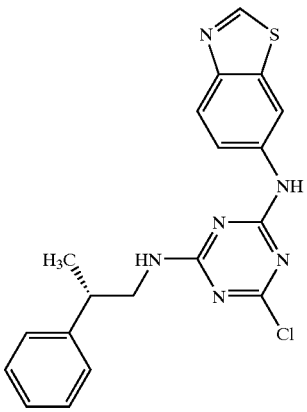 | 396.90 |

TABLE 1-continued
| | MW |
|---|---|
| 15. 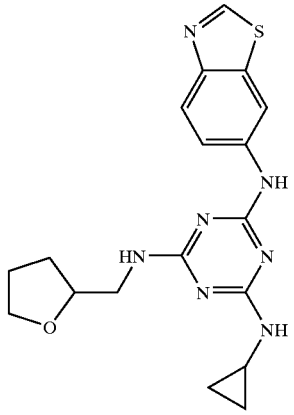 | 383.47 |
| 16. 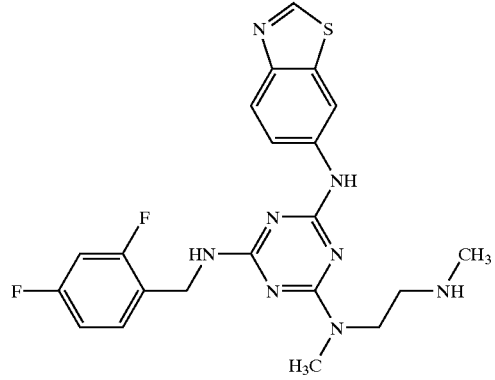 | 456.52 |
| 17. 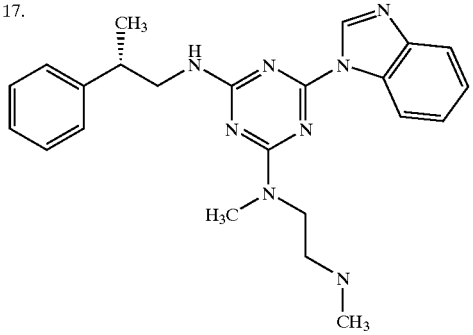 | 416.52 |
| 18. 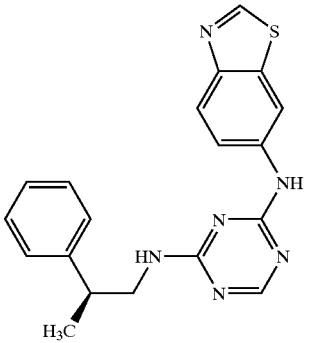 | 362.45 |

TABLE 1-continued

| | MW |
|---|---|
| 19. [structure] | 424.45 |
| 20. [structure] | 524.52 |
| 21. [structure] | 560.69 |

TABLE 1-continued
| | MW |
|---|---|
| 22. 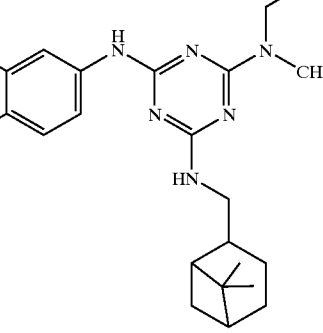 | 460.62 |
| 23. 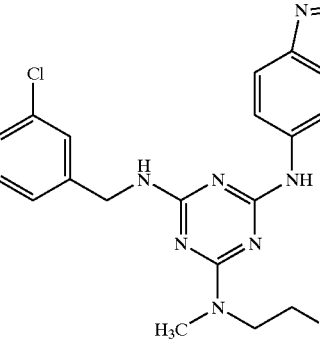 | 489.42 |
| 24. 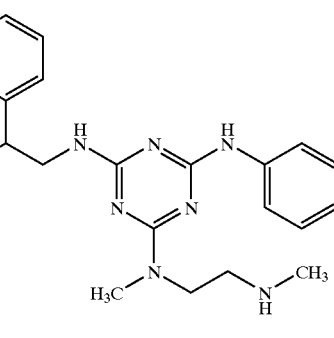 | 462.61 |
| 25. 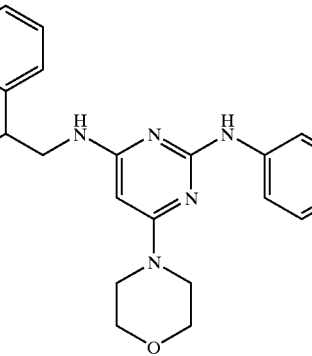 | 440.50 |

TABLE 1-continued

| | MW |
|---|---|
| 26. [structure] | 473.70 |
| 27. [structure] | 448.56 |
| 28. [structure] | 506.67 |
| 29. [structure] | 548.64 |

TABLE 1-continued
| | MW |
|---|---|
| 30. 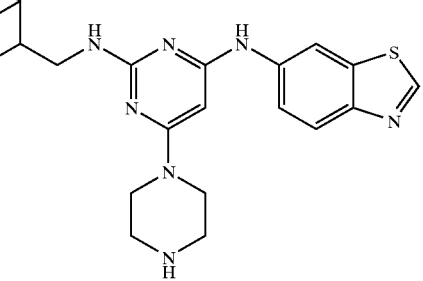 | 463.64 |
| 31. 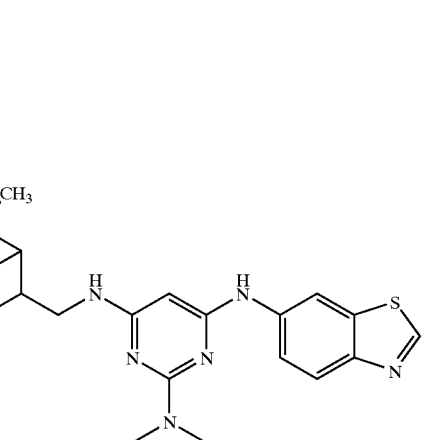 | 463.64 |
| 32. 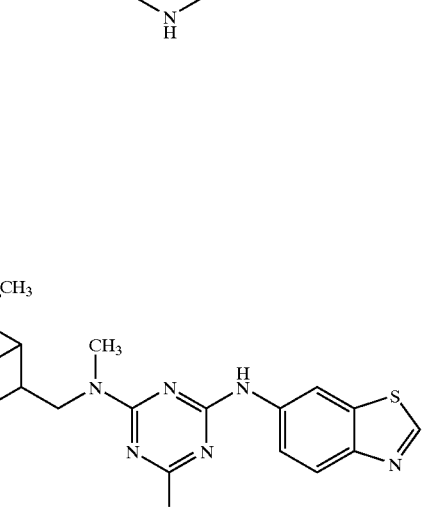 | 520.69 |

TABLE 1-continued
| | MW |
|---|---|
| 33. 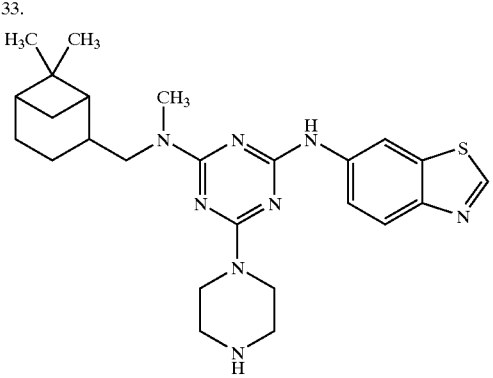 | 478.66 |
| 34. 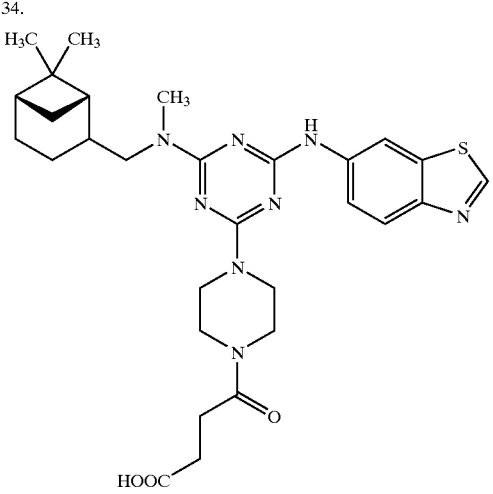 | 578.73 |
| 35. 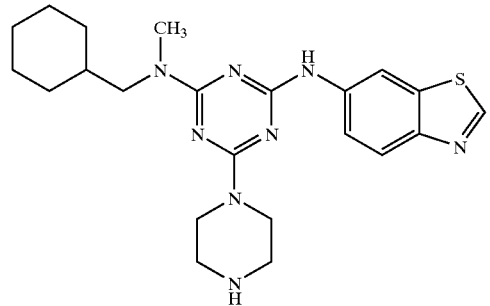 | 424.57 |

TABLE 1-continued

| | MW |
|---|---|
| 36. [structure] | 506.67 |
| 37. [structure] | 556.75 |
| 40. [structure] | 524.64 |
| 41. [structure] | 415.94 |

TABLE 1-continued
| | MW |
|---|---|
| 42. 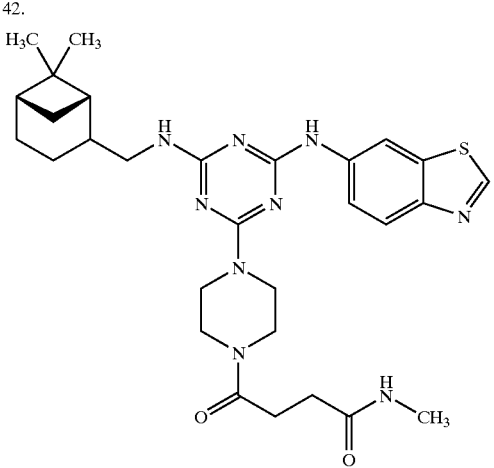 | 578.73 |
| 43. 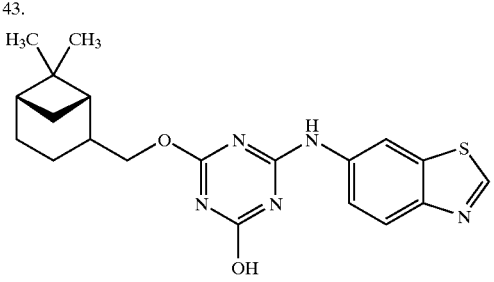 | 480.63 |
| 46. 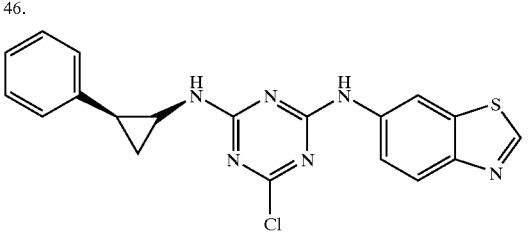 | 394.88 |
| 47. 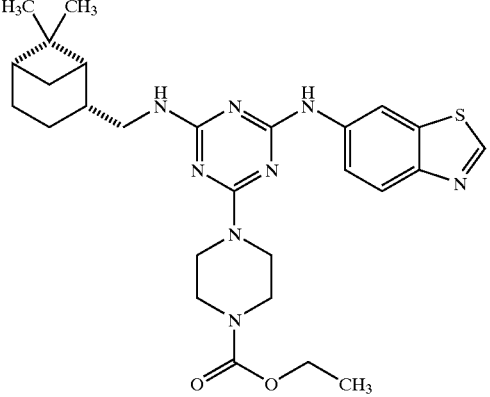 | 536.69 |

TABLE 1-continued
| | MW |
|---|---|
| 48. 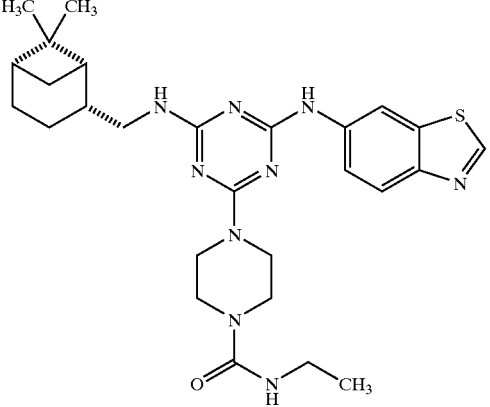 | 535.71 |
| 49. 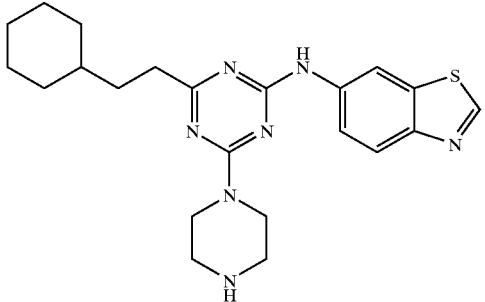 | 423.58 |
| 50. 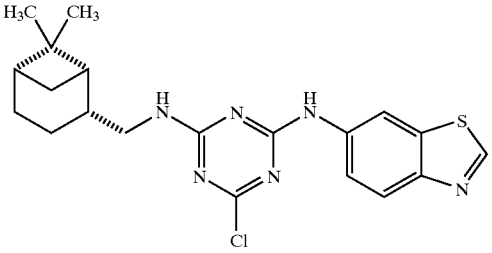 | 414.96 |
| 51. 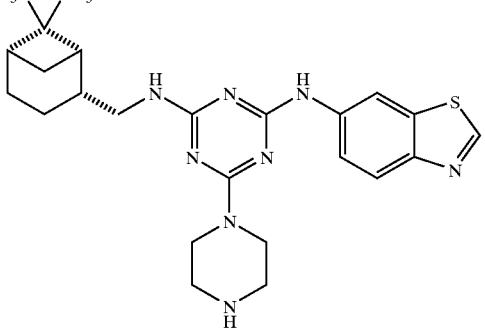 | 464.63 |

TABLE 1-continued
| | MW |
|---|---|
| 52. 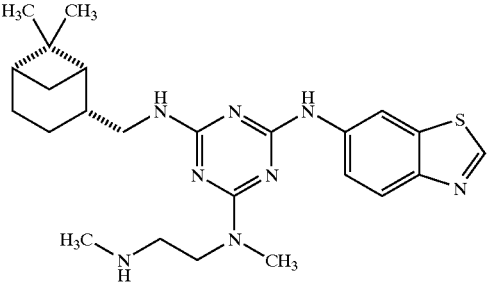 | 466.65 |
| 53. 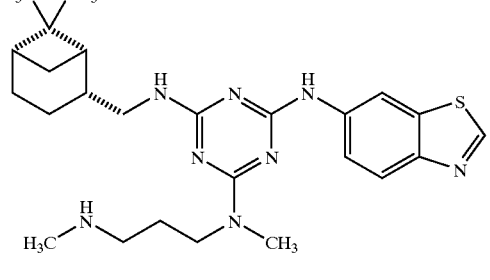 | 480.67 |
| 54. 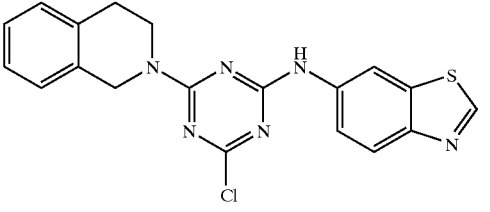 | 394.88 |
| 55. 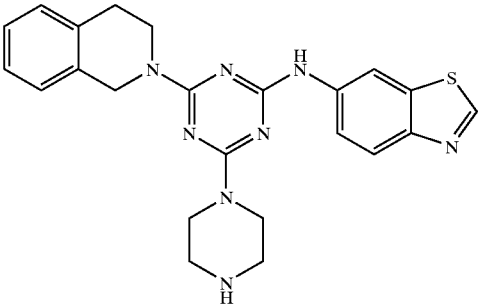 | 444.56 |

TABLE 1-continued

| | MW |
|---|---|
| 56. | 520.69 |
| 57. | 400.93 |
| 58. | 404.53 |
| 59. | 422.59 |
| 60. | 305.79 |

TABLE 1-continued

|  | MW |
|---|---|
| 61. | 396.90 |
| 62. | 414.96 |
| 63. | 410.92 |
| 64. | 546.73 |
| 65. | 460.60 |

TABLE 1-continued
| | | MW |
|---|---|---|
| 66. | 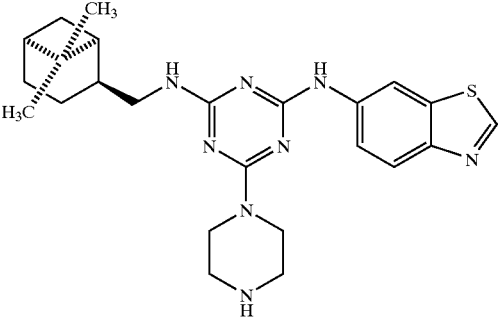 | 464.63 |
| 67. | 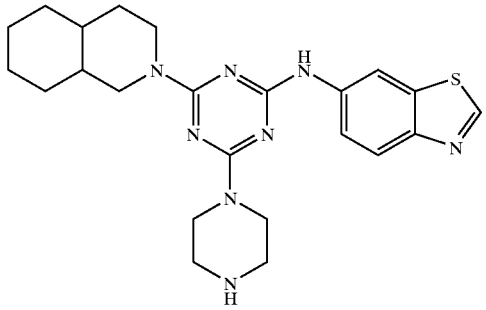 | 450.60 |
| 68. | 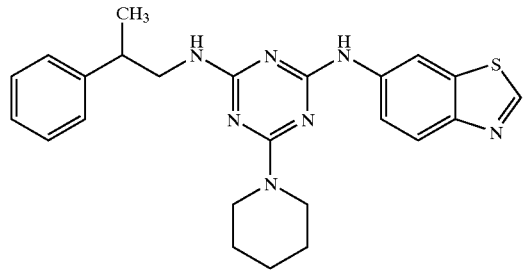 | 445.58 |
| 69. | 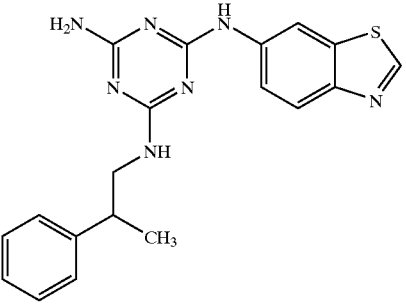 | 377.00 |

TABLE 1-continued
| | MW |
|---|---|
| 70. 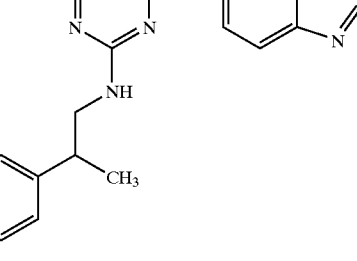 | 391.00 |
| 71. 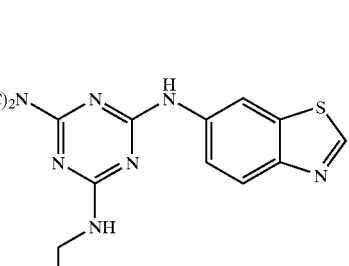 | 405.00 |
| 72. 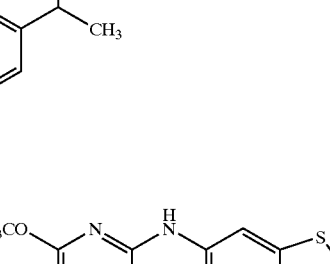 | 392.00 |
| 73. 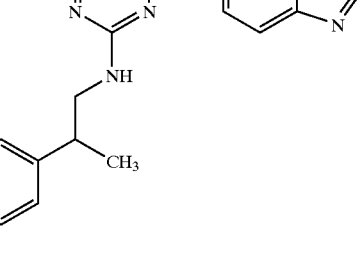 | 420.00 |

TABLE 1-continued

| | MW |
|---|---|
| 74. | 422.93 |
| 75. | 472.61 |
| 76. | 553.71 |
| 77. | 565.72 |

TABLE 1-continued
| | | MW |
|---|---|---|
| 78. | 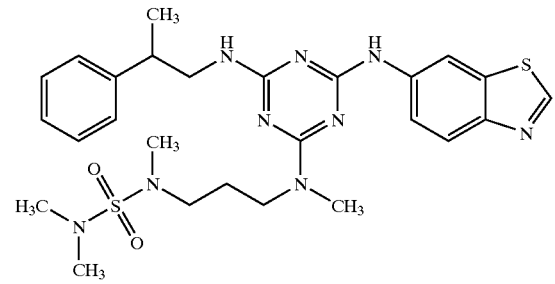 | 569.75 |
| 79. | 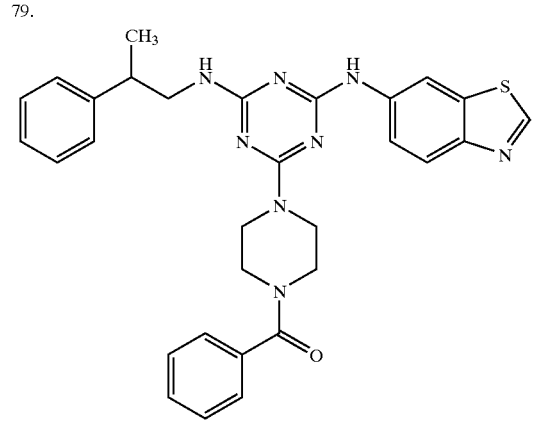 | 550.68 |
| 80. | 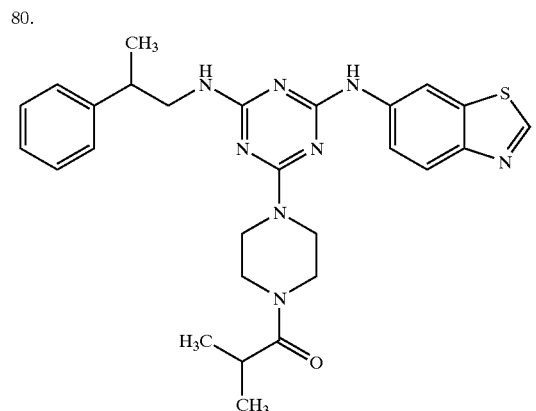 | 516.66 |

TABLE 1-continued
| | MW |
|---|---|
| 81. 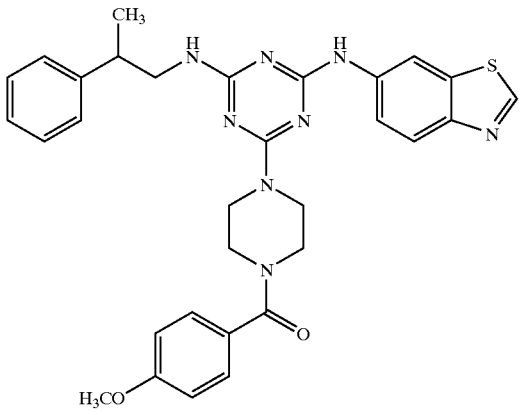 | 580.70 |
| 82. 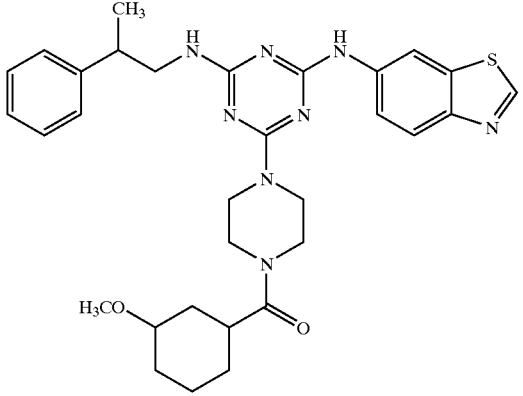 | 586.75 |
| 83. 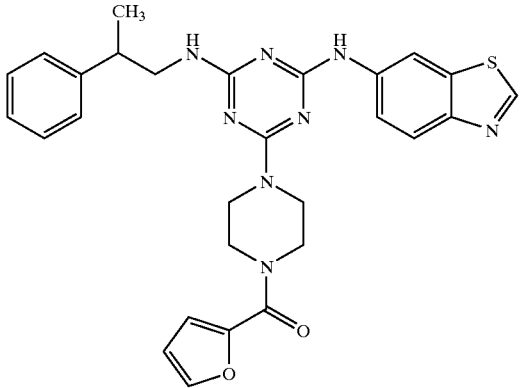 | 540.64 |

TABLE 1-continued

| | MW |
|---|---|
| 84. | 587.81 |
| 85. | 517.65 |
| 86. | 532.70 |
| 87. | 602.79 |

TABLE 1-continued
| | MW |
|---|---|
| 88. 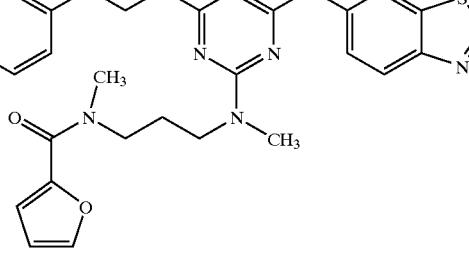 | 556.68 |
| 89. 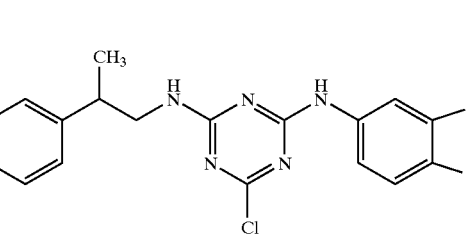 | 431.34 |
| 90. 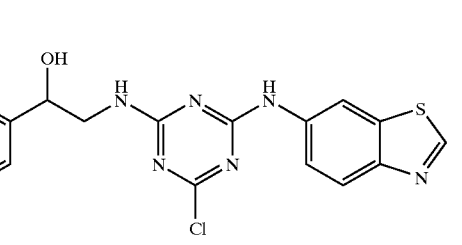 | 398.87 |
| 91. 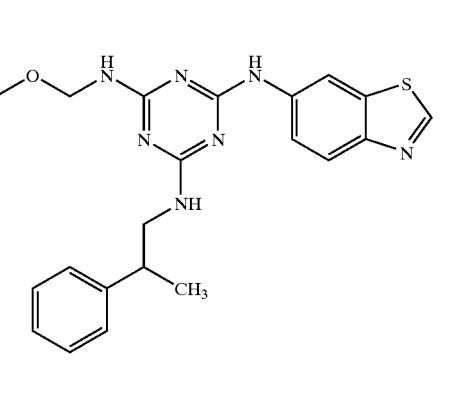 | 406.51 |
| 92. 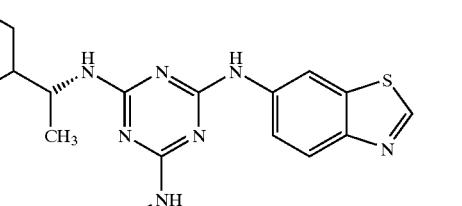 | 383.51 |

TABLE 1-continued

| | MW |
|---|---|
| 93. | 383.51 |
| 94. | 393.47 |
| 95. | 399.42 |
| 96. | 419.55 |
| 97. | 460.60 |
| 98. | 329.37 |

TABLE 1-continued
| | MW |
|---|---|
| 99. 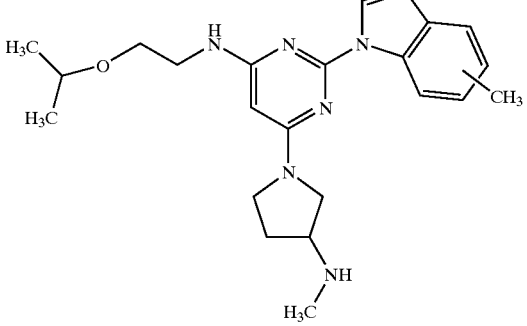 | 409.53 |
| 100. 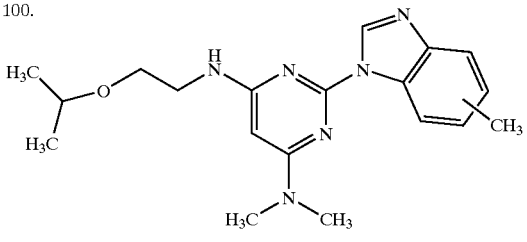 | 354.45 |
| 101. 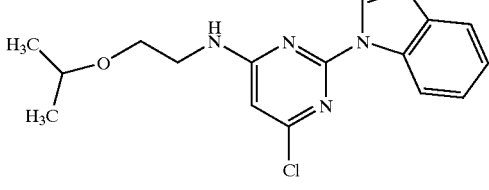 | 331.80 |
| 102. 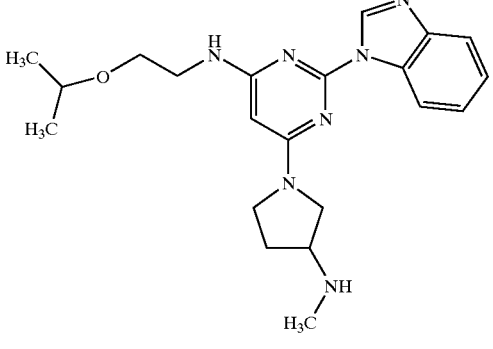 | 395.50 |
| 103. 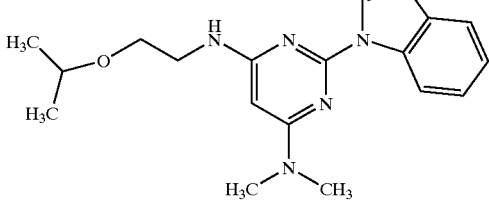 | 340.42 |

TABLE 1-continued
| | MW |
|---|---|
| 104. 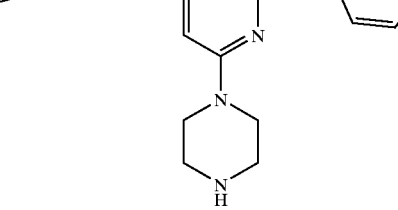 | 381.47 |
| 105. 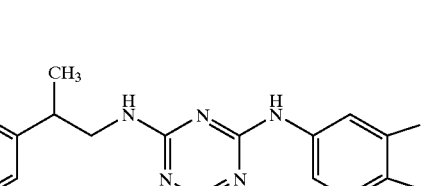 | 488.61 |
| 106. 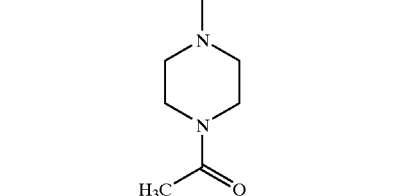 | 518.64 |
| 107. 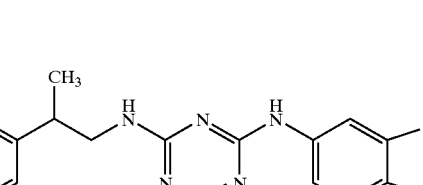 | 551.67 |

TABLE 1-continued
| | MW |
|---|---|
| 108. 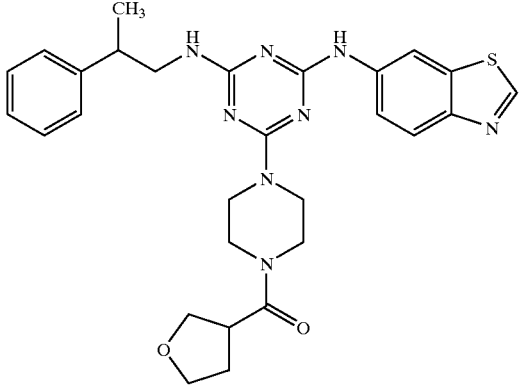 | 544.67 |
| 109. 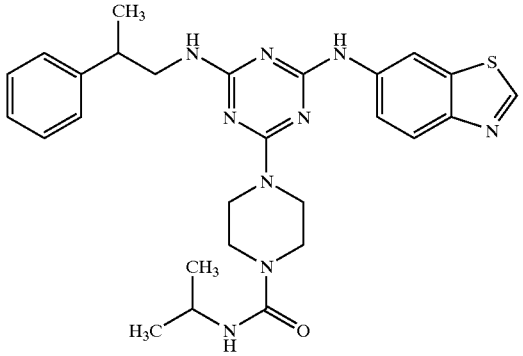 | 531.68 |
| 110. 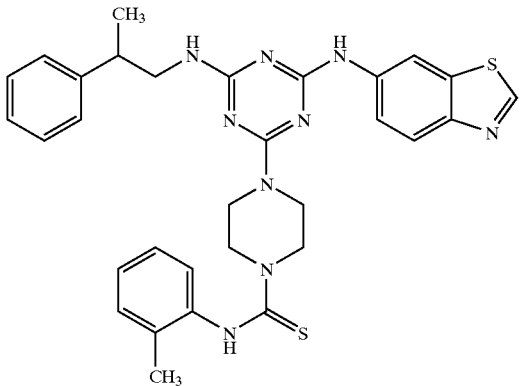 | 595.79 |

TABLE 1-continued

| | MW |
|---|---|
| 111. | 488.61 |
| 112. | 504.65 |
| 113. | 534.68 |
| 114. | 567.71 |

TABLE 1-continued
| | MW |
|---|---|
| 115. 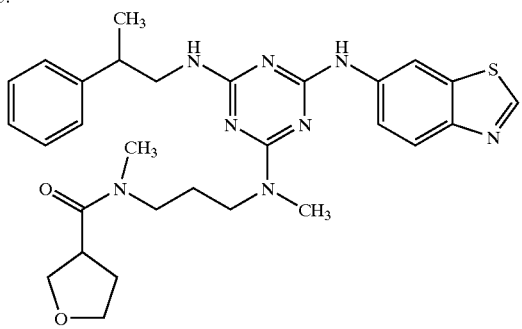 | 560.71 |
| 116. 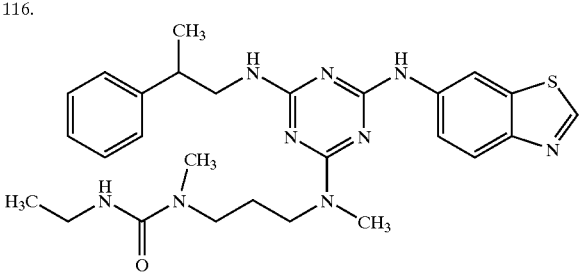 | 533.69 |
| 117. 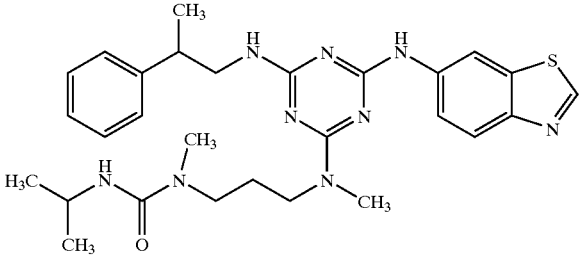 | 547.72 |
| 118. 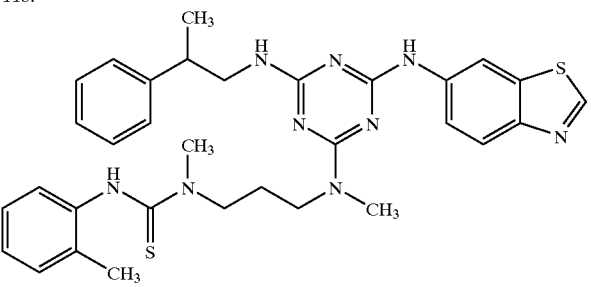 | 611.83 |
| 119. 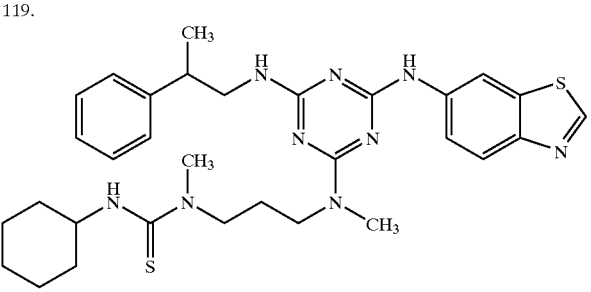 | 603.85 |

TABLE 1-continued

| | MW |
|---|---|
| 120. | 504.65 |
| 121. | 500.62 |
| 122. | 528.67 |
| 123. | 530.65 |

TABLE 1-continued

| | MW |
|---|---|
| 124. | 598.76 |
| 125. | 552.65 |
| 126. | 563.68 |

TABLE 1-continued

| | MW |
|---|---|
| 127. | 556.68 |
| 128. | 529.66 |
| 129. | 543.69 |

TABLE 1-continued
| | MW |
|---|---|
| 130. 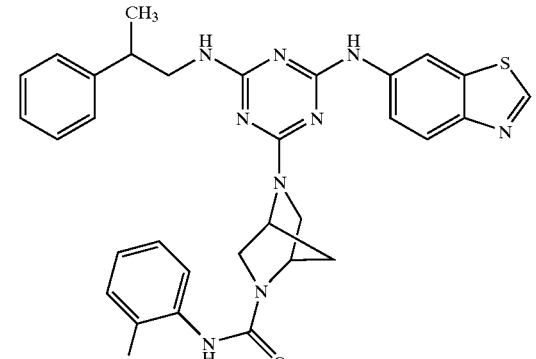 | 607.80 |
| 131. 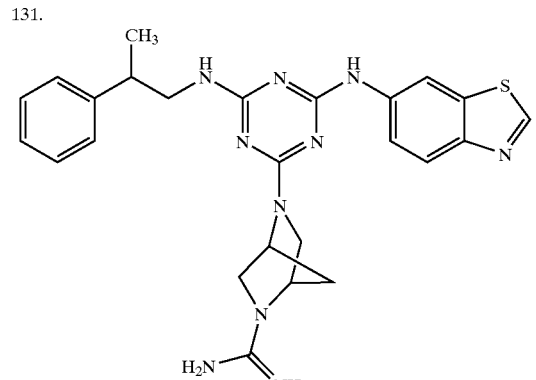 | 500.62 |
| 132. 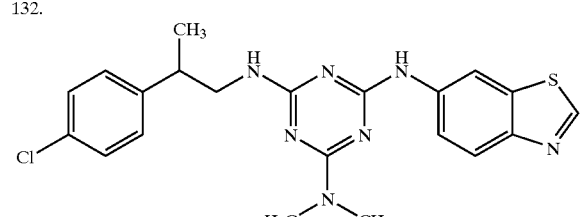 | 439.97 |
| 133. 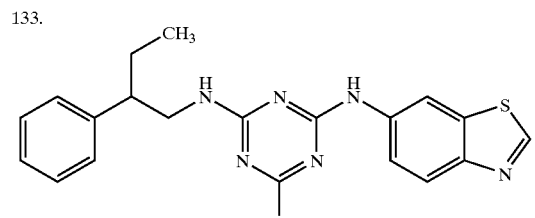 | 410.92 |
| 134. 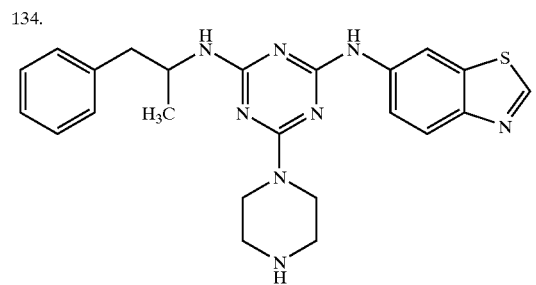 | 446.57 |

TABLE 1-continued

| | MW |
|---|---|
| 135. [structure] | 405.52 |
| 136. [structure] | 419.55 |
| 137. [structure] | 460.60 |
| 138. [structure] | 389.26 |
| 139. [structure] | 355.46 |
| 140. [structure] | 394.88 |

TABLE 1-continued

| | MW |
|---|---|
| 141. | 515.03 |
| 142. | 482.95 |
| 143. | 488.6 |
| 144. | 463.52 |
| 145. | 491.53 |

TABLE 1-continued
| | MW |
|---|---|
| 146. 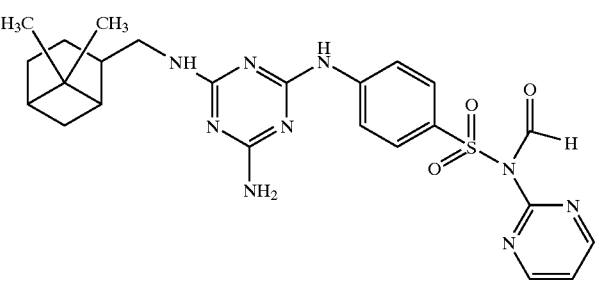 | 523.6 |
| 147. 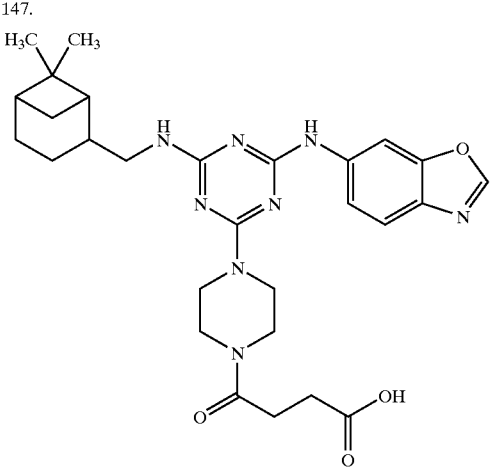 | 548.64 |
| 148. 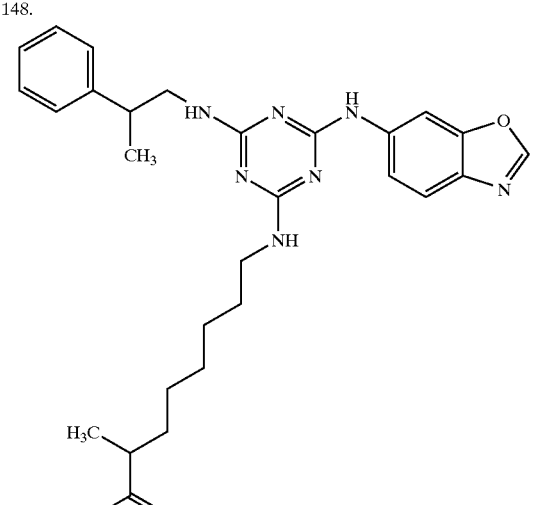 | 546.7 |

TABLE 1-continued
| | MW |
|---|---|
| 149. 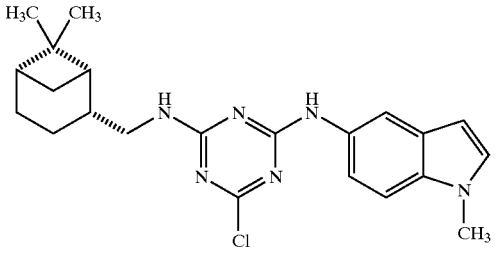 | 410.94 |
| 150. 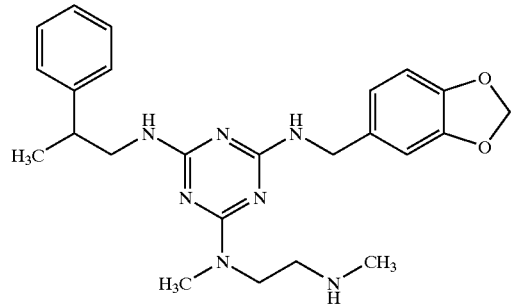 | 449.55 |
| 151. 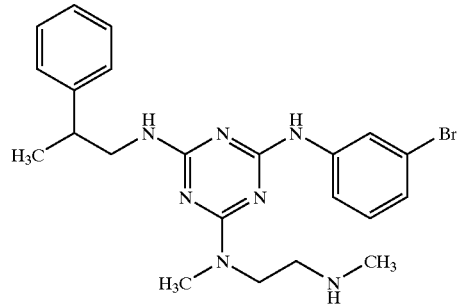 | 470.41 |
| 152. 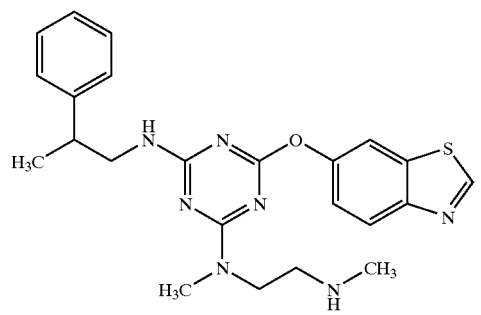 | 449.57 |

TABLE 1-continued
| | MW |
|---|---|
| 153. 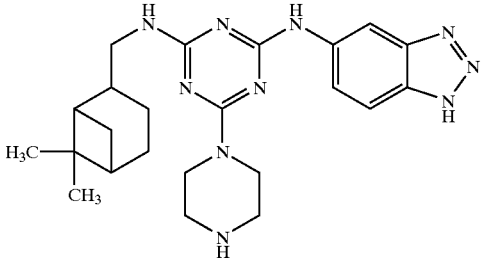 | 448.57 |
| 154. 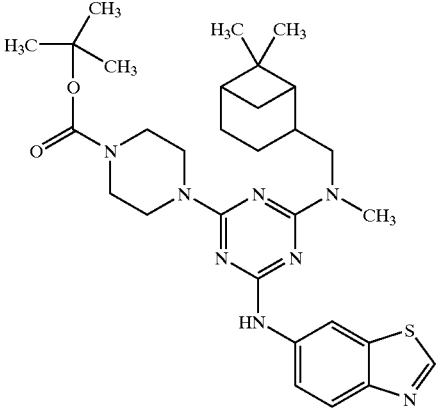 | 578.77 |
| 155. 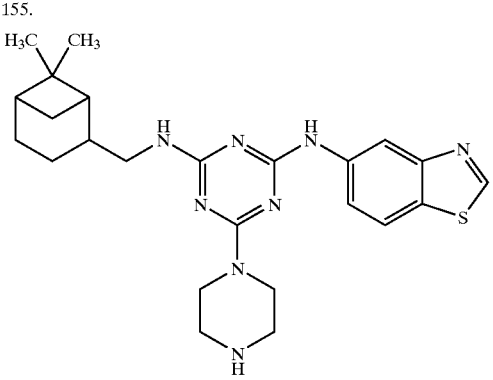 | 464.63 |
| 156. 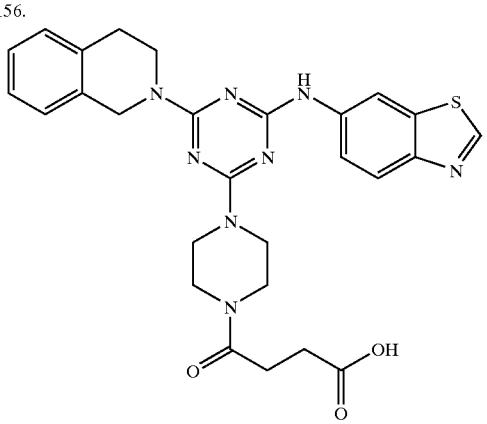 | 544.63 |

TABLE 1-continued
|     |     | MW |
| --- | --- | --- |
| 157. | 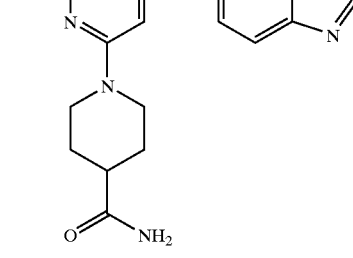 | 423.54 |
| 158. | 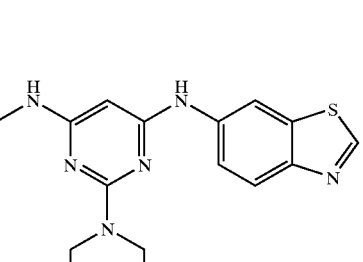 | 423.54 |
| 159. | 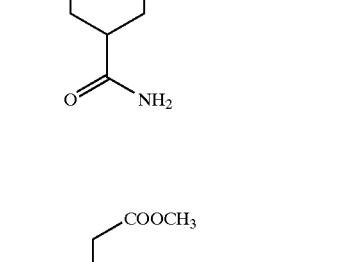 | 489.38 |
| 160. | 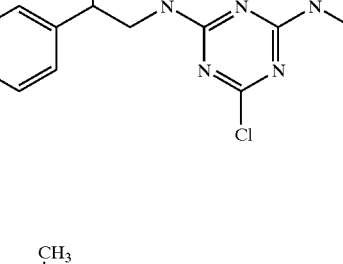 | 596.75 |

TABLE 1-continued
| | MW |
|---|---|
| 161. 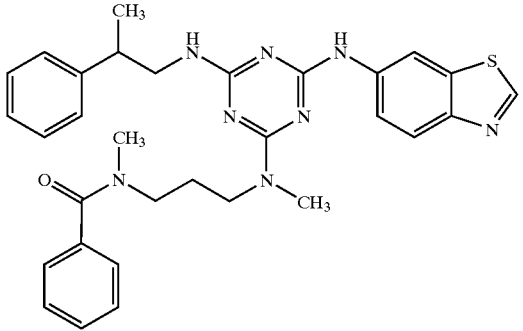 | 566.72 |
| 162. 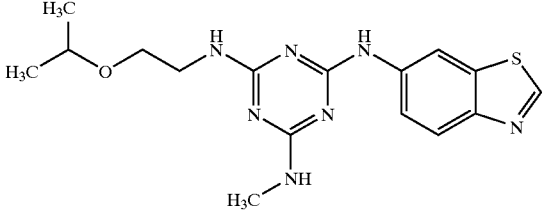 | 359.45 |
| 163. 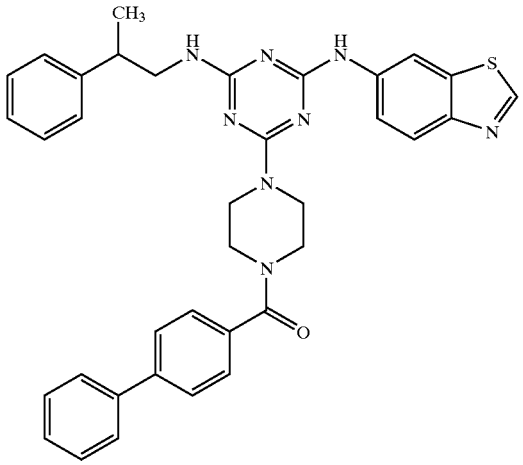 | 626.77 |
| 164. 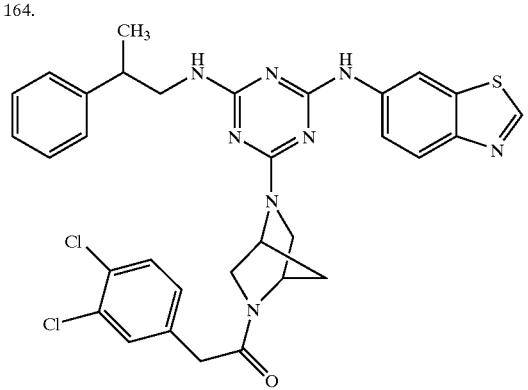 | 645.61 |

TABLE 1-continued

165. MW 478.00

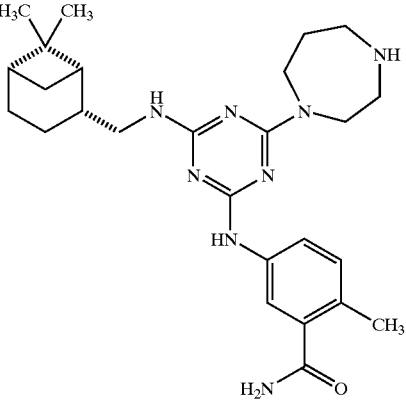

We claim:
1. A compound, or a salt thereof, represented by Formula I,

$$R^1-\underset{Y}{N}-\text{triazine}-R^3R^4, R^2$$

wherein:
$R^1$ is chosen from arylalkyl, fused arylcycloalkyl, cycloalkyl(alkyl), aminocarbonylalkyl, alkoxyalkyl, substituted arylalkyl, heteroaryl other than 2-pyridinyl, heteroarylalkyl, heterocyclylalkyl, and substituted heterocyclylalkyl;
$R^2$ is chosen from

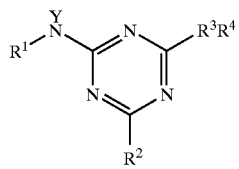

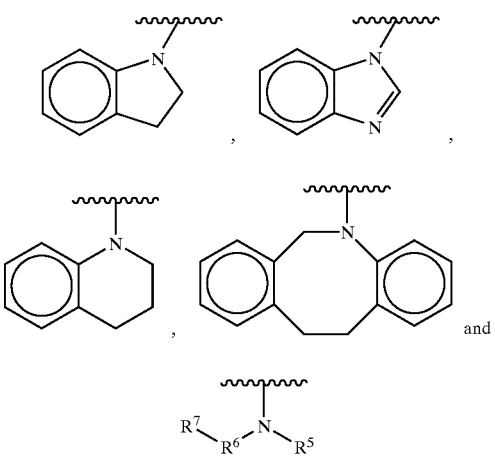

and $R^7-\underset{R^6}{N}-R^5$ wherein
$R^5$ is chosen from H, alkyl and substituted alkyl;
$R^6$ is a direct bond; and
$R^7$ is chosen from heterocyclyl other than 2-pyridinyl and substituted heteroaryl other than 2-pyridinyl;

$R^3$ is chosen from a direct bond,

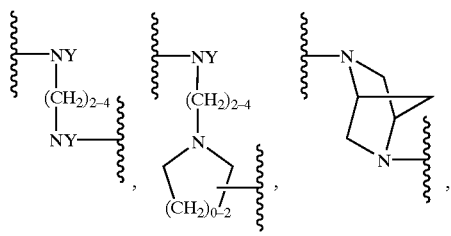

wherein the left hand bond is the point of attachment to the ring and the right hand bond is the point of attachment to $R^1$;

$R^4$ is chosen from H, halogen, alkyl, a saturated cyclic structure of from 1 to 6 carbon atoms containing from 1 to 4 heteroatoms chosen from O, N and S, a bicyclic 9- to 10-membered heteroaryl containing from 1 to 4 heteroatoms chosen from O, N and S, alkylamino, aminocarbonyl, acyl, —C(=NH)NH$_2$,

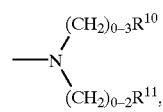

$C(S)NHR^{12}$, $CHR^{13}R^{14}$, $C(O)NHR^{15}$, $C(O)(CH^2)_{0-2}R^{16}$, $S(O_2)R^{17}$, $OR^{18}$,

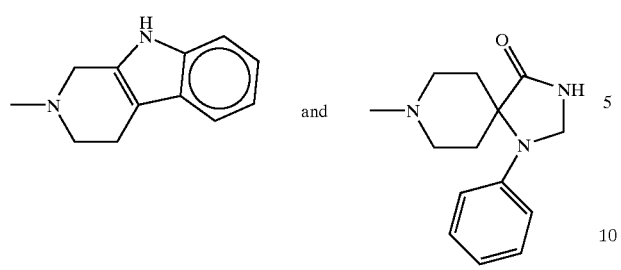 and 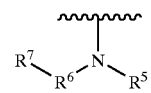

wherein $R^5$ is H, and
$R^7$ is substituted heteroaryl;
$R^3$ is chosen from

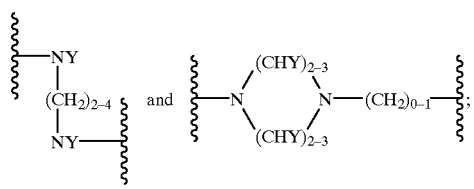

and $R^4$ is $C(O)NHR^{15}$, wherein $R^{15}$ is substituted aryl.

3. A compound, or salt thereof, according to claim 1, wherein:

$R^1$ is chosen from arylalkyl, fused arylcycloalkyl, cycloalkyl(alkyl), aminocarbonylalkyl, heteroarylalkyl and substituted arylalkyl;

$R^2$ is chosen from

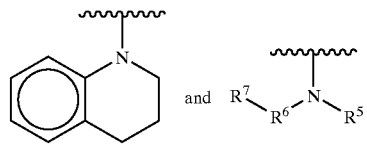

wherein $R^5$ is chosen from H and substituted alkyl;
$R^3$ is chosen from

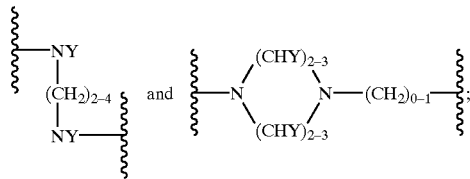

and $R^4$ is H.

4. A compound, or salt thereof, according to claim 1, wherein:

$R^2$ is

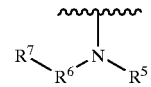

wherein $R^5$ is chosen from H and alkyl; and
$R^7$ is chosen from heterocyclyl and substituted heteroaryl;

wherein $R^{10}$ is chosen from H, OH, alkyl, cycloalkyl and substituted cycloalkyl;

$R^{11}$ is chosen from H, OH, COOH, heteroaryl, substituted heteroaryl, cycloalkyl, substituted cycloalkyl, alkoxy, aminocarbonyl, aminocarbonylalkyl,

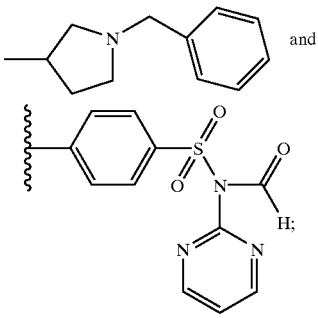

with the proviso that, when $R^3$ is a direct bond, $R^{11}$ cannot be 2-pyridinyl or substituted 2-pyridinyl;

$R^{12}$ is chosen from alkyl, cycloalkyl and aryl;
$R^{13}$ is chosen from H and aryl;
$R^{14}$ is chosen from aryl, substituted aryl, heteroaryl, substituted alkyl, aryl substituted alkyl and alkoxy substituted alkyl,
$R^{15}$ is chosen from alkyl, aryl, substituted aryl and substituted alkyl;
$R^{16}$ is chosen from aryl, substituted aryl, heteroaryl, carboxyl, alkoxy, substituted alkyl, cycloalkyl, substituted cycloalkyl, aminocarbonyl, substituted aminocarbonyl, heterocyclyl and

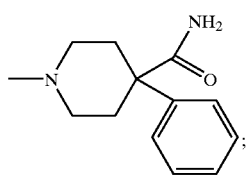

$R^{17}$ is chosen from alkyl and dialkylamino;
$R^{18}$ is chosen from $C_1$ to $C_{20}$ alkyl, substituted $C_1$ to $C_{20}$ alkyl; and
Y is chosen from H and lower alkyl.

2. A compound, or salt thereof, according to claim 1, wherein:

$R^1$ is chosen from arylalkyl, fused arylcycloalkyl, cycloalkyl(alkyl), and substituted arylalkyl;

$R^3$ is chosen from

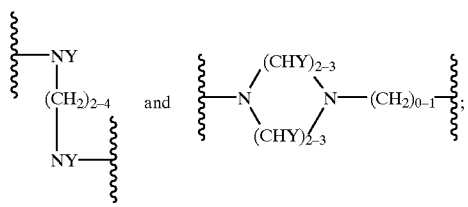

and $R^4$ is chosen from $C(S)NHR^{12}$, $C(O)NHR^{15}$ and $C(O)(CH_2)_{0-2}R^{16}$ wherein $R^{12}$ is aryl;

$R^{15}$ is substituted aryl; and $R^{16}$ is chosen from substituted aryl and heteroaryl.

5. A compound, or salt thereof, according to claim 1, wherein:

$R^1$ is chosen from arylalkyl, fused arylcycloalkyl, cycloalkyl(alkyl), aminocarbonylalkyl, substituted arylalkyl, heteroarylalkyl, heterocyclylalkyl, and substituted heterocyclylalkyl;

$R^2$ is

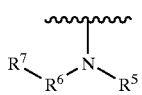

wherein $R^5$ is H; and $R^7$ is chosen from heteroaryl and substituted heteroaryl;

$R^3$ is chosen from

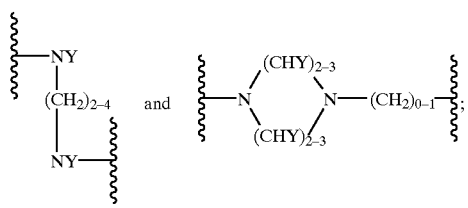

and $R^4$ is chosen from H and $C(O)(CH_2)_{0-2}R^{16}$.

6. A compound, or salt thereof, according to claim 1, wherein:

$R^1$ is chosen from arylalkyl, fused arylcycloalkyl, cycloalkyl(alkyl), alkoxyalkyl, substituted arylalkyl, heteroarylalkyl, and substituted heterocyclylalkyl;

$R^2$ is

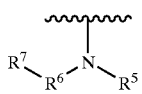

wherein $R^5$ is chosen from H and alkyl; and $R^7$ is heterocyclyl;

$R^3$ is chosen from a direct bond,

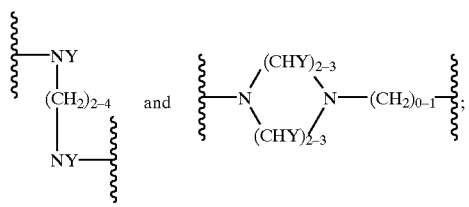

and $R^4$ is chosen from H,

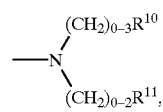

$C(S)NHR^{12}$, $CHR^{13}R^{14}$, $C(O)NHR^{15}$ and $C(O)(CH_2)_{0-3}R^{16}$ wherein $R^{10}$ is H;

$R^{11}$ is H;

$R^{12}$ is alkyl;

$R^{13}$ is H;

$R^{14}$ is chosen from heteroaryl, substituted aryl and alkoxy substituted alkyl;

$R^{15}$ is chosen from aryl and substituted aryl; and $R^{16}$ is substituted aryl.

7. A compound, or salt thereof, according to claim 1, wherein:

$R^{14}$ is chosen from aryl, substituted aryl, heteroaryl, substituted alkyl and aryl substituted alkyl.

8. A compound, or salt thereof, according to claim 1, wherein:

$R^1$ is heteroaryl;

$R^2$ is

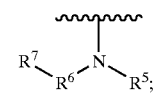

$R^3$ is chosen from a direct bond,

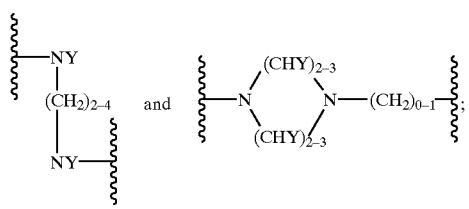

and $R^4$ is chosen from $C(O)(CH_2)_{0-2}R^{16}$ and

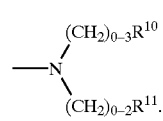

9. A method of inhibiting kinase activity in a mammal, said method comprising administering to said mammal an effective amount of a compound according to claim 1.

10. A method of treating a condition associated with kinase activity in a mammal, said condition chosen from angiogenesis and tumor metastasis, the method comprising administering to a mammal in need of such treatment, an effective amount of a compound according to claim 1.

11. A pharmaceutical composition comprising as a therapeutic agent, a compound according to claim 1 and a pharmaceutically acceptable carrier.

12. A pharmaceutical composition according to claim 11, further comprising one or more additional therapeutic agents.

13. A pharmaceutical composition according to claim 12, wherein said one or more additional therapeutic agents are chosen from anti-inflammatory and immunosuppressive agents.

14. A pharmaceutical composition according to claim 12, wherein said one or more additional therapeutic agents are chosen from antirheumatic, steroid, corticosteroid, NSAID, antipsoriatic, bronchodilator, antiasthmatic and antidiabetic agents.

15. A compound, or a salt thereof, represented by Formula I,

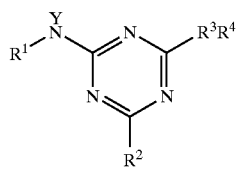

wherein:

$R^1$ is chosen from arylalkyl, fused arylcycloalkyl, cycloalkyl(alkyl), aminocarbonylalkyl, alkoxyalkyl, substituted arylalkyl, heteroaryl other than 2-pyridinyl, heteroarylalkyl, heterocyclylalkyl, and substituted heterocyclylalkyl;

$R^2$ is chosen from heteroaryl, substituted heteroaryl, heterocyclyl, substituted heterocyclyl,

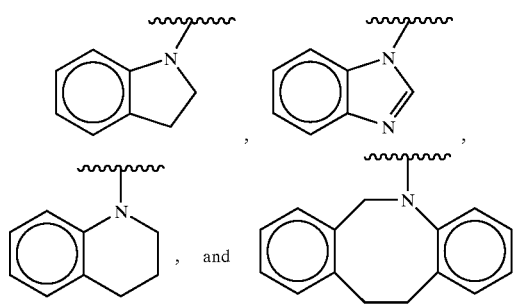

$R^3$ is chosen from

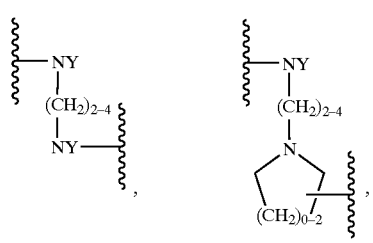

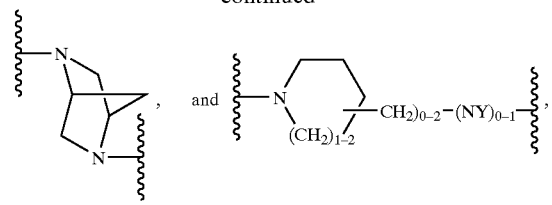

wherein the left hand bond is the point of attachment to the ring and the right hand bond is the point of attachment to $R^4$;

$R^4$ is chosen from H, halogen, alkyl, a saturated cyclic structure of from 1 to 6 carbon atoms containing from 1 to 4 heteroatoms chosen from O, N and S, a bicyclic 9- to 10-membered heteroaryl containing from 1 to 4 heteroatoms chosen from O, N and S, alkylamino, aminocarbonyl, acyl, —C(=NH)NH$_2$,

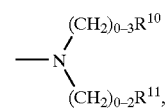

C(S)NHR$^{12}$, CHR$^{13}$R$^{14}$, C(O)NHR$^{15}$, C(O)(CH$^2$)$_{0-2}$R$^{16}$, S(O$_2$)R$^{17}$, OR$^{18}$,

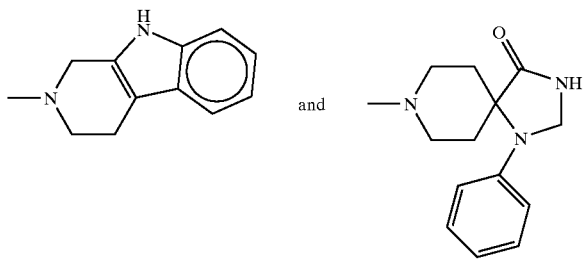

wherein $R^{10}$ is chosen from H, OH, alkyl, cycloalkyl and substituted cycloalkyl;

$R^{11}$ is chosen from H, OH, COOH, aryl, substituted aryl, heteroaryl, substituted heteroaryl, aryl substituted alkyl, cycloalkyl, substituted cycloalkyl, alkoxy, aminocarbonyl, aminocarbonylalkyl,

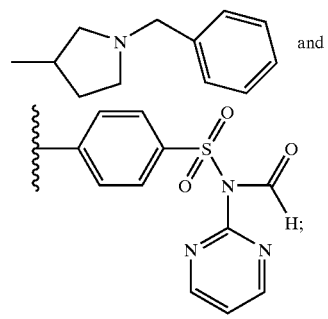

$R^{12}$ is chosen from alkyl, cycloalkyl and aryl;
$R^{13}$ is chosen from H and aryl;
$R^{14}$ is chosen from aryl, substituted aryl, heteroaryl, substituted alkyl, aryl, substituted alkyl and alkoxy substituted alkyl:

$R^{15}$ is chosen from alkyl, aryl, substituted aryl and substituted alkyl;

$R^{16}$ is chosen from aryl, substituted aryl, heteroaryl, carboxyl, alkoxy, substituted alkyl, cycloalkyl, substituted cycloalkyl, aminocarbonyl, substituted aminocarbonyl, heterocyclyl and

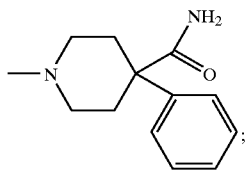

$R^{17}$ is chosen from alkyl and dialkylamino; and $R^{18}$ is chosen from $C_1$ to $C_{20}$ hydrocarbon, substituted $C_1$ to $C_{20}$ hydrocarbon and heteroaryl; and Y is chosen from H and lower alkyl.

16. A compound, or salt thereof, according to claim 15 wherein:

$R^1$ is chosen from arylalkyl, fused arylcycloalkyl, cycloalkyl(alkyl), and substituted arylalkyl; and $R^3$ is chosen from

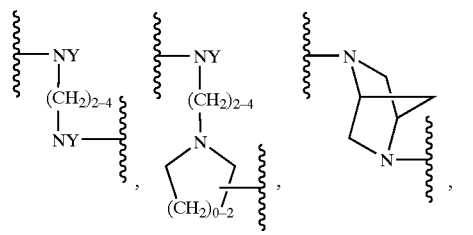

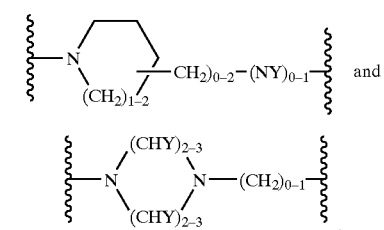
and

17. A compound, or salt thereof, according to claim 16, wherein:

$R^4$ is chosen from H, halogen, alkyl, a saturated cyclic structure of from 1 to 6 carbon atoms containing from 1 to 4 heteroatoms chosen from O, N and S, a bicyclic 9- to 10-membered heteroaryl containing from 1 to 4 heteroatoms chosen from O, N and S, alkylamino, aminocarbonyl,

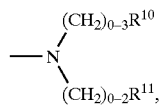

$C(S)NHR$, $CHR^{13}R^{14}$, $C(O)NHR^{15}$, $C(O)(CH_2)_{0-2}R^{16}$, $S(O_2)R^{17}$, $OR^{18}$,

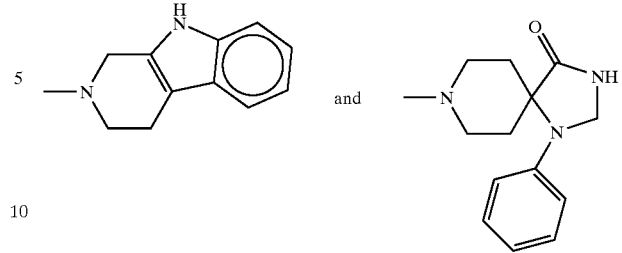

wherein $R^{10}$ is chosen from H, OH, alkyl, cycloalkyl and substituted cycloalkyl;

$R^{11}$ is chosen from H, OH, COOH, aryl, substituted aryl, heteroaryl, substituted heteroaryl, aryl substituted alkyl, cycloalkyl, substituted cycloalkyl, alkoxy, aminocarbonyl, aminocarbonylalkyl,

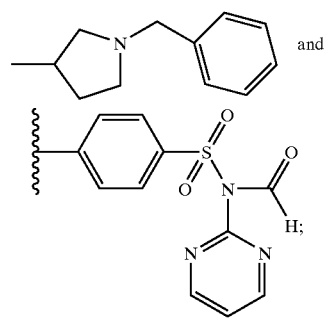

$R^{12}$ is chosen from alkyl and aryl;

$R^{13}$ is chosen from alkyl and aryl;

$R^{14}$ is chosen from aryl, substituted aryl, heteroaryl, substituted alkyl, aryl substituted alkyl and alkoxy substituted alkyl, $R^{15}$ is chosen from alkyl, aryl, substituted aryl and substituted alkyl;

$R^{16}$ is chosen from aryl, substituted aryl, heteroaryl, carboxyl, alkoxy, substituted alkyl, cycloalkyl, substituted cycloalkyl, aminocarbonyl, substituted aminocarbonyl, heterocyclyl and

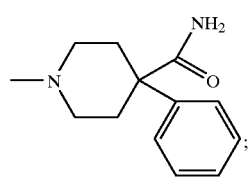

$R^{17}$ is chosen from alkyl and dialkylamino; and $R^{18}$ is chosen from $C_1$ to $C_{20}$ hydrocarbon, substituted $C_1$ to $C_{20}$ hydrocarbon and heteroaryl; and Y is chosen from H and lower alkyl.

18. A compound, or salt thereof, according to claim 1 wherein:

$R^2$ is chosen from

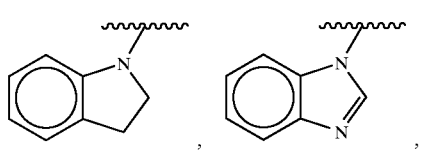

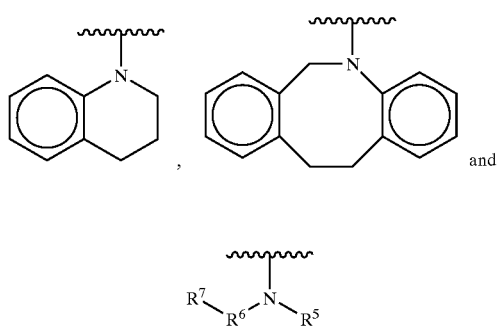

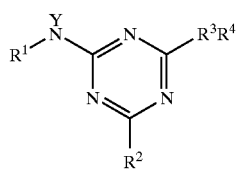

and $R^3$ is a direct bond.

19. A compound, or a salt thereof, represented by Formula I,

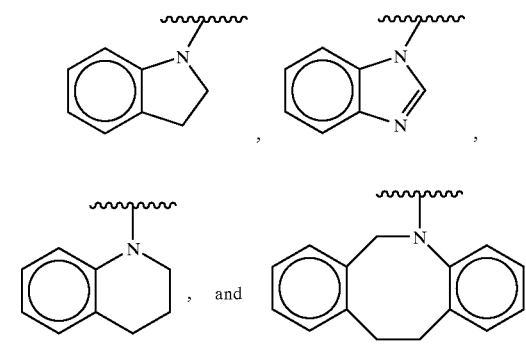

wherein:

$R^1$ is chosen from arylalkyl, fused arylcycloalkyl, cycloalkyl(alkyl), aminocarbonylalkyl, alkoxyalkyl, substituted arylalkyl, heteroaryl other than 2-pyridinyl, heteroarylalkyl, heterocycloalkyl, and substituted heterocyclylalkyl;

$R^2$ is chosen from heteroaryl, substituted heteroaryl, substituted heterocyclyl,

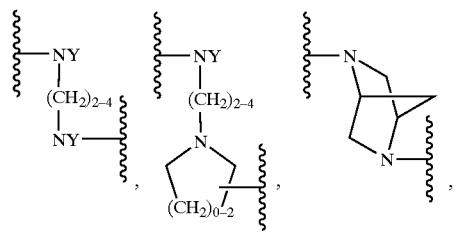

$R^3$ is chosen from

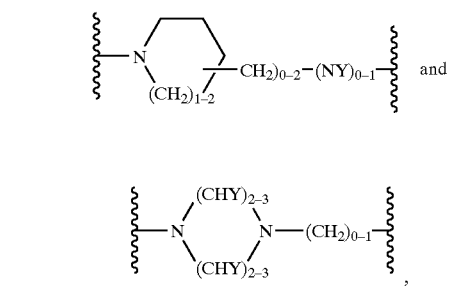

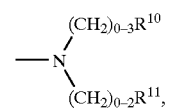

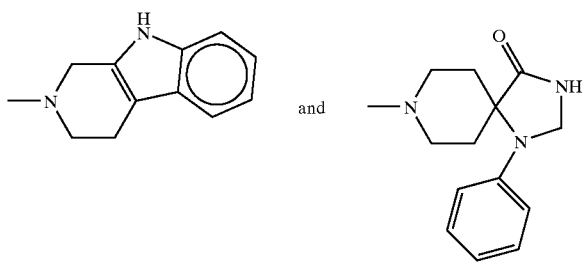

wherein the left hand bond is the point of attachment to the ring and the right hand bond is the point of attachment to $R^1$;

$R^4$ is chosen from halogen, alkyl, a saturated cyclic structure of from 1 to 6 carbon atoms containing from 1 to 4 heteroatoms chosen from O, N and S, a bicyclic 9- to 10-membered heteroaryl containing from 1 to 4 heteroatoms chosen from O, N and S, alkylamino, aminocarbonyl, acyl, —C(=NH)NH$_2$,

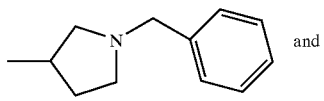

$C(S)NHR^{12}$, $CHR^{13}R^{14}$, $C(O)NHR^{15}$, $C(O)(CH_2)_{0-2}R^{16}$, $S(O_2)R^{17}$, $OR^{18}$, wherein
$R^{10}$ is chosen from H, OH, alkyl, cycloalkyl and substituted cycloalkyl;
$R^{11}$ is chosen from H, OH, COOH, aryl, substituted aryl, heteroaryl, substituted heteroaryl, aryl substituted alkyl, cycloalkyl, substituted heteroalkyl, alkoxy aminocarbonyl, aminocarbonylalkyl, -continued

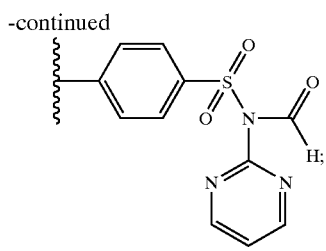

$R^{12}$ is chosen from alkyl cycloalkyl and aryl;

$R^{13}$ is chosen from H and aryl;

$R^{14}$ is chosen from aryl, substituted aryl, heteroaryl, substituted alkyl, aryl substituted alkyl and alkoxy substituted alkyl, $R^{15}$ is chosen from alkyl, aryl, substituted aryl and substituted alkyl;

$R^{16}$ is chosen from aryl, substituted aryl, heteroaryl, carboxyl, alkoxy, substituted alkyl, cycloalkyl, substituted cycloalkyl, aminocarbonyl, substituted aminocarbonyl, heterocyclyl and

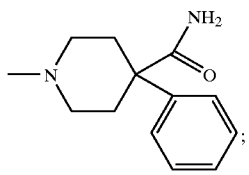

$R^{17}$ is chosen from alkyl and dialkylamino; and $R^{18}$ is chosen from $C_1$ to $C_{20}$ hydrocarbon, substituted $C_1$ to $C_{20}$ hydrocarbon and heteroaryl; and Y is chosen from H and lower alkyl.

20. A compound, or a salt thereof, represented by Formula I,

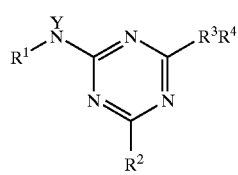

wherein:

$R^1$ is chosen from optionally substituted benzothiazolyl, quinolinyl, benzoxazolyl, benzodioxolyl and benzotriazolyl;

$R^2$ is chosen from halogen, $C_1$ to $C_{20}$ hydrocarbon, hydroxy, heteroaryl, substituted heteroaryl, heterocyclyl, and substituted heterocyclyl;

$R^3$ is chosen from a direct bond,

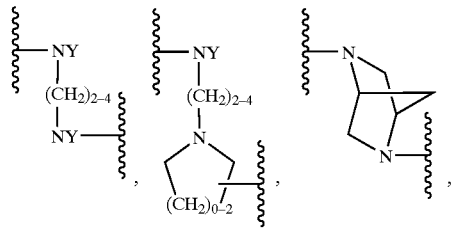

-continued

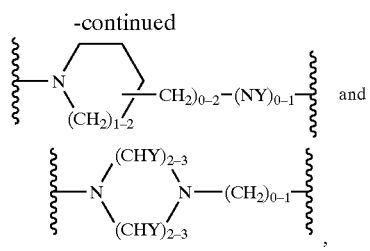

wherein the left hand bond is the point of attachment to the ring and the right hand bond is the point of attachment to $R^4$;

$R^4$ is chosen from H, alkyl, and $OR^{18}$ wherein $R^{18}$ is chosen from $C_1$ to $C_{20}$ hydrocarbon, substituted $C_1$ to $C_{20}$ hydrocarbon and heteroaryl; and Y is chosen from H and lower alkyl.

21. A compound, or a salt thereof, represented by Formula I,

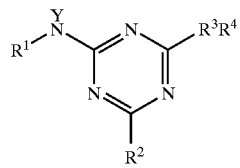

wherein $R^1$ is chosen from aminocarbonylalkyl, alkoxyalkyl, substituted arylalkyl, heteroaryl, heteroarylalkyl, heterocyclylalkyl, and substituted heterocyclylalkyl;

$R^2$ is chosen from benzimidazolyl and substituted benzimidazolyl;

$R^3$ is chosen from a direct bond,

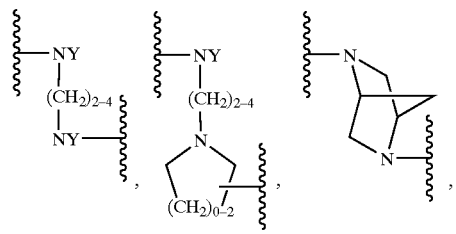

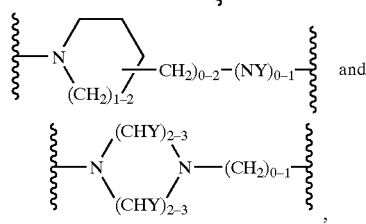

wherein the left hand bond is the point of attachment to the ring and the right hand bond is the point of attachment to $R^4$;

$R^4$ is chosen from H, halogen, alkyl, a saturated cyclic structure of from 1 to 6 carbon atoms containing from 1 to 4 heteroatoms chosen from O, N and S, a bicyclic 9- to 10-membered heteroaryl containing from 1 to 4 heteroatoms chosen from O, N and S, alkylamino, amino carbonyl, acyl, —C(=NH)NH$_2$,

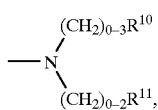

C(S)NHR$^{12}$, CHR$^{13}$R$^{14}$, C(O)NHR$^{15}$, C(O)(CH$_2$)$_{0-2}$R$^{16}$, S(O$_2$)R$^{17}$, OR$^{18}$,

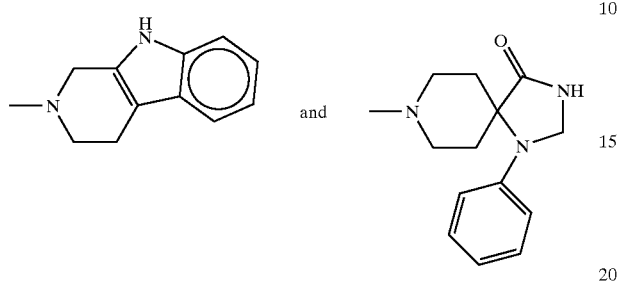

wherein
R$^{10}$ is chosen from H, OH, alkyl, cycloalkyl and substituted cycloalkyl;
R$^{11}$ is chosen from H, OH, COOH, aryl, substituted aryl, heteroaryl, substituted heteroaryl, aryl substituted alkyl, cycloalkyl, substituted cycloalkyl, alkoxy, aminocarbonyl, aminocarbonylalkyl,

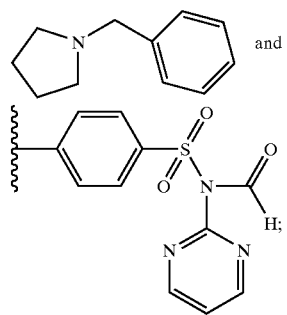

R$^{12}$ is chosen from alkyl and aryl;
R$^{13}$ is chosen from H and aryl;
R$^{14}$ is chosen from aryl, substituted aryl, heteroaryl, substituted alkyl, aryl substituted alkyl and alkoxy substituted alkyl,
R$^{15}$ is chosen from alkyl, aryl, substituted aryl and substituted alkyl;
R$^{16}$ is chosen from aryl, substituted aryl, heteroaryl, carboxyl, alkoxy, substituted alkyl, cycloalkyl, substituted cycloalkyl, aminocarbonyl, substituted aminocarbonyl, heterocyclyl and

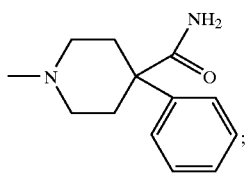

R$^{17}$ is chosen from alkyl and dialkylamino; and
R$^{18}$ is chosen from C$_1$ to C$_{20}$ hydrocarbon, substituted C$_1$ to C$_{20}$ hydrocarbon and heteroaryl; and
Y is chosen from H and lower alkyl.

22. A compound, or salt thereof, according to claim 15, wherein:
R$^1$ is chosen from arylalkyl, fused arylcycloalkyl, cycloalkyl(alkyl), aminocarbonylalkyl, heteroarylalkyl and substituted arylalkyl;
R$^2$ is

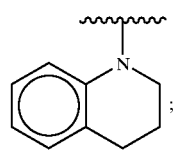

R$^3$ is

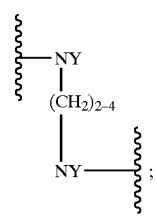

and
R$^4$ is H.

23. A compound, or salt thereof, according to claim 21, wherein:
R$^1$ is chosen from aminocarbonylalkyl, substituted arylalkyl, heteroarylalkyl, heterocyclylalkyl, and substituted heterocyclylalkyl;
R$^2$ is

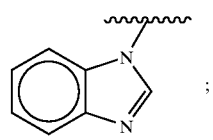

R$^3$ is chosen from

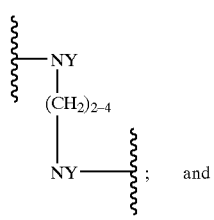

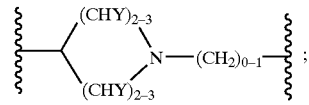

and
R$^4$ is chosen from H and C(O)(CH$_2$)$_{0-2}$R$^{16}$.

24. A compound, or salt thereof, according to claim 21, wherein:
R$^1$ is chosen from arylalkyl, fused arylcycloalkyl, cycloalkyl(alkyl), alkoxyalkyl, substituted arylalkyl, heteroarylalkyl, and substituted heterocyclylalkyl;

$R^2$ is

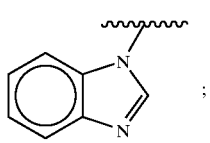;

$R^3$ is chosen from a direct bond,

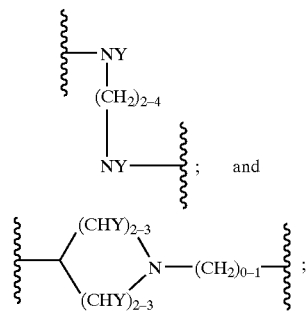

and
$R^4$ is chosen from H,

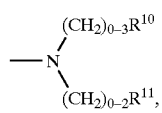

$C(S)NHR^{12}$, $CHR^{13}R^{14}$, $C(O)NHR^{15}$ and $C(O)(CH_2)_{0-2}R^{16}$ wherein $R^{10}$ is H;
$R^{11}$ is H;
$R^{12}$ is alkyl;
$R^{13}$ is H;
$R^{14}$ is chosen from heteroaryl, substituted aryl and alkoxy substituted alkyl;
$R^{15}$ is chosen from aryl and substituted aryl; and
$R^{16}$ is substituted aryl.

25. A compound, or salt thereof, according to claim 1 wherein:

$R^2$ is chosen from

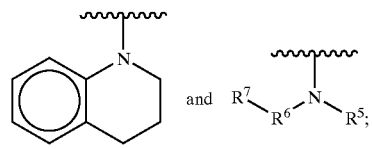

$R^3$ is chosen from

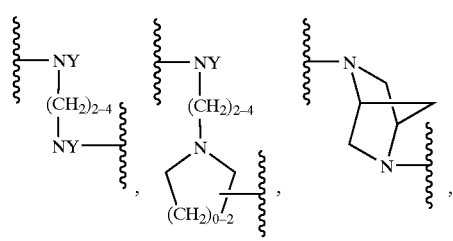

-continued

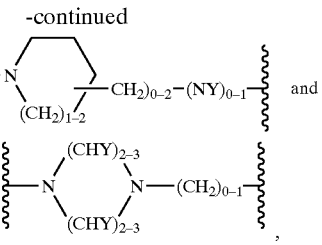

$R^4$ is chosen from H, alkyl a saturated cyclic structure of from 1 to 6 carbon atoms containing from 1 to 4 heteroatoms chosen from O, N and S, a bicyclic 9- to 10-membered heteroaryl containing from 1 to 4 heteroatoms chosen from O, N and S, aminocarbonyl, acyl —C(=NH)NH$_2$, C(S)NHR$^{12}$, CHR$^{13}$R$^{14}$, C(O)NHR$^{15}$, C(O)(CH$_2$)$_{0-2}$$^{16}$, and S(O$_2$)R$^{17}$.

26. A compound, or salt thereof, according to claim 1 wherein:

$R^1$ is chosen from substituted arylalkyl, heterocyclylalkyl, and substituted heterocyclylalkyl;

$R^2$ is

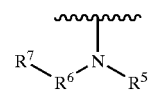

wherein $R^5$ is chosen from H, alkyl and substituted alkyl;
$R^6$ is a direct bond; and
$R^7$ is chosen from optionally substituted benzothiazolyl, quinolinyl, benzoxazolyl, benzodioxolyl and benzotriazolyl;

$R^3$ is chosen from a direct bond,

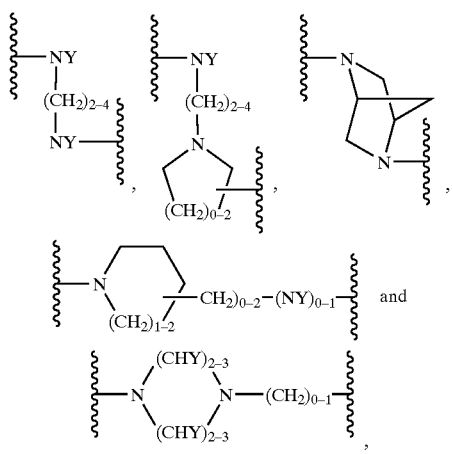

wherein the left hand bond is the point of attachment to the ring and the right hand bond is the point of attachment to $R^4$;

$R^4$ is chosen from H, halogen, alkyl, a bicyclic 9- to 10-membered heteroaryl containing from 1 to 4 heteroatoms chosen from O, N and S, alkylamino, aminocarbonyl, acyl, —C(=NH)NH$_2$,

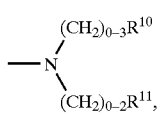

C(S)NHR$^{12}$, CHR$^{13}$R$^{14}$, C(O)NHR$^{15}$, C(O)(CH$_2$)$_{0-2}$
R$^{16}$, S(O)R$^{17}$, OR$^{18}$,

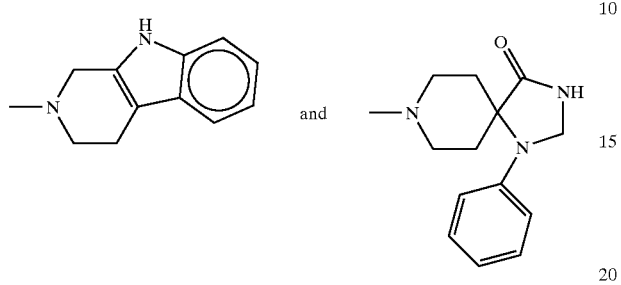

wherein
R$^{10}$ is chosen from H, OH, alkyl, cycloalkyl and substituted cycloalkyl;
R$^{11}$ is chosen from H, OH, COOH, cycloalkyl, substituted cycloalkyl, alkoxy, aminocarbonyl, aminocarbonylalkyl,

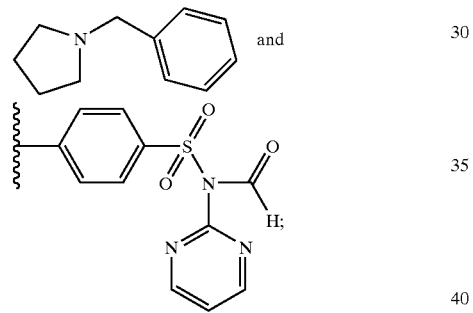

R$^{12}$ is chosen from alkyl cycloalkyl and aryl;
R$^{13}$ is chosen from H and aryl;
R$^{14}$ is chosen from aryl, substituted aryl, heteroaryl, substituted alkyl, aryl substituted alkyl and alkoxy substituted alkyl,
R$^{15}$ is chosen from alkyl, aryl, substituted aryl and substituted alkyl;
R$^{16}$ is chosen from aryl, substituted aryl, heteroaryl, carboxyl, alkoxy, substituted alkyl, cycloalkyl, substituted cycloalkyl, aminocarbonyl, substituted aminocarbonyl, heterocyclyl and

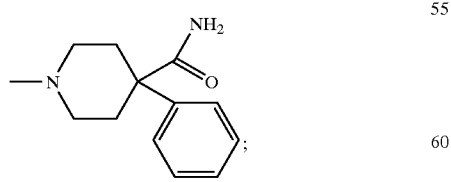

R$^{17}$ is chosen from alkyl and dialkylamino; and
R$^{18}$ is chosen from C$_1$ to C$_{20}$ alkyl, substituted C$_1$ to C$_{20}$ alkyl; and
Y is chosen from H and lower alkyl.

27. A compound, or salt thereof, according to claim 26, wherein
R$^3$ is a direct bond; and
R$^4$ is chosen from H, halogen, alkyl, alkylamino, and

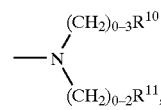

wherein
R$^{10}$ is chosen from H, OH, alkyl, cycloalkyl and substituted cycloalkyl;
R$^{11}$ is chosen from H, OH, COOH, cycloalkyl, substituted cycloalkyl, alkoxy, aminocarbonyl, aminocarbonylalkyl,

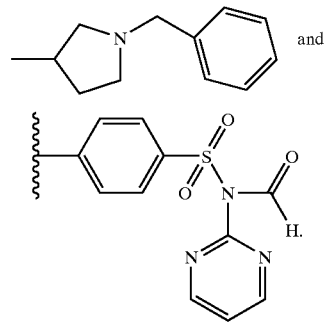

28. A compound, or a salt thereof, represented by Formula I,

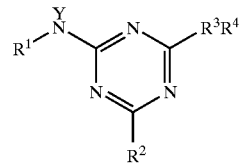

wherein:
R$^1$ is chosen from C$_1$ to C$_{20}$ hydrocarbon, alkoxyalkyl, substituted arylalkyl, heteroaryl, heteroarylalkyl, heterocyclylalkyl, and substituted heterocyclylalkyl;
R$^2$ is

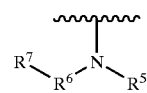

wherein
R$^5$ is chosen from H, alkyl and substituted alkyl;
R$^6$ is a direct bond; and
R$^7$ is chosen from H, acyl, alkyl, and substituted alkyl;
R$^3$ is a direct bond;

$R^4$ is

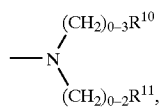

wherein
$R^{10}$ is chosen from H and alkyl;
$R^{11}$ is chosen from benzothiazolyl, quinolinyl, benzoxazolyl, benzodioxolyl and benzotriazolyl; and substituted benzothiazolyl, quinolinyl, benzoxazolyl, benzodioxolyl and benzotriazolyl;
Y is chosen from H and lower alkyl.

29. A compound, or a salt thereof, represented by Formula I,

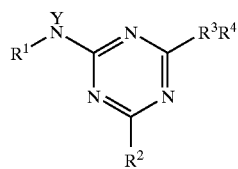

wherein
$R^1$ is $C_1$ to $C_{20}$ hydrocarbon;
$R^2$ is

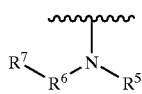

wherein
$R^5$ is chosen from H, alkyl and substituted alkyl;
$R^6$ is a direct bond; and
$R^7$ is chosen from benzothiazolyl, quinolinyl, benzoxazolyl, benzodioxolyl and benzotriazolyl; and substituted benzothiazolyl, quinolinyl, benzoxazolyl, benzodioxolyl and benzotriazolyl;
$R^3$ is a direct bond;
$R^4$ is chosen from H, halogen, alkyl, aminocarbonyl, acyl, —C(—NH)NH$_2$, C(S)NHR$^{12}$, CHR$^{13}$R$^{14}$, C(O)NHR$^{15}$, C(O)(CH$_2$)$_{0-2}$R$^{16}$, S(O$_2$)R$^{17}$, OR$^{18}$,

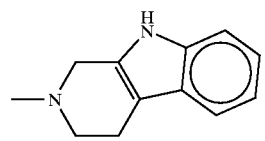 and 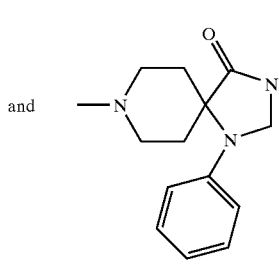

wherein
$R^{12}$ is chosen from alkyl cycloalkyl and aryl;
$R^{13}$ is chosen from H and aryl;
$R^{14}$ is chosen from aryl, substituted aryl, heteroaryl, substituted alkyl, aryl substituted alkyl and alkoxy substituted alkyl,
$R^{15}$ is chosen from alkyl, aryl, substituted aryl and substituted alkyl;

$R^{16}$ is chosen from aryl, substituted aryl, heteroaryl, carboxyl, alkoxy, substituted alkyl, cycloalkyl, substituted cycloalkyl, aminocarbonyl, substituted aminocarbonyl, heterocyclyl and

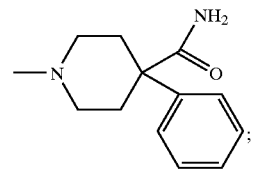

$R^{17}$ is chosen from alkyl and dialkylamino; and
$R^{18}$ is chosen from $C_1$ to $C_{20}$ alkyl, substituted $C_1$ to $C_{20}$ alkyl; and
Y is chosen from H and lower alkyl.

30. A compound, or a salt thereof, represented by Formula XX, XXI or XXII,

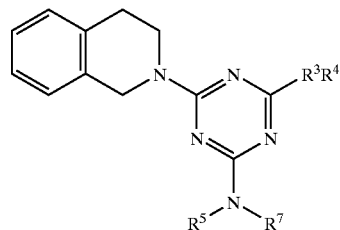

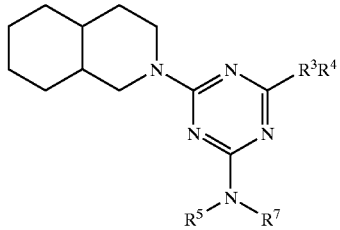

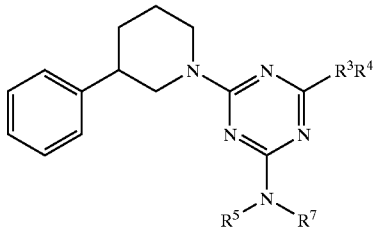

wherein
$R^5$ is chosen from H, alkyl and substituted alkyl;
$R^7$ is chosen from aryl, substituted aryl, heterocyclyl, heteroaryl, and substituted heteroaryl;
$R^3$ is chosen from a direct bond,

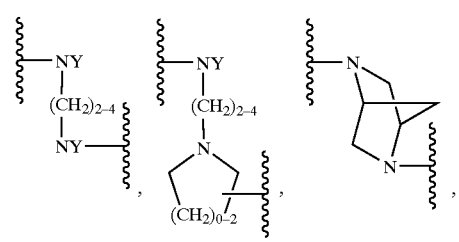

-continued

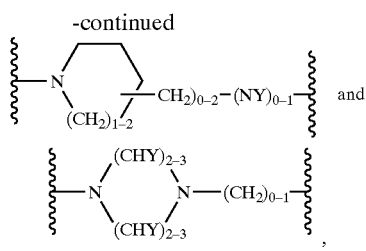

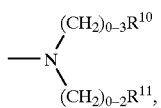

wherein the left hand bond is the point of attachment to the ring and the right hand bond is the point of attachment to $R^4$;

$R^4$ is chosen from H, halogen, alkyl, a saturated cyclic structure of from 1 to 6 carbon atoms containing from 1 to 4 heteroatoms chosen from O, N and S, a bicyclic 9- to 10-membered heteroaryl containing from 1 to 4 heteroatoms chosen from O, N and S, alkylamino, aminocarbonyl, acyl, —C(=NH)NH$_2$,

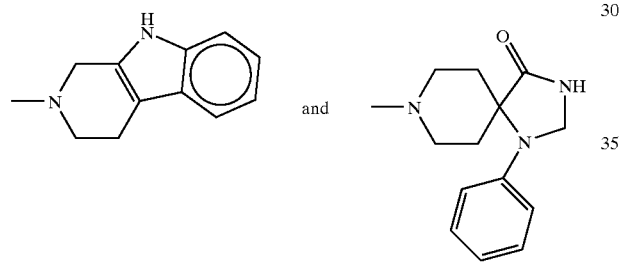

C(S)NHR$^{12}$, CHR$^{13}$R$^{14}$, C(O)NHR$^{15}$, C(O)(CH$_2$)$_{0-2}$R$^{16}$, S(O$_2$)R$^{17}$, OR$^{18}$, wherein $R^{10}$ is chosen from H, OH, alkyl, cycloalkyl and substituted cycloalkyl;

$R^{11}$ is chosen from H, OH, COOH, heteroaryl, substituted heteroaryl, cycloalkyl, substituted cycloalkyl, alkoxy, aminocarbonyl, aminocarbonylalkyl,

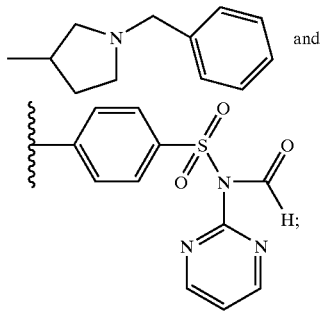

$R^{12}$ is chosen from alkyl cycloalkyl and aryl;

$R^{13}$ is chosen from H and aryl;

$R^{14}$ is chosen from aryl, substituted aryl, heteroaryl, substituted alkyl, aryl substituted alkyl and alkoxy substituted alkyl, $R^{15}$ is chosen from alkyl, aryl, substituted aryl and substituted alkyl;

$R^{16}$ is chosen from aryl, substituted aryl, heteroaryl, carboxyl, alkoxy, substituted alkyl, cycloalkyl, substituted cycloalkyl, aminocarbonyl, substituted aminocarbonyl, hctcrocylyl and

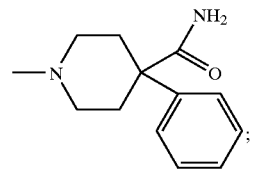

$R^{17}$ is chosen from alkyl and dialkylamino; and $R^{18}$ is chosen from $C_1$ to $C_{20}$ alkyl, substituted $C_1$ to $C_{20}$ alkyl.

* * * * *

UNITED STATES PATENT AND TRADEMARK OFFICE
CERTIFICATE OF CORRECTION

PATENT NO.    : 6,943,161 B2
DATED         : September 13, 2005
INVENTOR(S)   : Erickson et al.

It is certified that error appears in the above-identified patent and that said Letters Patent is hereby corrected as shown below:

Title page,
Item [73], Assignee, delete "Pharmacopela" and insert -- Pharmacopeia --.

Column 117,
Lines 45-47, delete structure 2

Column 118,
Line 50, delete "$R^1$" and insert -- $R^4$ --.

Column 122,
Line 22, delete "$_{0-3}$" and insert -- $_{0-2}$ --.

Column 124,
Lines 1-10, delete "$_{0-1}$" at the end of the second structure

Column 128,
Lines 15-19, delete "$_{0-1}$" at the end of the second structure.
Lines 20-24, delete "$_{0-1}$" at the end of the second structure.
Line 28, delete "$R^1$" and insert -- $R^4$ --.
Line 61, delete the word "heteroalkyl" and insert -- cycloalkyl --.

Column 135,
Line 8, delete "$S(O)R^{17}$" and insert -- $S(O_2)R^{17}$ --.

Signed and Sealed this

Sixth Day of December, 2005

JON W. DUDAS
*Director of the United States Patent and Trademark Office*